(12) United States Patent
Bleich et al.

(10) Patent No.: US 8,430,881 B2
(45) Date of Patent: Apr. 30, 2013

(54) MECHANICAL TISSUE MODIFICATION DEVICES AND METHODS

(75) Inventors: Jeffery L. Bleich, Palo Alto, CA (US); Vahid Saadat, Saratoga, CA (US); Roy Leguidleguid, Union City, CA (US); Jefferey Bleam, Boulder Creek, CA (US)

(73) Assignee: Baxano, Inc., San Jose, CA (US)

( * ) Notice: Subject to any disclaimer, the term of this patent is extended or adjusted under 35 U.S.C. 154(b) by 607 days.

(21) Appl. No.: 11/405,848

(22) Filed: Apr. 17, 2006

(65) Prior Publication Data

US 2007/0213733 A1 Sep. 13, 2007
US 2012/0078253 A9 Mar. 29, 2012

Related U.S. Application Data

(63) Continuation-in-part of application No. 11/375,265, filed on Mar. 13, 2006, now Pat. No. 7,887,538, which is a continuation-in-part of application No. PCT/US2005/037136, filed on Oct. 15, 2005.

(60) Provisional application No. 60/619,306, filed on Oct. 15, 2004, provisional application No. 60/622,865, filed on Oct. 28, 2004, provisional application No. 60/681,719, filed on May 16, 2005, provisional application No. 60/681,864, filed on May 16, 2005, provisional application No. 60/685,190, filed on May 27, 2005.

(51) Int. Cl.
*A61B 17/00* (2006.01)
(52) U.S. Cl.
USPC ............................................. 606/79; 606/84
(58) Field of Classification Search ................ 606/79–85
See application file for complete search history.

(56) References Cited

U.S. PATENT DOCUMENTS

| 184,804 A | 11/1876 | Stohlmann |
| 289,104 A | 11/1883 | How |

(Continued)

FOREIGN PATENT DOCUMENTS

| DE | 32094031 A1 | 9/1983 |
| DE | 40 36 804 A1 | 5/1992 |

(Continued)

OTHER PUBLICATIONS

Tomita, et al. The Threadwire Saw: a New Device for Cutting Bone. Dec. 1996. Journal of Bone and Joint Surgery, Inc. vol. 78-A, No. 12. pp. 1915-1917.*

(Continued)

*Primary Examiner* — Kevin T Truong
*Assistant Examiner* — David Bates
(74) *Attorney, Agent, or Firm* — Shay Glenn LLP

(57) ABSTRACT

A device for modifying one or more tissues in a patient's spine may include: an elongate, at least partially flexible body having a proximal portion and a distal portion, wherein at least the distal portion has dimensions that allow it to be passed into an epidural space and between target and non-target tissues of the spine; at least one movable blade disposed along one side of the elongate body; at least one actuator coupled with the at least one blade and disposed at or near the proximal or distal portion of the body for moving the blade(s) to modify one or more target tissues, wherein the at least one actuator is configured to move the blade(s) without significantly translating the elongate body proximally or distally; and means at or near the proximal and distal portions of the elongate body for facilitating application of at least one of anchoring force and tensioning force to the body to urge the at least one blade against the target tissue.

28 Claims, 53 Drawing Sheets

U.S. PATENT DOCUMENTS

| | | |
|---|---|---|
| 863,389 A | 8/1907 | Harkin |
| 1,039,487 A | 9/1912 | Casebolt |
| 1,201,467 A | 10/1916 | Hoglund |
| 1,374,638 A | 4/1921 | De Cew et al. |
| 1,543,195 A | 6/1925 | Thygesen |
| 1,690,812 A | 11/1928 | Bertels |
| 1,938,200 A | 12/1933 | Wells |
| 2,243,757 A | 5/1941 | Kohls et al. |
| 2,269,749 A | 1/1942 | Wilkie |
| 2,372,553 A | 3/1945 | Coddington |
| 2,437,697 A | 3/1948 | Kalom |
| 2,516,882 A | 8/1950 | Kalom |
| 2,704,064 A | 5/1955 | Fizzell |
| 2,820,281 A | 1/1958 | Amsen |
| 2,843,128 A | 7/1958 | Storz |
| 2,982,005 A | 5/1961 | Booth |
| RE25,582 E | 5/1964 | Davies |
| 3,150,470 A | 9/1964 | Barron |
| 3,200,814 A | 8/1965 | Taylor et al. |
| 3,389,447 A | 6/1968 | Theobald et al. |
| 3,491,776 A | 1/1970 | Fleming |
| 3,495,590 A | 2/1970 | Zeiller |
| 3,528,152 A | 9/1970 | Funakubo et al. |
| 3,624,484 A | 11/1971 | Colyer |
| 3,640,280 A | 2/1972 | Slanker et al. |
| 3,651,844 A | 3/1972 | Barnes |
| 3,664,329 A | 5/1972 | Naylor |
| 3,682,162 A | 8/1972 | Colyer |
| 3,699,729 A | 10/1972 | Garvey et al. |
| 3,752,166 A | 8/1973 | Lyon et al. |
| 3,774,355 A | 11/1973 | Dawson et al. |
| 3,830,226 A | 8/1974 | Staub et al. |
| 3,835,859 A | 9/1974 | Roberts et al. |
| 3,956,858 A | 5/1976 | Catlin et al. |
| 3,957,036 A | 5/1976 | Normann |
| 3,978,862 A | 9/1976 | Morrison |
| 3,999,294 A | 12/1976 | Shoben |
| 4,015,931 A | 4/1977 | Thakur |
| 4,099,519 A | 7/1978 | Warren |
| 4,108,182 A | 8/1978 | Hartman et al. |
| 4,160,320 A | 7/1979 | Wikoff |
| 4,172,440 A | 10/1979 | Schneider et al. |
| 4,203,444 A | 5/1980 | Bonnell et al. |
| 4,207,897 A | 6/1980 | Lloyd et al. |
| 4,259,276 A | 3/1981 | Rawlings |
| 4,405,061 A | 9/1983 | Bergandy |
| D273,806 S | 5/1984 | Bolesky et al. |
| 4,464,836 A | 8/1984 | Hissa |
| 4,502,184 A | 3/1985 | Karubian |
| 4,515,168 A | 5/1985 | Chester et al. |
| 4,518,022 A | 5/1985 | Valdes et al. |
| 4,545,374 A | 10/1985 | Jacobson |
| 4,573,448 A | 3/1986 | Kambin |
| 4,580,545 A | 4/1986 | Dorsten |
| 4,590,949 A | 5/1986 | Pohndorf |
| 4,616,660 A | 10/1986 | Johns |
| 4,621,636 A | 11/1986 | Fogarty |
| 4,625,725 A | 12/1986 | Davison et al. |
| 4,660,571 A | 4/1987 | Hess et al. |
| 4,678,459 A | 7/1987 | Onik et al. |
| 4,690,642 A | 9/1987 | Kyotani |
| 4,700,702 A | 10/1987 | Nilsson |
| 4,709,699 A | 12/1987 | Michael et al. |
| 4,741,343 A | 5/1988 | Bowman |
| 4,750,249 A | 6/1988 | Richardson |
| 4,794,931 A | 1/1989 | Yock |
| 4,808,157 A | 2/1989 | Coombs |
| 4,817,628 A | 4/1989 | Zealear et al. |
| 4,856,193 A | 8/1989 | Grachan |
| 4,867,155 A | 9/1989 | Isaacson |
| 4,872,452 A | 10/1989 | Alexson |
| 4,873,978 A | 10/1989 | Ginsburg |
| 4,883,460 A | 11/1989 | Zanetti |
| 4,894,063 A | 1/1990 | Nashe |
| 4,912,799 A | 4/1990 | Coleman, Jr. |
| RE33,258 E | 7/1990 | Onik et al. |
| 4,943,295 A | 7/1990 | Hartlaub et al. |
| 4,946,462 A | 8/1990 | Watanabe |
| 4,957,117 A | 9/1990 | Wysham |
| 4,962,766 A | 10/1990 | Herzon |
| 4,973,329 A | 11/1990 | Park et al. |
| 4,990,148 A | 2/1991 | Worrick, III et al. |
| 4,994,036 A | 2/1991 | Biscoping et al. |
| 4,994,072 A | 2/1991 | Bhate et al. |
| 4,995,200 A | 2/1991 | Eberhart |
| 5,019,082 A | 5/1991 | Frey et al. |
| 5,025,787 A | 6/1991 | Sutherland et al. |
| 5,026,379 A | 6/1991 | Yoon |
| 5,026,386 A | 6/1991 | Michelson |
| 5,078,137 A | 1/1992 | Edell et al. |
| 5,089,003 A | 2/1992 | Fallin et al. |
| 5,100,424 A | 3/1992 | Jang et al. |
| 5,108,403 A | 4/1992 | Stern |
| 5,125,928 A | 6/1992 | Parins et al. |
| 5,147,364 A | 9/1992 | Comparetto |
| 5,152,749 A | 10/1992 | Giesy et al. |
| 5,161,534 A | 11/1992 | Berthiaume |
| 5,163,939 A | 11/1992 | Winston |
| 5,176,649 A | 1/1993 | Wakabayashi |
| 5,178,145 A | 1/1993 | Rea |
| 5,178,161 A | 1/1993 | Kovacs |
| 5,191,888 A | 3/1993 | Palmer et al. |
| 5,195,507 A | 3/1993 | Bilweis |
| 5,201,704 A | 4/1993 | Ray |
| 5,215,105 A | 6/1993 | Kizelshteyn et al. |
| 5,219,358 A | 6/1993 | Bendel et al. |
| 5,234,435 A | 8/1993 | Seagrave, Jr. |
| 5,242,418 A | 9/1993 | Weinstein |
| 5,250,035 A | 10/1993 | Smith et al. |
| 5,255,691 A | 10/1993 | Otten |
| 5,271,415 A | 12/1993 | Foerster et al. |
| 5,281,218 A | 1/1994 | Imran |
| 5,284,153 A | 2/1994 | Raymond et al. |
| 5,284,154 A | 2/1994 | Raymond et al. |
| 5,300,077 A | 4/1994 | Howell |
| 5,325,868 A | 7/1994 | Kimmelstiel |
| 5,341,807 A | 8/1994 | Nardella |
| 5,351,679 A | 10/1994 | Mayzels et al. |
| 5,353,784 A | 10/1994 | Nady-Mohamed |
| 5,353,789 A | 10/1994 | Schlobohm |
| 5,353,802 A | 10/1994 | Ollmar |
| 5,360,441 A | 11/1994 | Otten |
| 5,365,928 A | 11/1994 | Rhinehart et al. |
| 5,374,261 A | 12/1994 | Yoon |
| 5,383,879 A | 1/1995 | Phillips |
| 5,385,146 A | 1/1995 | Goldreyer |
| 5,387,218 A | 2/1995 | Meswania |
| 5,396,880 A | 3/1995 | Kagan et al. |
| 5,421,348 A | 6/1995 | Larnard |
| 5,423,331 A | 6/1995 | Wysham |
| 5,437,661 A | 8/1995 | Rieser |
| 5,439,464 A | 8/1995 | Shapiro |
| 5,441,044 A | 8/1995 | Tovey et al. |
| 5,441,510 A | 8/1995 | Simpson et al. |
| 5,454,815 A | 10/1995 | Geisser et al. |
| 5,456,254 A | 10/1995 | Pietroski et al. |
| 5,496,325 A | 3/1996 | McLees |
| 5,512,037 A | 4/1996 | Russell et al. |
| 5,515,848 A | 5/1996 | Corbett, III et al. |
| 5,531,749 A | 7/1996 | Michelson |
| 5,534,009 A | 7/1996 | Lander |
| 5,546,958 A | 8/1996 | Thorud et al. |
| 5,554,110 A | 9/1996 | Edwards et al. |
| 5,555,892 A | 9/1996 | Tipton |
| 5,560,372 A | 10/1996 | Cory |
| 5,562,695 A | 10/1996 | Obenchain |
| 5,571,181 A | 11/1996 | Li |
| 5,582,618 A | 12/1996 | Chin et al. |
| 5,598,848 A | 2/1997 | Swanson et al. |
| 5,620,447 A | 4/1997 | Smith et al. |
| 5,630,426 A | 5/1997 | Eggers et al. |
| 5,634,475 A | 6/1997 | Wolvek |
| 5,643,304 A | 7/1997 | Schechter et al. |
| 5,651,373 A | 7/1997 | Mah |
| 5,656,012 A | 8/1997 | Sienkiewicz |
| 5,680,860 A | 10/1997 | Imran |
| 5,681,324 A | 10/1997 | Kammerer et al. |

| | | | | | | |
|---|---|---|---|---|---|---|
| 5,697,889 A | 12/1997 | Slotman et al. | | 6,251,115 B1 | 6/2001 | Williams et al. |
| 5,709,697 A | 1/1998 | Ratcliff et al. | | 6,256,540 B1 | 7/2001 | Panescu et al. |
| 5,725,530 A | 3/1998 | Popken | | 6,259,945 B1 | 7/2001 | Epstein et al. |
| 5,735,792 A | 4/1998 | Vanden Hoek et al. | | 6,261,582 B1 | 7/2001 | Needham et al. |
| 5,755,732 A | 5/1998 | Green et al. | | 6,266,551 B1 | 7/2001 | Osadchy et al. |
| 5,759,159 A | 6/1998 | Masreliez | | 6,266,558 B1 | 7/2001 | Gozani et al. |
| 5,762,629 A | 6/1998 | Kambin | | 6,267,760 B1 | 7/2001 | Swanson |
| 5,766,168 A | 6/1998 | Mantell | | 6,272,367 B1 | 8/2001 | Chance |
| 5,769,865 A | 6/1998 | Kermode et al. | | 6,277,094 B1 | 8/2001 | Schendel |
| 5,775,331 A | 7/1998 | Raymond et al. | | 6,280,447 B1 | 8/2001 | Marino et al. |
| 5,779,642 A | 7/1998 | Nightengale | | 6,292,702 B1 | 9/2001 | King et al. |
| 5,788,653 A | 8/1998 | Lorenzo | | 6,298,256 B1 | 10/2001 | Meyer |
| 5,792,044 A | 8/1998 | Foley et al. | | 6,312,392 B1 | 11/2001 | Herzon |
| 5,795,308 A | 8/1998 | Russin | | 6,324,418 B1 | 11/2001 | Crowley et al. |
| 5,800,350 A | 9/1998 | Coppleson et al. | | 6,324,432 B1 | 11/2001 | Rigaux et al. |
| 5,803,902 A | 9/1998 | Sienkiewicz et al. | | 6,325,764 B1 | 12/2001 | Griffith et al. |
| 5,803,904 A | 9/1998 | Mehdizadeh | | 6,334,068 B1 | 12/2001 | Hacker |
| 5,807,263 A | 9/1998 | Chance | | 6,343,226 B1 | 1/2002 | Sunde et al. |
| 5,810,744 A * | 9/1998 | Chu et al. ................ 600/567 | | 6,358,254 B1 | 3/2002 | Anderson |
| 5,813,405 A | 9/1998 | Montano, Jr. et al. | | 6,360,750 B1 | 3/2002 | Gerber et al. |
| 5,824,040 A | 10/1998 | Cox et al. | | 6,364,886 B1 | 4/2002 | Sklar |
| 5,830,151 A | 11/1998 | Hadzic et al. | | 6,368,324 B1 | 4/2002 | Dinger et al. |
| 5,830,157 A | 11/1998 | Foote | | 6,370,411 B1 | 4/2002 | Osadchy et al. |
| 5,830,188 A | 11/1998 | Abouleish | | 6,370,435 B2 | 4/2002 | Panescu et al. |
| 5,833,692 A | 11/1998 | Cesarini et al. | | 6,383,509 B1 | 5/2002 | Donovan et al. |
| 5,836,948 A | 11/1998 | Zucherman et al. | | 6,390,906 B1 | 5/2002 | Subramanian |
| 5,843,110 A | 12/1998 | Dross et al. | | 6,391,028 B1 | 5/2002 | Fanton et al. |
| 5,846,196 A | 12/1998 | Siekmeyer et al. | | 6,416,505 B1 | 7/2002 | Fleischman et al. |
| 5,846,244 A | 12/1998 | Cripe | | 6,423,071 B1 | 7/2002 | Lawson |
| 5,851,191 A | 12/1998 | Gozani | | 6,423,080 B1 | 7/2002 | Gellman et al. |
| 5,851,209 A | 12/1998 | Kummer et al. | | 6,425,859 B1 | 7/2002 | Foley et al. |
| 5,851,214 A | 12/1998 | Larsen et al. | | 6,425,887 B1 | 7/2002 | McGuckin et al. |
| 5,853,373 A | 12/1998 | Griffith et al. | | 6,436,101 B1 | 8/2002 | Hamada |
| 5,865,844 A | 2/1999 | Plaia et al. | | 6,442,848 B1 | 9/2002 | Dean |
| 5,868,767 A | 2/1999 | Farley et al. | | 6,446,621 B1 | 9/2002 | Svensson |
| 5,879,353 A | 3/1999 | Terry | | 6,451,335 B1 | 9/2002 | Goldenheim et al. |
| 5,885,219 A | 3/1999 | Nightengale | | 6,454,767 B2 | 9/2002 | Alleyne |
| 5,895,417 A | 4/1999 | Pomeranz et al. | | 6,464,682 B1 | 10/2002 | Snoke |
| 5,897,583 A | 4/1999 | Meyer et al. | | 6,466,817 B1 | 10/2002 | Kaula et al. |
| 5,899,909 A | 5/1999 | Claren et al. | | 6,468,289 B1 | 10/2002 | Bonutti |
| 5,904,657 A | 5/1999 | Unsworth et al. | | 6,470,209 B2 | 10/2002 | Snoke |
| 5,916,173 A | 6/1999 | Kirsner | | 6,478,805 B1 * | 11/2002 | Marino et al. ................ 606/170 |
| 5,918,604 A | 7/1999 | Whelan | | 6,487,439 B1 | 11/2002 | Skladnev et al. |
| 5,919,190 A | 7/1999 | VanDusseldorp | | 6,488,636 B2 | 12/2002 | Bryan et al. |
| 5,928,158 A | 7/1999 | Aristides | | 6,491,646 B1 | 12/2002 | Blackledge |
| 5,928,159 A | 7/1999 | Eggers et al. | | 6,500,128 B2 | 12/2002 | Marino |
| 5,941,822 A | 8/1999 | Skladnev et al. | | 6,500,189 B1 | 12/2002 | Lang et al. |
| 5,961,522 A | 10/1999 | Mehdizadeh | | 6,512,958 B1 | 1/2003 | Swoyer et al. |
| 5,972,013 A | 10/1999 | Schmidt | | 6,516,223 B2 | 2/2003 | Hofmann |
| 5,976,110 A | 11/1999 | Greengrass et al. | | 6,520,907 B1 | 2/2003 | Foley et al. |
| 5,976,146 A | 11/1999 | Ogawa et al. | | 6,527,786 B1 | 3/2003 | Davis et al. |
| 6,002,964 A | 12/1999 | Feler et al. | | 6,533,749 B1 | 3/2003 | Mitusina et al. |
| 6,004,326 A | 12/1999 | Castro et al. | | 6,535,759 B1 | 3/2003 | Epstein et al. |
| 6,004,330 A | 12/1999 | Middleman et al. | | 6,540,742 B1 | 4/2003 | Thomas et al. |
| 6,010,493 A | 1/2000 | Snoke | | 6,540,761 B2 | 4/2003 | Houser |
| 6,015,406 A | 1/2000 | Goble et al. | | 6,546,270 B1 | 4/2003 | Goldin et al. |
| 6,022,362 A | 2/2000 | Lee et al. | | 6,558,353 B2 | 5/2003 | Zohmann |
| 6,030,383 A | 2/2000 | Benderev | | 6,562,033 B2 | 5/2003 | Shah et al. |
| 6,030,401 A | 2/2000 | Marino | | 6,564,078 B1 | 5/2003 | Marino et al. |
| 6,038,480 A | 3/2000 | Hrdlicka et al. | | 6,564,079 B1 | 5/2003 | Cory et al. |
| 6,048,345 A | 4/2000 | Berke et al. | | 6,564,088 B1 | 5/2003 | Soller et al. |
| 6,068,642 A | 5/2000 | Johnson et al. | | 6,569,160 B1 | 5/2003 | Goldin et al. |
| 6,073,051 A | 6/2000 | Sharkey et al. | | 6,575,979 B1 | 6/2003 | Cragg |
| 6,099,514 A | 8/2000 | Sharkey et al. | | 6,579,291 B1 | 6/2003 | Keith et al. |
| 6,102,930 A | 8/2000 | Simmons, Jr. | | 6,584,345 B2 | 6/2003 | Govari |
| 6,106,558 A | 8/2000 | Picha | | 6,592,559 B1 | 7/2003 | Pakter et al. |
| 6,113,534 A | 9/2000 | Koros et al. | | 6,595,932 B2 | 7/2003 | Ferrera |
| D432,384 S | 10/2000 | Simons | | 6,597,955 B2 | 7/2003 | Panescu et al. |
| 6,132,387 A | 10/2000 | Gozani et al. | | 6,606,523 B1 | 8/2003 | Jenkins |
| 6,136,014 A | 10/2000 | Sirimanne et al. | | 6,607,530 B1 | 8/2003 | Carl et al. |
| 6,142,993 A | 11/2000 | Whayne et al. | | 6,609,018 B2 | 8/2003 | Cory et al. |
| 6,142,994 A | 11/2000 | Swanson et al. | | 6,610,066 B2 | 8/2003 | Dinger et al. |
| 6,146,380 A | 11/2000 | Racz et al. | | 6,620,129 B2 | 9/2003 | Stecker et al. |
| 6,152,894 A * | 11/2000 | Kubler ................ 604/22 | | 6,622,731 B2 | 9/2003 | Daniel et al. |
| 6,169,916 B1 | 1/2001 | West | | 6,624,510 B1 | 9/2003 | Chan et al. |
| 6,205,360 B1 | 3/2001 | Carter et al. | | 6,626,916 B1 | 9/2003 | Yeung et al. |
| 6,214,001 B1 | 4/2001 | Casscells et al. | | 6,632,184 B1 | 10/2003 | Truwit |
| 6,214,016 B1 | 4/2001 | Williams et al. | | 6,638,233 B2 | 10/2003 | Corvi et al. |
| 6,236,892 B1 | 5/2001 | Feler | | RE38,335 E | 11/2003 | Aust et al. |

| | | | | | | |
|---|---|---|---|---|---|---|
| 6,648,883 | B2 | 11/2003 | Francischelli et al. | 7,169,107 B2 | 1/2007 | Jersey-Willuhn et al. |
| 6,666,874 | B2 | 12/2003 | Heitzmann et al. | 7,189,240 B1 | 3/2007 | Dekel |
| 6,673,063 | B2 | 1/2004 | Brett | 7,198,598 B2 | 4/2007 | Smith et al. |
| 6,673,068 | B1 | 1/2004 | Berube | 7,198,626 B2 | 4/2007 | Lee et al. |
| 6,678,552 | B2 | 1/2004 | Pearlman | 7,207,949 B2 | 4/2007 | Miles et al. |
| 6,682,535 | B2 | 1/2004 | Hoogland | 7,211,082 B2 | 5/2007 | Hall et al |
| 6,682,536 | B2 | 1/2004 | Vardi et al. | 7,214,186 B2 | 5/2007 | Ritland |
| 6,685,709 | B2 | 2/2004 | Sklar | 7,214,197 B2 | 5/2007 | Prass |
| 6,699,246 | B2 | 3/2004 | Zucherman et al. | 7,216,001 B2 | 5/2007 | Hacker et al. |
| 6,723,049 | B2 | 4/2004 | Skladnev et al. | 7,223,278 B2 | 5/2007 | Davison et al. |
| 6,726,531 | B1 | 4/2004 | Harrel | 7,236,832 B2 | 6/2007 | Hemmerling et al. |
| 6,726,685 | B2 | 4/2004 | To et al. | 7,239,911 B2 | 7/2007 | Scholz |
| 6,733,496 | B2 | 5/2004 | Ashley et al. | 7,270,658 B2 | 9/2007 | Woloszko et al. |
| 6,736,815 | B2 | 5/2004 | Ginn | 7,282,061 B2 | 10/2007 | Sharkey et al. |
| 6,736,835 | B2 | 5/2004 | Pellegrino et al. | 7,337,005 B2 | 2/2008 | Kim et al. |
| 6,746,451 | B2 | 6/2004 | Middleton et al. | 7,337,006 B2 | 2/2008 | Kim et al. |
| 6,752,814 | B2 | 6/2004 | Gellman et al. | 7,470,236 B1 | 12/2008 | Kelleher et al. |
| 6,760,616 | B2 | 7/2004 | Hoey et al. | 7,494,473 B2 | 2/2009 | Eggers et al. |
| 6,772,012 | B2 | 8/2004 | Ricart et al. | 7,503,920 B2 | 3/2009 | Siegal |
| 6,776,765 | B2 | 8/2004 | Soukup et al. | 7,507,218 B2 | 3/2009 | Aliski et al. |
| 6,788,966 | B2 | 9/2004 | Kenan et al. | 7,641,658 B2 | 1/2010 | Shaolian et al. |
| 6,790,210 | B1 | 9/2004 | Cragg et al. | 7,655,026 B2 | 2/2010 | Justis et al. |
| 6,805,695 | B2 | 10/2004 | Keith et al. | 7,666,186 B2 | 2/2010 | Harp |
| 6,805,697 | B1 | 10/2004 | Helm et al. | 7,666,209 B2 | 2/2010 | Zucherman et al. |
| 6,807,444 | B2 | 10/2004 | Tu et al. | 7,857,813 B2 | 12/2010 | Schmitz et al. |
| 6,830,561 | B2 | 12/2004 | Jansen et al. | 7,887,538 B2 | 2/2011 | Bleich et al. |
| 6,830,570 | B1 | 12/2004 | Frey et al. | 7,918,849 B2 | 4/2011 | Bleich et al. |
| 6,832,111 | B2 | 12/2004 | Tu et al. | 7,938,830 B2 | 5/2011 | Saadat et al. |
| 6,845,264 | B1 | 1/2005 | Skladnev et al. | 8,192,435 B2 | 6/2012 | Bleich |
| 6,847,849 | B2 | 1/2005 | Mamo et al. | 8,192,436 B2 | 6/2012 | Schmitz |
| 6,851,430 | B2 | 2/2005 | Tsou | 2001/0014806 A1 | 8/2001 | Ellman et al. |
| 6,865,409 | B2 | 3/2005 | Getsla et al. | 2001/0025192 A1 | 9/2001 | Gerber et al. |
| 6,872,204 | B2 | 3/2005 | Houser | 2001/0039419 A1 | 11/2001 | Francischelli et al. |
| 6,875,221 | B2 | 4/2005 | Cull | 2001/0049527 A1 | 12/2001 | Cragg |
| 6,882,879 | B2 | 4/2005 | Rock | 2001/0053885 A1 | 12/2001 | Gielen et al. |
| 6,884,220 | B2 | 4/2005 | Aviv et al. | 2002/0016555 A1 | 2/2002 | Ritchart et al. |
| 6,890,353 | B2 | 5/2005 | Cohn et al. | 2002/0019637 A1 | 2/2002 | Frey et al. |
| 6,895,283 | B2 | 5/2005 | Erickson et al. | 2002/0022788 A1 | 2/2002 | Corvi et al. |
| 6,899,716 | B2 | 5/2005 | Cragg | 2002/0029060 A1 | 3/2002 | Hogendijk |
| 6,907,884 | B2 | 6/2005 | Pellegrino et al. | 2002/0106681 A1 | 8/2002 | Wexler et al. |
| 6,911,003 | B2 | 6/2005 | Anderson et al. | 2002/0138091 A1 | 9/2002 | Pflueger |
| 6,911,016 | B2 | 6/2005 | Balzum et al. | 2002/0165590 A1 | 11/2002 | Crowe et al. |
| 6,916,328 | B2 | 7/2005 | Brett | 2002/0183647 A1 | 12/2002 | Gozani et al. |
| 6,923,813 | B2 | 8/2005 | Phillips et al. | 2003/0023190 A1 | 1/2003 | Cox |
| 6,929,647 | B2 | 8/2005 | Cohen | 2003/0045808 A1 | 3/2003 | Kaula et al. |
| 6,949,104 | B2 | 9/2005 | Griffis et al. | 2003/0074037 A1 | 4/2003 | Moore et al. |
| 6,962,587 | B2 | 11/2005 | Johnson et al. | 2003/0105503 A1 | 6/2003 | Marino |
| 6,971,986 | B2 | 12/2005 | Staskin et al. | 2003/0109871 A1 | 6/2003 | Johnson et al. |
| 6,972,199 | B2 | 12/2005 | Lebouitz et al. | 2003/0113906 A1 | 6/2003 | Sangha et al. |
| 6,973,342 | B1 | 12/2005 | Swanson | 2003/0130655 A1 | 7/2003 | Woloszko et al. |
| 6,976,986 | B2 | 12/2005 | Berube | 2003/0130738 A1 | 7/2003 | Hovda et al. |
| 6,991,643 | B2 | 1/2006 | Saadat | 2003/0167021 A1 | 9/2003 | Shimm |
| 6,994,693 | B2 | 2/2006 | Tal | 2003/0187368 A1 | 10/2003 | Sata et al. |
| 6,997,934 | B2 | 2/2006 | Snow et al. | 2003/0188749 A1 | 10/2003 | Nichols et al. |
| 6,999,820 | B2 | 2/2006 | Jordan | 2003/0208206 A1 | 11/2003 | Gitis et al. |
| 7,001,333 | B2 | 2/2006 | Hamel et al. | 2003/0212400 A1 | 11/2003 | Bloemer et al. |
| 7,008,431 | B2 | 3/2006 | Simonson | 2003/0225412 A1 | 12/2003 | Shiraishi |
| 7,010,352 | B2 | 3/2006 | Hogan | 2003/0225415 A1 | 12/2003 | Richard |
| 7,011,635 | B1 | 3/2006 | Delay | 2004/0006379 A1 | 1/2004 | Brett |
| 7,011,663 | B2 | 3/2006 | Michelson | 2004/0006391 A1 | 1/2004 | Reiley |
| 7,014,616 | B2 | 3/2006 | Ferrera | 2004/0019359 A1 | 1/2004 | Worley et al. |
| 7,033,373 | B2 | 4/2006 | de la Torre et al. | 2004/0024399 A1 | 2/2004 | Sharps et al. |
| 7,041,099 | B2 | 5/2006 | Thomas et al. | 2004/0030330 A1 | 2/2004 | Brassell et al. |
| 7,047,084 | B2 | 5/2006 | Erickson et al. | 2004/0049179 A1 | 3/2004 | Francischelli et al. |
| 7,048,682 | B2 | 5/2006 | Neisz et al. | 2004/0049208 A1 | 3/2004 | Hill et al. |
| 7,050,848 | B2 | 5/2006 | Hoey et al. | 2004/0054368 A1 | 3/2004 | Truckai et al. |
| 7,063,682 | B1 | 6/2006 | Whayne et al. | 2004/0059247 A1 | 3/2004 | Urmey |
| 7,070,556 | B2 | 7/2006 | Anderson et al. | 2004/0064058 A1 | 4/2004 | McKay |
| 7,070,596 | B1 | 7/2006 | Woloszko et al. | 2004/0067000 A1 | 4/2004 | Bates et al. |
| 7,079,883 | B2 | 7/2006 | Marino et al. | 2004/0097927 A1 | 5/2004 | Yeung et al. |
| 7,081,122 | B1 | 7/2006 | Reiley et al. | 2004/0098074 A1 | 5/2004 | Erickson et al. |
| 7,087,053 | B2 | 8/2006 | Vanney | 2004/0102721 A1 | 5/2004 | McKinley |
| 7,087,058 | B2 | 8/2006 | Cragg | 2004/0106940 A1 | 6/2004 | Shaolian et al. |
| 7,107,104 | B2 | 9/2006 | Keravel et al. | 2004/0111084 A1 | 6/2004 | Brett |
| 7,118,576 | B2 | 10/2006 | Gitis et al. | 2004/0116977 A1 | 6/2004 | Finch et al. |
| 7,141,019 | B2 | 11/2006 | Pearlman | 2004/0122433 A1 | 6/2004 | Loubens et al. |
| 7,166,073 | B2 | 1/2007 | Ritland | 2004/0122459 A1 | 6/2004 | Harp |
| 7,166,081 | B2 | 1/2007 | McKinley | 2004/0122482 A1 | 6/2004 | Tung et al. |
| 7,166,107 | B2 | 1/2007 | Anderson | 2004/0127893 A1 | 7/2004 | Hovda |

| | | |
|---|---|---|
| 2004/0127963 A1 | 7/2004 | Uchida et al. |
| 2004/0133208 A1 | 7/2004 | Weikel et al. |
| 2004/0143165 A1 | 7/2004 | Alleyne |
| 2004/0143280 A1 | 7/2004 | Suddaby |
| 2004/0162609 A1 | 8/2004 | Hossainy et al. |
| 2004/0167444 A1 | 8/2004 | Laroya et al. |
| 2004/0167553 A1 | 8/2004 | Simpson et al. |
| 2004/0181150 A1 | 9/2004 | Evans et al. |
| 2004/0199084 A1 | 10/2004 | Kelleher et al. |
| 2004/0199159 A1 | 10/2004 | Lee et al. |
| 2004/0199166 A1 | 10/2004 | Schmieding et al. |
| 2004/0225233 A1 | 11/2004 | Frankowski |
| 2004/0260358 A1 | 12/2004 | Vaughan et al. |
| 2005/0027199 A1 | 2/2005 | Clarke |
| 2005/0033393 A1 | 2/2005 | Daglow |
| 2005/0049592 A1 | 3/2005 | Keith et al. |
| 2005/0060006 A1 | 3/2005 | Pflueger et al. |
| 2005/0075578 A1 | 4/2005 | Gharib et al. |
| 2005/0149034 A1 | 7/2005 | Assell et al. |
| 2005/0149035 A1 | 7/2005 | Pimenta et al. |
| 2005/0149154 A1 | 7/2005 | Cohen et al. |
| 2005/0171587 A1 | 8/2005 | Daglow et al. |
| 2005/0182454 A1 | 8/2005 | Gharib et al. |
| 2005/0187537 A1 | 8/2005 | Loeb et al. |
| 2005/0197661 A1 | 9/2005 | Carrison et al. |
| 2005/0203599 A1 | 9/2005 | Garabedian et al. |
| 2005/0209610 A1 | 9/2005 | Carrison |
| 2005/0209617 A1 | 9/2005 | Koven et al. |
| 2005/0209622 A1 | 9/2005 | Carrison |
| 2005/0216023 A1 | 9/2005 | Aram et al. |
| 2005/0222598 A1 | 10/2005 | Ho et al. |
| 2005/0222647 A1 | 10/2005 | Wahlstrand et al. |
| 2005/0234425 A1 | 10/2005 | Miller et al. |
| 2005/0256423 A1 | 11/2005 | Kirsner |
| 2005/0261692 A1 | 11/2005 | Carrison et al. |
| 2005/0277942 A1 | 12/2005 | Kullas et al. |
| 2005/0283148 A1 | 12/2005 | Janssen et al. |
| 2005/0283204 A1 | 12/2005 | Buhlmann et al. |
| 2006/0004369 A1* | 1/2006 | Patel et al. ................ 606/79 |
| 2006/0015035 A1 | 1/2006 | Rock |
| 2006/0025702 A1 | 2/2006 | Sterrantino et al. |
| 2006/0025703 A1 | 2/2006 | Miles et al. |
| 2006/0025797 A1 | 2/2006 | Lock et al. |
| 2006/0030854 A1 | 2/2006 | Haines |
| 2006/0036211 A1 | 2/2006 | Solsberg et al. |
| 2006/0036271 A1 | 2/2006 | Schomer et al. |
| 2006/0036272 A1 | 2/2006 | Solsberg et al. |
| 2006/0058732 A1 | 3/2006 | Harp |
| 2006/0064101 A1 | 3/2006 | Arramon |
| 2006/0079919 A1 | 4/2006 | Harp |
| 2006/0085048 A1 | 4/2006 | Cory et al. |
| 2006/0085049 A1 | 4/2006 | Cory et al. |
| 2006/0089609 A1 | 4/2006 | Bleich et al. |
| 2006/0089633 A1 | 4/2006 | Bleich et al. |
| 2006/0089640 A1 | 4/2006 | Bleich et al. |
| 2006/0089650 A1 | 4/2006 | Nolde |
| 2006/0089688 A1 | 4/2006 | Panescu |
| 2006/0094976 A1 | 5/2006 | Bleich |
| 2006/0095026 A1 | 5/2006 | Ricart et al. |
| 2006/0095028 A1 | 5/2006 | Bleich |
| 2006/0095059 A1 | 5/2006 | Bleich et al. |
| 2006/0100651 A1 | 5/2006 | Bleich |
| 2006/0122458 A1* | 6/2006 | Bleich ................ 600/101 |
| 2006/0122620 A1 | 6/2006 | Kim |
| 2006/0122653 A1 | 6/2006 | Bradley et al. |
| 2006/0122654 A1 | 6/2006 | Bradley et al. |
| 2006/0135882 A1 | 6/2006 | Bleich |
| 2006/0142753 A1 | 6/2006 | Francischelli et al. |
| 2006/0149278 A1 | 7/2006 | Abdou |
| 2006/0161189 A1 | 7/2006 | Harp |
| 2006/0173374 A1 | 8/2006 | Neubardt et al. |
| 2006/0184175 A1 | 8/2006 | Schomer et al. |
| 2006/0195107 A1 | 8/2006 | Jones et al. |
| 2006/0200153 A1 | 9/2006 | Harp |
| 2006/0200154 A1 | 9/2006 | Harp |
| 2006/0200155 A1 | 9/2006 | Harp |
| 2006/0200219 A1 | 9/2006 | Thrope et al. |
| 2006/0206115 A1 | 9/2006 | Schomer et al. |
| 2006/0206117 A1 | 9/2006 | Harp |
| 2006/0206118 A1 | 9/2006 | Kim et al. |
| 2006/0206178 A1 | 9/2006 | Kim |
| 2006/0224060 A1 | 10/2006 | Garell et al. |
| 2006/0224078 A1 | 10/2006 | Hoey et al. |
| 2006/0235451 A1 | 10/2006 | Schomer et al. |
| 2006/0235452 A1 | 10/2006 | Schomer et al. |
| 2006/0241648 A1 | 10/2006 | Bleich et al. |
| 2006/0258951 A1 | 11/2006 | Bleich et al. |
| 2006/0264952 A1 | 11/2006 | Nelson et al. |
| 2006/0264994 A1 | 11/2006 | Schomer et al. |
| 2006/0276720 A1 | 12/2006 | McGinnis et al. |
| 2006/0276802 A1 | 12/2006 | Vresilovic et al. |
| 2006/0276836 A1 | 12/2006 | Bergin et al. |
| 2007/0010717 A1 | 1/2007 | Cragg |
| 2007/0016097 A1 | 1/2007 | Farquhar et al. |
| 2007/0016185 A1 | 1/2007 | Tullis et al. |
| 2007/0027464 A1 | 2/2007 | Way et al. |
| 2007/0027514 A1 | 2/2007 | Gerber |
| 2007/0049962 A1 | 3/2007 | Marino et al. |
| 2007/0055215 A1 | 3/2007 | Tran et al. |
| 2007/0055262 A1 | 3/2007 | Tomita et al. |
| 2007/0055263 A1 | 3/2007 | Way et al. |
| 2007/0106219 A1 | 5/2007 | Grabinsky |
| 2007/0123888 A1 | 5/2007 | Bleich et al. |
| 2007/0123890 A1 | 5/2007 | Way et al. |
| 2007/0162044 A1 | 7/2007 | Marino |
| 2007/0162061 A1 | 7/2007 | Way et al. |
| 2007/0162062 A1 | 7/2007 | Norton et al. |
| 2007/0166345 A1 | 7/2007 | Pavcnik et al. |
| 2007/0198019 A1 | 8/2007 | Schomer et al. |
| 2007/0213583 A1 | 9/2007 | Kim et al. |
| 2007/0213584 A1 | 9/2007 | Kim et al. |
| 2007/0213734 A1 | 9/2007 | Bleich et al. |
| 2007/0213735 A1 | 9/2007 | Saadat |
| 2007/0213795 A1 | 9/2007 | Bradley et al. |
| 2007/0225703 A1 | 9/2007 | Schmitz et al. |
| 2007/0255162 A1 | 11/2007 | Abboud et al. |
| 2007/0260252 A1 | 11/2007 | Schmitz et al. |
| 2007/0270795 A1 | 11/2007 | Francischelli et al. |
| 2007/0270865 A1 | 11/2007 | Arnin et al. |
| 2008/0033465 A1 | 2/2008 | Schmitz et al. |
| 2008/0051812 A1 | 2/2008 | Schmitz et al. |
| 2008/0058874 A1 | 3/2008 | Westlund et al. |
| 2008/0125621 A1 | 5/2008 | Gellman et al. |
| 2008/0125709 A1 | 5/2008 | Chang et al. |
| 2008/0146867 A1 | 6/2008 | Gellman et al. |
| 2008/0161810 A1 | 7/2008 | Melkent |
| 2008/0197024 A1 | 8/2008 | Simpson et al. |
| 2008/0288005 A1 | 11/2008 | Jackson |
| 2008/0319459 A1 | 12/2008 | Al-najjar |
| 2009/0018610 A1 | 1/2009 | Gharib et al. |
| 2009/0105604 A1 | 4/2009 | Bertagnoli et al. |
| 2009/0138056 A1 | 5/2009 | Anderson et al. |
| 2009/0143829 A1 | 6/2009 | Shluzas |
| 2009/0177112 A1 | 7/2009 | Gharib et al. |
| 2009/0182382 A1 | 7/2009 | Justis et al. |
| 2009/0204119 A1 | 8/2009 | Bleich et al. |
| 2009/0209879 A1 | 8/2009 | Kaula et al. |
| 2010/0010334 A1 | 1/2010 | Bleich et al. |
| 2010/0057087 A1 | 3/2010 | Cha |
| 2010/0094231 A1 | 4/2010 | Bleich et al. |
| 2010/0274250 A1 | 10/2010 | Wallace et al. |
| 2010/0331883 A1 | 12/2010 | Schmitz et al. |
| 2010/0331900 A1 | 12/2010 | Garabedian et al. |
| 2011/0004207 A1 | 1/2011 | Wallace et al. |
| 2011/0046613 A1 | 2/2011 | Schmitz et al. |
| 2011/0060314 A1 | 3/2011 | Wallace et al. |
| 2011/0112539 A1 | 5/2011 | Wallace et al. |
| 2011/0160731 A1 | 6/2011 | Bleich et al. |
| 2011/0160772 A1 | 6/2011 | Arcenio et al. |
| 2011/0190772 A1 | 8/2011 | Saadat |
| 2011/0196257 A1 | 8/2011 | Schmitz et al. |
| 2011/0224709 A1 | 9/2011 | Bleich |
| 2012/0016368 A1 | 1/2012 | Bleich et al. |
| 2012/0022538 A1 | 1/2012 | Schmitz et al. |
| 2012/0065639 A1 | 3/2012 | Schmitz et al. |
| 2012/0078255 A1 | 3/2012 | Bleich et al. |

| | | | |
|---|---|---|---|
| 2012/0095468 | A1 | 4/2012 | Wallace et al. |
| 2012/0123294 | A1 | 5/2012 | Sun et al. |
| 2012/0143206 | A1 | 6/2012 | Wallace et al. |

FOREIGN PATENT DOCUMENTS

| | | |
|---|---|---|
| EP | 359883 A1 | 3/1990 |
| EP | 1304080 A2 | 4/2003 |
| EP | 1340467 A2 | 9/2003 |
| EP | 1207794 B1 | 5/2004 |
| EP | 1315463 B1 | 5/2005 |
| EP | 1611851 A1 | 1/2006 |
| EP | 1006885 B1 | 9/2006 |
| FR | 2706309 | 12/1994 |
| JP | 2960140 B2 | 10/1999 |
| JP | 23116868 | 4/2003 |
| JP | 24065380 A2 | 3/2004 |
| RU | 2107459 | 3/1998 |
| WO | WO92/22259 A2 | 12/1992 |
| WO | WO-96/22057 | 7/1996 |
| WO | WO97/14362 A1 | 4/1997 |
| WO | WO9734536 A2 | 9/1997 |
| WO | WO9918866 A1 | 4/1999 |
| WO | WO-99/21500 A1 | 5/1999 |
| WO | WO-00/67651 A1 | 11/2000 |
| WO | WO 01/08571 A1 | 2/2001 |
| WO | WO01/62168 A2 | 8/2001 |
| WO | WO0207901 A1 | 1/2002 |
| WO | WO0234120 A2 | 5/2002 |
| WO | WO02076311 A2 | 10/2002 |
| WO | WO03/026482 A2 | 4/2003 |
| WO | WO03/066147 A1 | 8/2003 |
| WO | WO2004002331 A1 | 1/2004 |
| WO | WO 2004/028351 A2 | 4/2004 |
| WO | WO2004/043272 A1 | 5/2004 |
| WO | WO2004056267 A1 | 7/2004 |
| WO | WO2004/078066 A2 | 9/2004 |
| WO | WO2004080316 A1 | 9/2004 |
| WO | WO2004096080 A2 | 11/2004 |
| WO | WO-2005/009300 A1 | 2/2005 |
| WO | WO2005057467 A2 | 6/2005 |
| WO | WO 2005/077282 | 8/2005 |
| WO | WO2005089433 A2 | 9/2005 |
| WO | WO2006009705 A2 | 1/2006 |
| WO | WO2006015302 A1 | 2/2006 |
| WO | WO2006017507 A2 | 2/2006 |
| WO | WO2006039279 A2 | 4/2006 |
| WO | WO2006042206 A2 | 4/2006 |
| WO | WO2006044727 A2 | 4/2006 |
| WO | WO2006047598 A1 | 5/2006 |
| WO | WO2006058079 A3 | 6/2006 |
| WO | WO2006058195 A2 | 6/2006 |
| WO | WO2006062555 A2 | 6/2006 |
| WO | WO2006086241 A2 | 8/2006 |
| WO | WO2006099285 A2 | 9/2006 |
| WO | WO2006102085 A2 | 9/2006 |
| WO | WO2007008709 A2 | 1/2007 |
| WO | WO2007021588 A1 | 2/2007 |
| WO | WO2007022194 A2 | 2/2007 |
| WO | WO2007059343 A2 | 2/2007 |
| WO | WO2007067632 A2 | 6/2007 |
| WO | WO2008008898 A2 | 1/2008 |

OTHER PUBLICATIONS

Baumgart et al., "Indikation and Technik der Knochendurchtrennung," Der Chirurg, 1998, vol. 69:1188-1196. (in German with Eng Summary).
Bohinski et al., "Novel use of a threadwire saw for high sacral amputation," Journal of neurosurgery: Spine, 2005, vol. 3, 71R78.
Burrows, Harold, "Surgical instruments and appliances used in operations," Faber and Faber, London, 1937, total pp. 4.
Dammann, Gordon, Pictorial Encyclopedia of Civil War Medical Instruments and Equipment, Pictorial Histories Publishing Company, Missoula, Montana, 1983, Total pp. 2.
Edwards et al; "T-Saw Laminoplasty for the Management of Cervical Spondylotic Myelopathy," SPINE, Lippincott Williams & Wilkins, Inc., 2000, vol. 25 (14): 1788R1794.
Eralp et al., "A comparison of two osteotomy techniques for tibial lengthening," Archives of orthopaedic and trauma surgery, 2004, vol. 124:298R300.
Goel, Atul, "Neurosurgical forum, Supraorbital Craniotomy," Journal of Neurosurgery, 1994, vol. 81, 642-643.
Gore Smoother User Manual, W. L. Gore & Associates, Inc. Flagstaff, AZ, Dec. 1999,Total pp. 3.
Hata et al; "A less invasive surgery for rotator cuff tear: Mini-open repair," Journal of Shoulder and Elbow Surgery, 2001, vol. 10 No. 1, 11-16.
Jun, Byung-Yoon, "Posterior Lumbar Interbody Fusion With Restoration of Lamina and Facet Fusion," SPINE, Lippincott Williams & Wilkins, Inc., 2000, vol. 25 No. 8, 917R922.
Martin-Benlloch et al., "Expansive Laminoplasty as a Method for Managing Cervical Multilevel Spondylotic Myelopathy," Spine, Lippincott Williams & Wilkins, Inc., 2003, vol. 28 No. 7, 680R684.
Miyamoto et al., "Kyphectomy Using a Surgical Threadwire (T-saw) for Kyphotic Deformity in a Child With Myelomeningocele," SPINE, Lippincott Williams & Wilkins, Inc., 2003, vol. 28 No. 10, E187RE190.
Abdel-Wanis et al., "Tumor growth potential after tumoral and instrumental contamination: an in-vivo comparative study of T-saw, Gigli saw, and scalpel," Journal of orthopaedic science, 2001, vol. 6, 424R429.
Mopec Bone-Cutting tool, Product brochure, Total pp. 4.
Nakagiri et al., "Thoracoscopic Rib Resection Using a Gigli Saw," The Annals of Thoracic Surgery, 2005, vol. 80, 755R756.
Osaka et al., "Clinical significance of a wide excision policy for sacrococcygeal chordoma," J Cancer Res Clin Oncol, 2005, Total pp. 6.
Paley et al., "Percutaneous Osteotomies," Orthopedic Clinics of North America, 1991, vol. 22 No. 4, 613-624.
Pancoast, Joseph, "A Treatise on Operative Surgery," Carey and Hart, Philadelphia,1844, Total pp. 11.
Park et al; "Cases of the Excision of Carious Joints," John Scrymgeour, Glasgow, 1806, Total pp. 6.
Peavy et al., "Comparison of Cortical Bone Ablations by Using Infrared Laser Wavelengths 2.9 to 9.2 μm, Lasers in Surgery and Medicine," 1999, vol. 26, 421R434.
Peltier, Leonard Orthopedics: A History and Iconography, Norman Publishing, San Francisco, 1993, Total pp. 3.
Rutkow, Ira, "Surgery an Illustrated History," Mosby'Year Book, Inc., St. Louis, 1993, Total pp. 4.
Schwieger et al., "Abrasive Water Jet Cutting as a New Procedure for Cutting Cancellous Bone'In Vitro Testing in Comparison with the Oscillating Saw," Wiley Interscience, www.interscience,wiley.com, Sep. 20, 2004, 223-228.
Sen, Cengiz, Tibia proksimalinde Gigli testeresi ile yapilanperkütan osteotominin güvenilirligi: Kadavra calismasi, Acta orthopaedica et traumatologica turcica, 2002, vol. 36, 136-140; (in Russian w/ Eng Summary).
Shiraishi et al., "Results of Skip Laminectomy—Minimum 2-Year Follow-up Study Compared With Open-Door Laminoplasty," Spine, Lippincott Williams & Wilkins, Inc., 2003, vol. 28 No. 24, 2667-2672.
Shiraishi T., "A new technique for exposure of the cervical spine laminae," Journal of neurosurgery. Spine, 2002, vol. 96(1), 122-126.
Shiraishi T., Skip laminectomy—a new treatment for cervical spondylotic myelopathy, preserving bilateral muscular attachments to the spinous processes: a preliminary report, Spine, 2002, vol. 2(2), 108-115.
Skippen et al., "The Chain Saw R A Scottish Invention," Scottish Medical Journal, 2004, vol. 49(2), 72-75.
Stevens et al., "Calvarial Bone Graft Harvest Using the Gigli Saw," Journal of Oral and Maxillofacial Surgery, 1998, vol. 56, 798-799.
Takada et al., "Unusual Metastasis to the Cauda Equina From Renal Cell Carcinoma," SPINE, Lippincott Williams & Wilkins, Inc., 2003, vol. 28 No. 6, E114RE117.
Paktiss et al., "Afghan Percutaneous Osteotomy," Journal of Pediatric Orthopaedics, Raven Press Ltd, New York, 1993, vol. 13 No. 4, 531-533.
Tomita et al., "The Threadwire Saw: a New Device for Cutting Bone," The Journal of Bone and Joint Surgery, 1996, vol. 78, 1915-1917.

Truax, Charles, "The Mechanics of Surgery," Chicago, IL; 1899, Total pp. 3.
Wilkins, Robert H, "Neurosurgical Classics," Johnson Reprint Corporation, New York, 1965, 377-382.
Bleich et al; U.S. Appl. No. 11/952,934 entitled "Tissue Removal Devices and Methods," filed Dec. 7, 2007.
Schmitz et al; U.S. Appl. No. 11/468,247 entitled "Tissue access guidewire system and method," filed Aug. 29, 2006.
Schmitz et al; U.S. Appl. No. 11/468,252 entitled "Tissue access guidewire system and method," filed Aug. 29, 2006.
Schmitz et al; U.S. Appl. No. 11/538,345 entitled "Articulating Tissue Cutting Device," filed Oct. 3, 2006.
Schmitz et al; U.S. Appl. No. 11/843,561 entitled "Surgical Probe and Method of Making," filed Aug. 22, 2007.
Schmitz et al; U.S. Appl. No. 11/870,370 entitled "Percutaneous Spinal Stenosis Treatment," filed Oct. 10, 2007.
Schmitz et al; U.S. Appl. No. 12/060,229 entitled "Method, system, and apparatus for neural localization," filed Mar. 31, 2008.
Barer, Malvin, Instrument to Enhance Passage of the Gigli Saw, *Journal of Pediatric Orthopedics*, 1984, vol. 4, pp. 762-763.
Brunori, Andrea, et al., Celebrating the Centennial (1894-1994): Leonardo Gigli and His Wire Saw, *J. Neurosurg*, Jun. 1995, vol. 82, pp. 1086-1090.
Fujita, Takuya, et al., Chordoma in the Cervical Spine Managed With *En Bloc* Excision, *SPINE*, 1999, vol. 24, No. 17, pp. 1848-1851.
Hara, Masahito, et al., *En Bloc* Laminoplasty Performed with Threadwire Saw: Technical Note, *Neurosurgery*, Jan. 2001, vol. 48, No. 1, pp. 235-239.
Honl, Matthias, et al., The Use of Water-Jetting Technology in Prostheses Revision Surgery—First Results of Parameter Studies on Bone and Bone Cement, *Journal of Biomedical Materials Research; Applied Biomaterials*, vol. 53, Issue 6, published online Nov. 20, 2000, pp. 781-790.
Kawahara, Norio, et al., Recapping T-Saw Laminoplasty for Spinal Cord Tumors, *SPINE*, 1999, vol. 24, No. 13, pp. 1363-1370.
Reckling, Frederick W., Modified Stethoscope Earpiece Makes Excellent Gigli Saw Guide, *Orthopaedic Surgery, Department of Surgery*, University of Kansis Medical Center, Kansis City, Dec. 1972, vol. 54-A, No. 8, pp. 1787-1788.
Tomita, K., et al., Total *En Bloc* Spondylectomy and Circumspinal Decompression for Solitary Spinal Metastasis, *International Medical Society of Paraplegia*, 1994, vol. 32, pp. 36-46.
Tomita, K., et al., Total En Bloc Spondylectomy for Solitary Spinal Metastases, *International Orthopaedics*, 1994, vol. 18, pp. 291-298.
Tomita, Katsuro, et al., Expansive Midline T-Saw Laminoplasty (Modified Spinous Process-Splitting) for the Management of Cervical Myelopathy; *SPINE*, 1998, vol. 23, No. 1, p. 32-37.
Tomita et al., "The Use of the T-Saw for Expansive Midline laminoplasty in the Treatment of Cervical Myelopathy," Orthopedics and Traumatology, No. 3, pp. 169-178, 2002.
Bleich, et al.; U.S. Appl. No. 12/127,535 entitled "Guidewire exchange systems to treat spinal stenosis," filed May 27, 2008.
Bleich, et al.; U.S. Appl. No. 12/140,201 entitled "Devices and methods for measuring the space around a nerve root," filed Jun. 16, 2008.
Schmitz et al.; U.S. Appl. No. 12/170,392 entitled "Spinal access system and method," filed Jul. 9, 2008.
Fessler, Richard G., "Minimally Invasive Microendoscopic Decompressive Laminotomy for Lumbar Stenosis" [online], Copyright © 2006 American Association of Neurological Surgeons, Online CME Course, [Retrieved on Jun. 29, 2006], Retrieved from the Internet: <URL: http://www.aans.emedtrain.com/lumbar_stenosis/lumbarStenosis.swf>.
Ellman Int. Disc-FX System Accessories K052241 [online] Retrieved from the internet: <URL: http://www.ellman.com/medical/>.
Codman Laminectomy Shaver (a Johnson & Johnson company www.codman.com) catalogue, pp. 416-431, [online] Retrieved from the internet: <URL: http://www.codman.com/PDFs/Catalog_04_R.pdf>.
Zeppelin Laminectomy Rongeur K901372, [online] Retrieved from the internet: <URL: http://www.zeppelin-medical.com/download/instruments.pdf>.
Integra Ruggles™ Kerrison Rongeurs [online] Retrieved from the internet: <URL: http://www.integra-ls.com/product/?product=22>.
US Surgical Kerrison Spinal Rongeur K943116 [online] Retrieved from the internet: <URL: http://www.ussurg.com/uss/index.html>.
Schmitz et al.; U.S. Appl. No. 12/324,147 entitled "Tissue modification devices," filed Nov. 26, 2008.
Schmitz et al.; U.S. Appl. No. 12/352,385 entitled "Devices, methods and systems for neural localization," filed Jan. 12, 2009.
Bleich et al.; U.S. Appl. No. 12/352,978 entitled "Multiple pathways for spinal nerve rood decompression from a single access point," filed Jan. 13, 2009.
Bleich, Jeffrey; U.S. Appl. No. 12/357,289 entitled "Devices and methods for selective surgical removal of tissue," filed Jan. 21, 2009.
Bleich et al.; U.S. Appl. No. 13/112,918 entitled "Methods, Systems and Devices for Carpal Tunnel Release", filed May 20, 2011.
US Surgical Kerrison Spinal Rongeur K943116 [online] Retrieved from the Internet <URL: http://www.ussurg.com/uss/index.html>. Jul. 27, 1994.
Zeppelin Laminectomy Rongeur K901372, [online] Retrieved from the Internet: <URL: http://www.zeppelin-medical.com/download/instruments.pdf>. Oct. 24, 2006.
Ellman Int. Disc-FX System Accessories K052241 [online] Retrieved from the Internet <URL: http://www.ellman.com/medical/>. Feb. 27, 2006.
Ohta et al., "Superimposed Mechanomygraphic Response at Different Contraction Intensity in Medial Gastrocnemius and Soleus Muscles," International Journal of Sport and Health Science: vol. 5, 63-70, 2007.
Schwieger et al., "Abrasive Water Jet Cutting as a New Procedure for Cutting Cancellous Bone—In Vitro Testing in Comparison with the Oscillating Saw," Wiley Interscience, www.interscience,wiley.com, Sep. 20, 2004, 223-228.
Mopec Bone-Cutting tool, Product brochure, Total pp. 4. First accessed Dec. 15, 2005.
Codman Laminectomy Shaver (a Johnson & Johnson company www.codman.com) catalogue, pp. 416-431, [online] Retrieved from the internet: <URL: http:llwww.codman.com/PDFs/Catalog_04_R.pdf>. First accessed Oct. 24, 2006.
Integra Ruggles TM Kerrison Rongeurs [online] Retrieved from the Internet <URL: http://www.integra-ls.com/products!? product=22>. First accessed Oct. 24, 2006.
Herkowitz, "The Cervical Spine Surgery Atlas", Herkowitz, "*The Cervical Spine Surgery Atlas*", 2004, 2nd Edition Jan. 1, 2004, 203-206, 208.
Schmitz et al.; U.S. Appl. No. 13/267,683 entitled "Flexible Tissue Removal Devices and Methods," filed Oct. 6, 2011.
Wallace et al.; U.S. Appl. No. 13/338,134 entitled "Surgical Tools for Treatment of Spinal Stenosis," filed Dec. 27, 2011.
Bleich et al.; U.S. Appl. No. 13/484,744 entitled "Devices and Methods for Tissue Modification," filed May 31, 2012.
Bleich et al.; U.S. Appl. No. 13/430,500 entitled "Devices and Methods for Tissue Modification," filed Mar. 26, 2012.
Garabedian et al.; U.S. Appl. No. 13/437,214 entitled "Flexible Tissue Rasp," filed Apr. 2, 2012.

* cited by examiner

SECTION A-A

SECTION B-B

SECTION A-A

SECTION B-B

SECTION A-A

SECTION B-B

SECTION C-C

SECTION D-D

SECTION E-E

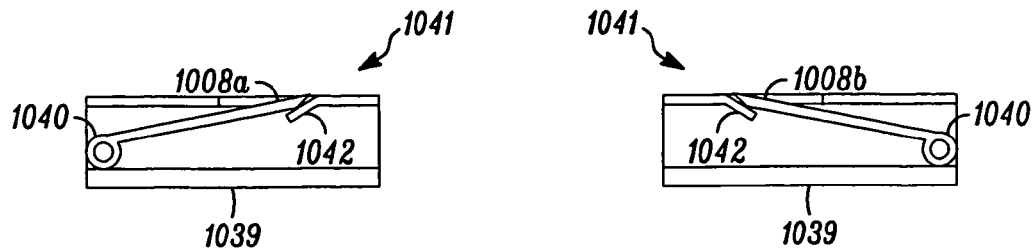
FIG. 22A
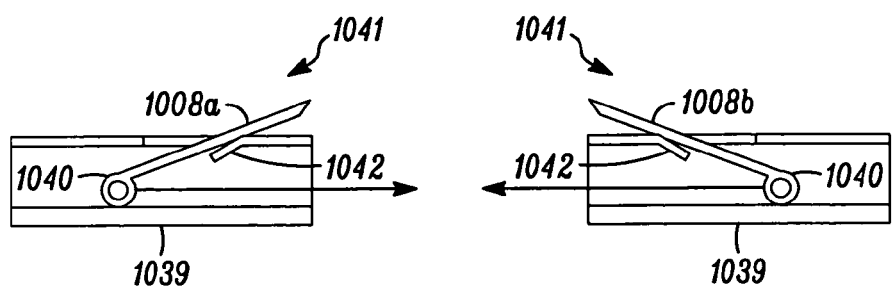
FIG. 22B
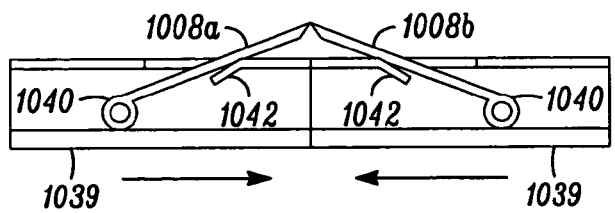
FIG. 22C
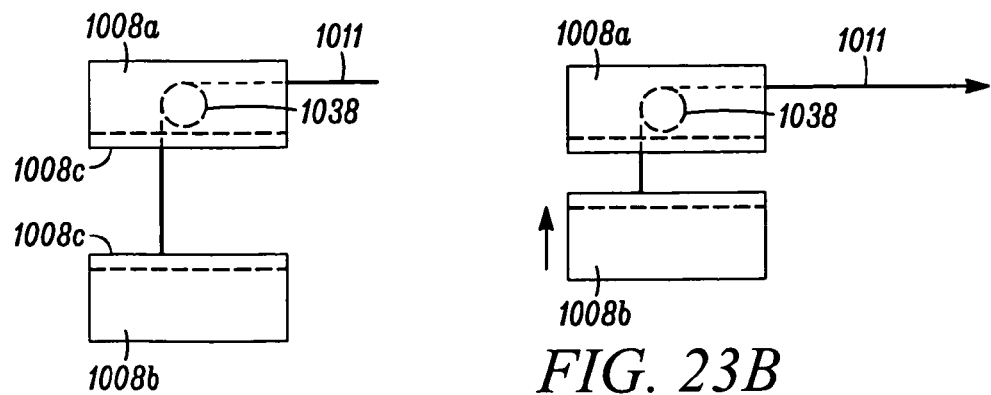
FIG. 23A
FIG. 23B

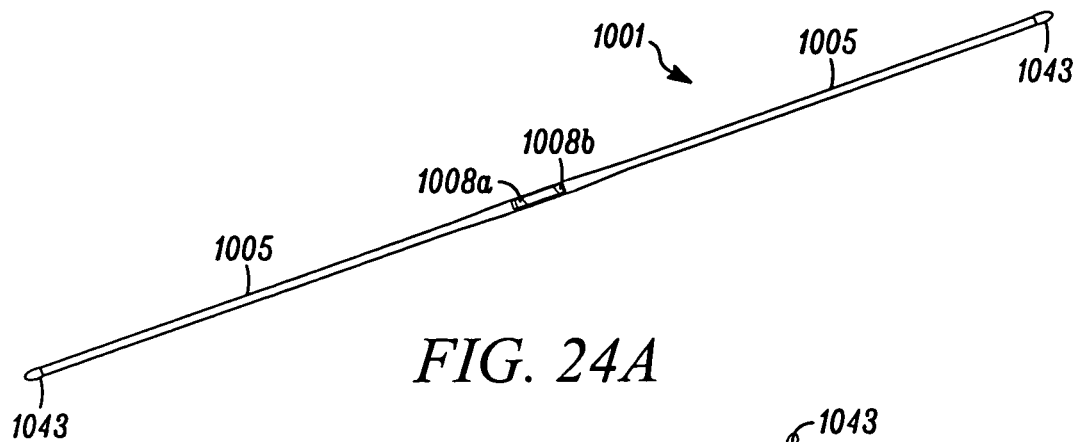
FIG. 24A
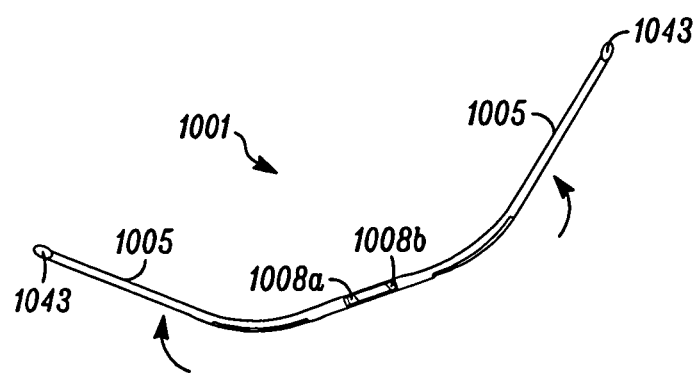
FIG. 24B
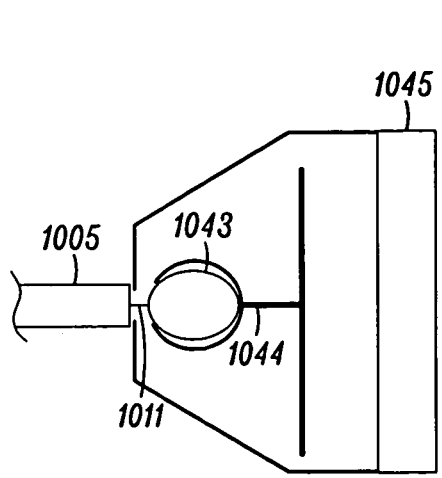 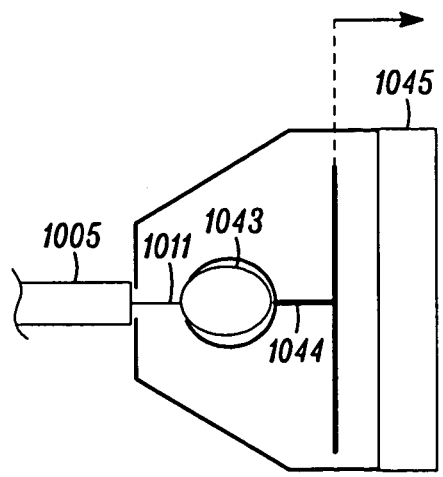
FIG. 25A  FIG. 25B

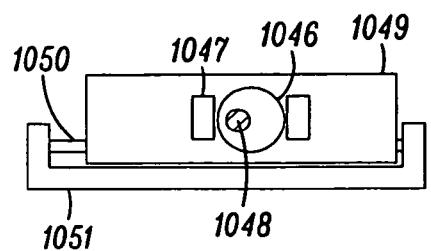
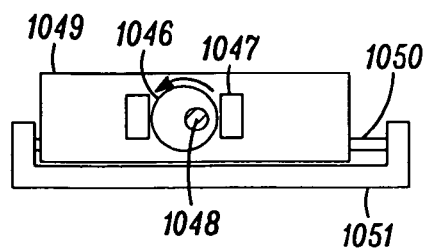
FIG. 26A    FIG. 26B
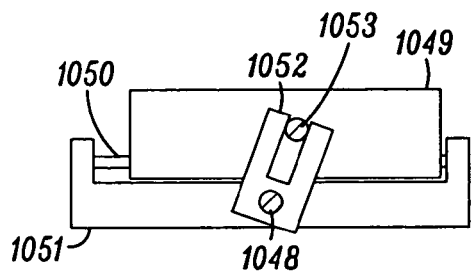
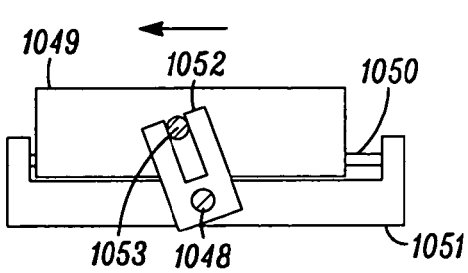
FIG. 27A    FIG. 27B
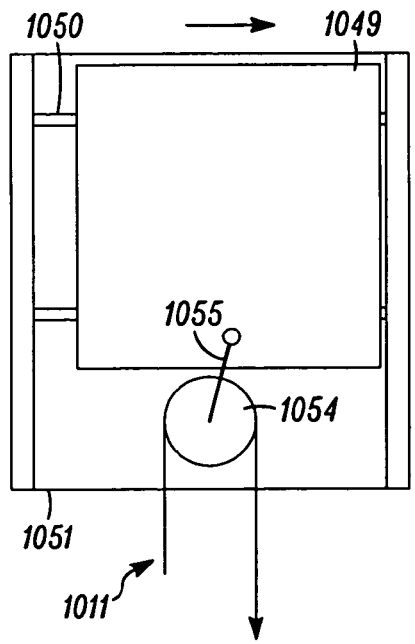
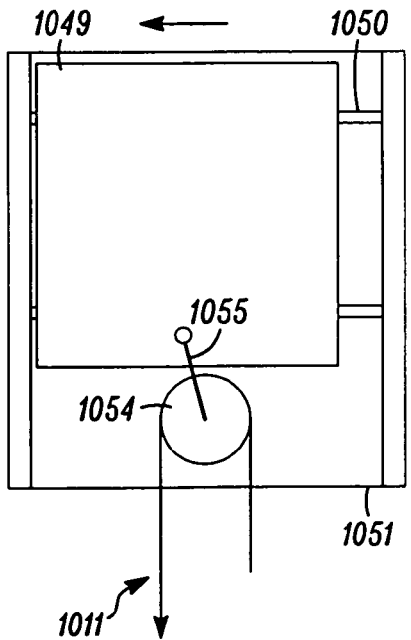
FIG. 28A    FIG. 28B

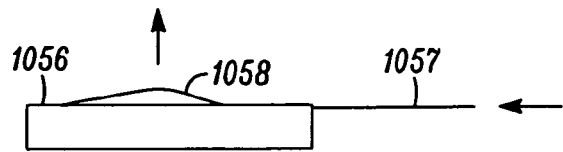
FIG. 29A  FIG. 29B
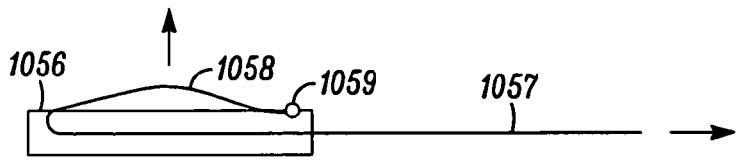
FIG. 29C
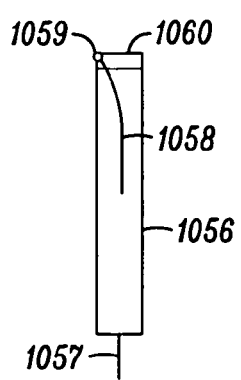 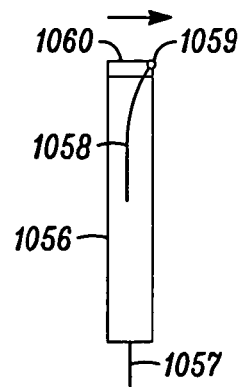
FIG. 30A  FIG. 30B

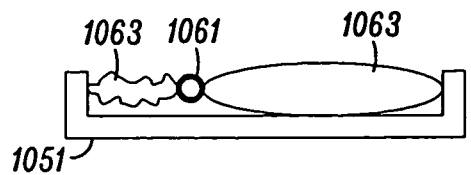
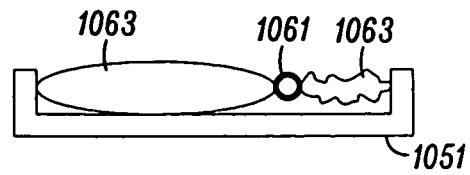
FIG. 34B
FIG. 34C
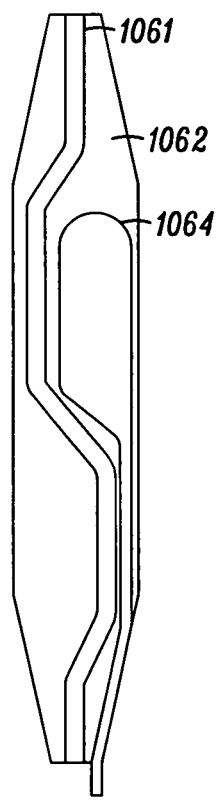
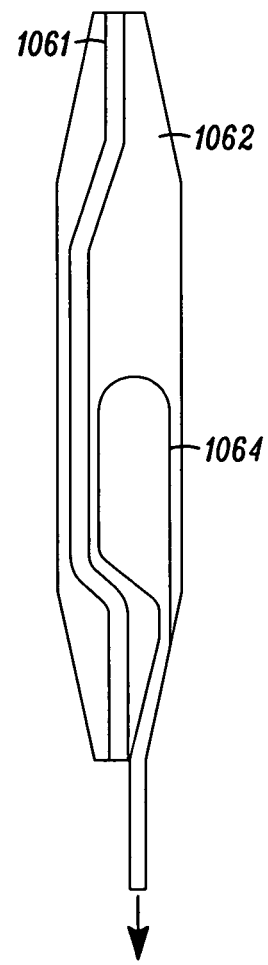
FIG. 35A
FIG. 35B

MECHANICAL TISSUE MODIFICATION DEVICES AND METHODS

CROSS REFERENCE TO RELATED APPLICATIONS

The present application is a continuation-in-part of U.S. patent application Ser. No. 11/375,265, entitled "Methods and Apparatus for Tissue Modification," filed on Mar. 13, 2006, the entire disclosure of which is hereby incorporated by reference, which is a continuation-in-part of PCT Patent Application No. PCT/US2005/037136, filed Oct. 15, 2005, which claimed the benefit of: U.S. Provisional Patent Application No. 60/619,306, filed on Oct. 15, 2004; U.S. Provisional Patent Application No. 60/622,865, filed on Oct. 28, 2004; U.S. Provisional Patent Application No. 60/681,719, filed on May 16, 2005; U.S. Provisional Patent Application No. 60/681,864, filed on May 16, 2005; and U.S. Provisional Patent Application No. 60/685,190, filed on May 27, 2005. PCT Patent Application Pub. No. PCT/US2005/037136, which was incorporated fully by reference in the above-referenced U.S. patent application Ser. No. 11/375,265, is also incorporated fully by reference herein.

BACKGROUND OF THE INVENTION

1. Field of the Invention

The present invention relates to methods and apparatus for modifying tissue in a patient.

Many pathological conditions in the human body may be caused by enlargement, movement, displacement and/or a variety of other changes of bodily tissue, causing the tissue to press against (or "impinge on") one or more otherwise normal tissues or organs. For example, a cancerous tumor may press against an adjacent organ and adversely affect the functioning and/or the health of that organ. In other cases, bony growths (or "bone spurs"), arthritic changes in bone and/or soft tissue, redundant soft tissue, or other hypertrophic bone or soft tissue conditions may impinge on nearby nerve and/or vascular tissues and compromise functioning of one or more nerves, reduce blood flow through a blood vessel, or both. Other examples of tissues which may grow or move to press against adjacent tissues include ligaments, tendons, cysts, cartilage, scar tissue, blood vessels, adipose tissue, tumor, hematoma, and inflammatory tissue.

One specific example of a condition caused by tissue impingement is spinal stenosis. Spinal stenosis occurs when neural tissue and/or vascular tissue in the spine become impinged by one or more structures pressing against them ("neural and/or neurovascular impingement"), causing one or more symptoms. This impingement of tissue may occur in one or more of several different areas in the spine, such as in the central spinal canal (the vertical passage through which the spinal cord and cauda equina extends), the lateral recesses of the spinal canal, or one or more intervertebral foramina (the openings through which nerve roots branching from the spinal cord pass).

For explanatory purposes, FIG. 1 is offered to show an approximate top view of a vertebra (one of the bones of the spinal column) with the cauda equina (the horsetail-shaped bundle of nerves that extends from the base of the spinal cord through the central spinal canal) shown in cross section and two nerve roots exiting the central spinal canal and extending through intervertebral foramina on either side of the vertebra. (FIG. 1 is not drawn to exact scale and is intended for exemplary purposes only. It should be emphasized here that the drawing figures appended to this application are not intended to be precisely anatomically correct and are provided for exemplary purposes to facilitate description.) The spinal cord and cauda equina run vertically along the spine through the central spinal canal, while nerve roots branch off of the spinal cord and cauda equina between adjacent vertebrae and extend through the intervertebral foramina.

One common cause of spinal stenosis is buckling and thickening of the ligamentum flavum (one of the ligaments attached to and connecting the vertebrae), as shown in FIG. 1. Buckling or thickening of the ligamentum flavum may impinge on one or more neurovascular structures, dorsal root ganglia, nerve roots and/or the spinal cord itself. Another common cause of neural and neurovascular compression within the spine is disease of one or more of the intervertebral discs (the malleable discs between adjacent vertebrae), which may lead to collapse, bulging or herniation of the disc. In FIG. 1, an intervertebral disc is shown with three solid-tipped arrows demonstrating how the disc might bulge or herniate into the central spinal canal to impinge upon the spinal cord, cauda equina and/or individual nerve roots. Other causes of neural and neurovascular impingement in the spine include: hypertrophy of one or more facet joints (also known as zygapophysial joints, facet joints provide articulation between adjacent vertebrae—two vertebral facet superior articular processes are shown in FIG. 1); formation of osteophytes (bony growths or "bone spurs") on vertebrae; spondylolisthesis (sliding of one vertebra relative to an adjacent vertebra); and (facet joint) synovial cysts. Disc, bone, ligament or other tissue may impinge on the spinal cord, the cauda equina, branching spinal nerves and/or blood vessels in the spine to cause loss of function, ischemia (shortage of blood supply) and even permanent damage of neural or neurovascular tissue. In a patient, this may manifest as pain, impaired sensation and/or loss of strength or mobility.

In the United States, spinal stenosis occurs with an incidence of between 4% and 6% of adults aged 50 and older and is the most frequent reason cited for back surgery in patients aged 60 and older. Conservative approaches to the treatment of symptoms of spinal stensosis include systemic medications and physical therapy. Epidural steroid injections may also be utilized, but they do not provide long lasting benefits. When these approaches are inadequate, current treatment for spinal stenosis is generally limited to invasive surgical procedures to remove vertebral ligament, cartilage, bone spurs, synovial cysts, cartilage, and bone to provide increased room for neural and neurovascular tissue. The standard surgical procedure for spinal stenosis treatment includes laminectomy (complete removal of the lamina (see FIG. 1) of one or more vertebrae) or laminotomy (partial removal of the lamina), followed by removal (or "resection") of the ligamentum flavum. In addition, the surgery often includes partial or occasionally complete facetectomy (removal of all or part of one or more facet joints between vertebrae). In cases where a bulging intervertebral disc contributes to neural impingement, disc material may be removed surgically in a discectomy procedure.

Removal of vertebral bone, as occurs in laminectomy and facetectomy, often leaves the effected area of the spine very unstable, leading to a need for an additional highly invasive fusion procedure that puts extra demands on the patient's vertebrae and limits the patient's ability to move. In a spinal fusion procedure, the vertebrae are attached together with some kind of support mechanism to prevent them from moving relative to one another and to allow adjacent vertebral bones to fuse together. Unfortunately, a surgical spine fusion results in a loss of ability to move the fused section of the back, diminishing the patient's range of motion and causing stress on the discs and facet joints of adjacent vertebral segments.

While laminectomy, facetectomy, discectomy, and spinal fusion frequently improve symptoms of neural and neurovascular impingement in the short term, these procedures are highly invasive, diminish spinal function, drastically disrupt normal anatomy, and increase long-term morbidity above levels seen in untreated patients.

Therefore, it would be desirable to have less invasive methods and devices for addressing neural and neurovascular impingement in a spine. Ideally, methods and devices for addressing impingement in spine would treat one or more target tissues while preventing unwanted effects on adjacent or nearby non-target tissues. Also ideally, such methods and devices would be minimally invasive and reduce impingement without removing significant amounts of vertebral bone, joint, or other spinal support structures, thereby avoiding the need for spinal fusion and, ideally, reducing the long-term morbidity levels resulting from currently available surgical treatments. It may also be advantageous to have less invasive methods and devices for modifying target tissues in parts of the body other than the spine while preventing modification of non-target tissues. At least some of these objectives will be met by the present invention.

2. Description of Background Art

Flexible wire saws and chain saws, such as threadwire saws (T-saws) and Gigli saws, have been used since the late 1800s to saw through or file/abrade bone and other tissue in the human body. See, for example, Brunori A et al., "Celebrating the Centenial (1894-1994): Leonardo Gigli and His Wire Saw," J Neurosurg 82:1086-1090, 1995. An example of one such saw is described in U.S. Pat. No. 8250, issued to P. A. Stohlmann on Nov. 28, 1876. A description of using a T-saw to cut vertebral bone is provided in Kawahara N et al., "Recapping T-Saw Laminoplasty for Spinal Cord Tumors," SPINE Volume 24, Number 13, pp. 1363-1370.

A method and apparatus for treating spinal stenosis is described in PCT Patent Application Pub. No. WO 01/08571. A surgical instrument for removing cartilage from a knee cavity is described in U.S. Pat. No. 3,835,859.

SUMMARY OF THE INVENTION

In various embodiments, the present invention provides methods, apparatus and systems for modifying tissue in a patient. Generally, the methods, apparatus and systems may involve using an elongate, at least partially flexible tissue modification device having one or more tissue modifying members to modify one or more target tissues. The tissue modification device may be configured such that when the tissue modification member (or members) is in a position for modifying target tissue, one or more sides, surfaces or portions of the tissue modification device configured to avoid or prevent damage to non-target tissue will face non-target tissue. In various embodiments, during a tissue modification procedure, an anchoring force may be applied at or near either a distal portion or a proximal portion of the tissue modification device, either inside or outside the patient. Pulling or tensioning force may also be applied to the unanchored end of the device to urge the tissue modifying member(s) against target tissue. The tissue modifying members may then be activated to modify tissue while being prevented from extending significantly beyond the target tissue in a proximal or distal direction. In some embodiments, the tissue modifying members may be generally disposed along a length of the tissue modification device that approximates a length of target tissue to be modified.

By "applying an anchoring force," it is meant that a force is applied to maintain a portion of a device, or the device as a whole, substantially stable or motion-free. Applying an anchoring force is, therefore, not limited to preventing all movement of a device, and in fact, a device to which an anchoring force is applied may actually move in one or more directions in some embodiments. In other embodiments, an anchoring force is applied to maintain a portion of a device substantially stable, while another portion of the device is allowed to move more freely. As will be described in further detail below, applying an anchoring force in one embodiment involves a user of a device grasping the device at or near one of its ends. In other embodiments, devices may use one or more anchoring members to apply an anchoring force. In a number of embodiments, an anchoring force may be applied with or against one or more tissues of a patient's body, and the tissue(s) may often move even as they apply (or help apply) the force. Thus, again, applying an anchoring force to a device does not necessarily mean that all motion of the device is eliminated. Of course, in some embodiments, it may be possible and desirable to eliminate all movement or substantially all movement of a device (or portion of a device), and in some embodiments anchoring force may be used to do so.

Methods, apparatus and systems of aspects of the present invention generally provide for tissue modification while preventing unwanted modification of, or damage to, surrounding tissues. Tensioning the tissue modification device by applying anchoring force at or near one end and applying tensioning or pulling force at or near the opposite end may enhance the ability of tissue modification members of the device to work effectively within a limited treatment space. Applying tensioning force to a predominantly flexible device may also allow the device to have a relatively small profile, thus facilitating its use in less invasive procedures and in other procedures in which alternative approaches to target tissue may be advantageous.

In some embodiments, the described methods, apparatus and systems may be used to modify tissue in a spine, such as for treating neural impingement, neurovascular impingement and/or spinal stenosis. In alternative embodiments, target tissues in other parts of the body may be modified.

In one aspect of the present invention, a device for modifying one or more tissues in a patient's spine may include: an elongate, at least partially flexible body having a proximal portion and a distal portion, wherein at least the distal portion has dimensions that allow it to be passed into an epidural space and between target and non-target tissues of the spine; at least one movable blade disposed along one side of the elongate body; at least one actuator coupled with the at least one blade and disposed at or near the proximal or distal portion of the body for moving the blade(s) to modify one or more target tissues, wherein the at least one actuator is configured to move the blade(s) without significantly translating the elongate body proximally or distally; and means at or near the proximal and distal portions of the elongate body for facilitating application of at least one of anchoring force and tensioning force to the body to urge the at least one blade against the target tissue.

In another aspect of the present invention, a device for modifying one or more tissues in a patient may include: an elongate, flexible body having a proximal portion and a distal portion; at least one blade disposed along one side of the elongate body; and means at or near the proximal and distal portions of the elongate body for facilitating application of at least one of anchoring force and tensioning force to the body to urge the at least one blade against the target tissue.

In another aspect of the present invention, a method for modifying tissue in a patient may involve: advancing at least a distal portion of at least one elongate, at least partially flexible tissue modification device into a patient and between one or more target tissues and one or more non-target tissues; positioning at least one blade of the tissue modification device adjacent the target tissue such that the blade(s) face the target tissue and do not face the non-target tissue; applying at least one of anchoring and tensioning force to the tissue modification device at or near its proximal and distal portions to urge the blade(s) against the target tissue; and moving the at least one blade to cut the target tissue.

These and other aspects and embodiments are described more fully below in the Detailed Description, with reference to the attached Drawings.

BRIEF DESCRIPTION OF THE DRAWINGS

FIGS. 22A-22C are side views of a blade mechanism including a ramp and a window according to one embodiment of the present invention.

FIGS. 23A and 23B are top views of a blade and pull wire mechanism according to an alternative embodiment of the present invention.

FIGS. 24A and 24B are perspective views of a tissue modification device including flexible portions and endcaps according to one embodiment of the present invention.

FIGS. 25A and 25B are top views of a handle mechanism of a tissue modification device according to one embodiment of the present invention.

FIGS. 26A and 26B are end-on views of a blade mechanism allowing for lateral movement of one or more blades according to one embodiment of the present invention.

FIGS. 27A and 27B are end-on views of a blade mechanism allowing for lateral movement of one or more blades according to an alternative embodiment of the present invention.

FIGS. 28A and 28B are top views of a blade mechanism allowing for lateral movement of one or more blades according to an alternative embodiment of the present invention.

FIGS. 29A-29C are top views of a portion of a tissue modification device including a side wire for facilitating guiding of the portion according to one embodiment of the present invention.

FIGS. 30A and 30B are top views of a portion of a tissue modification device including side wires for facilitating guiding of the portion according to an alternative embodiment of the present invention.

FIGS. 34A-34C are end-on views of a portion of a tissue modification device including expandable bladders for facilitating guiding of the portion according to an alternative embodiment of the present invention.

FIGS. 35A and 35B are top views of a portion of a tissue modification device including a track and deflecting member for facilitating guiding of the portion according to an alternative embodiment of the present invention.

DETAILED DESCRIPTION OF THE INVENTION

Methods, apparatus and systems for modifying tissue in a patient are provided. Although the following description and accompanying drawing figures generally focus on tissue modification in spine, in various alternative embodiments any of a number of tissues in any of a number of anatomical locations in a patient may be modified.

Figure 1:
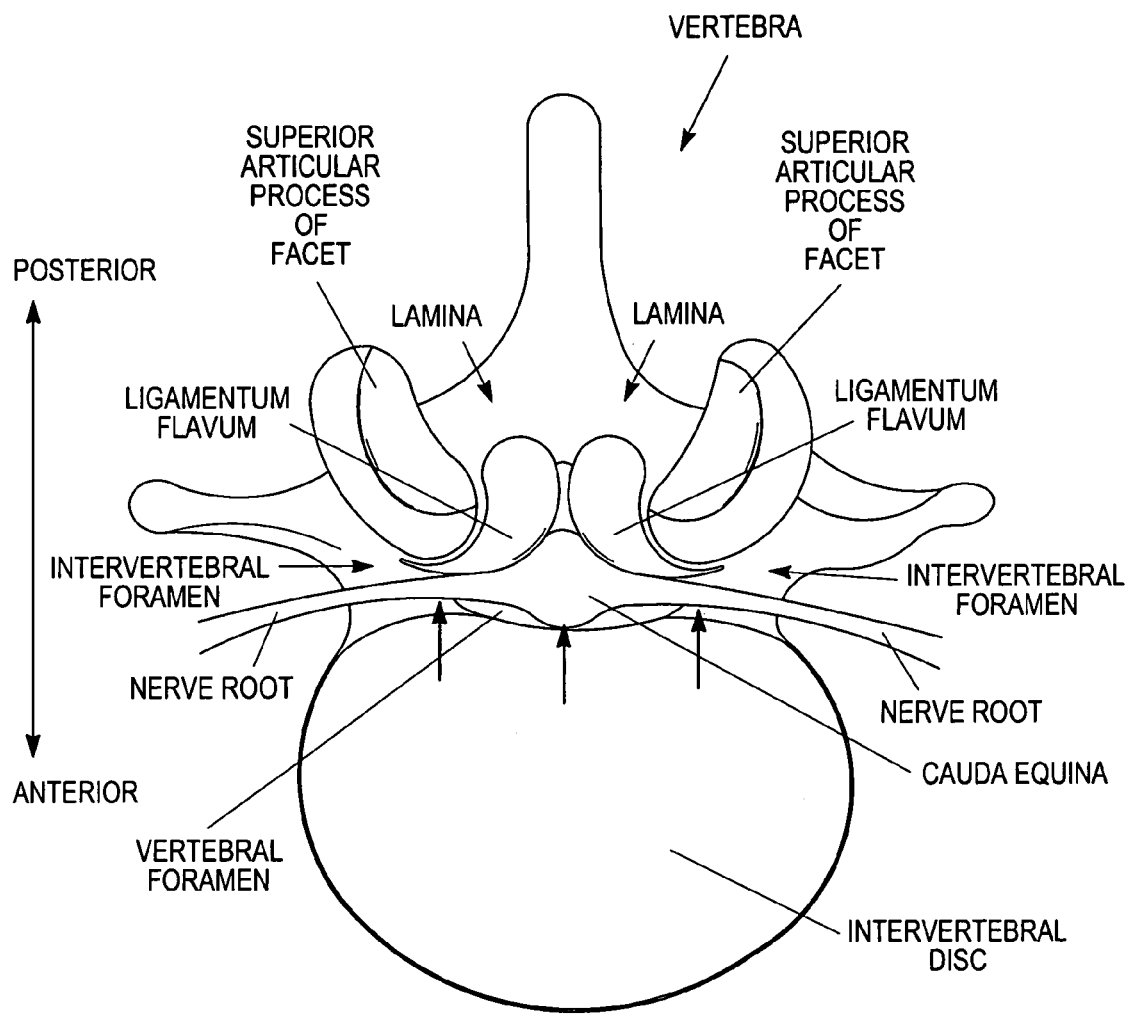
FIG. 1 is cross-sectional view of a spine, showing a top view of a lumbar vertebra, a cross-sectional view of the cauda equina, and two exiting nerve roots.
Figure 2:
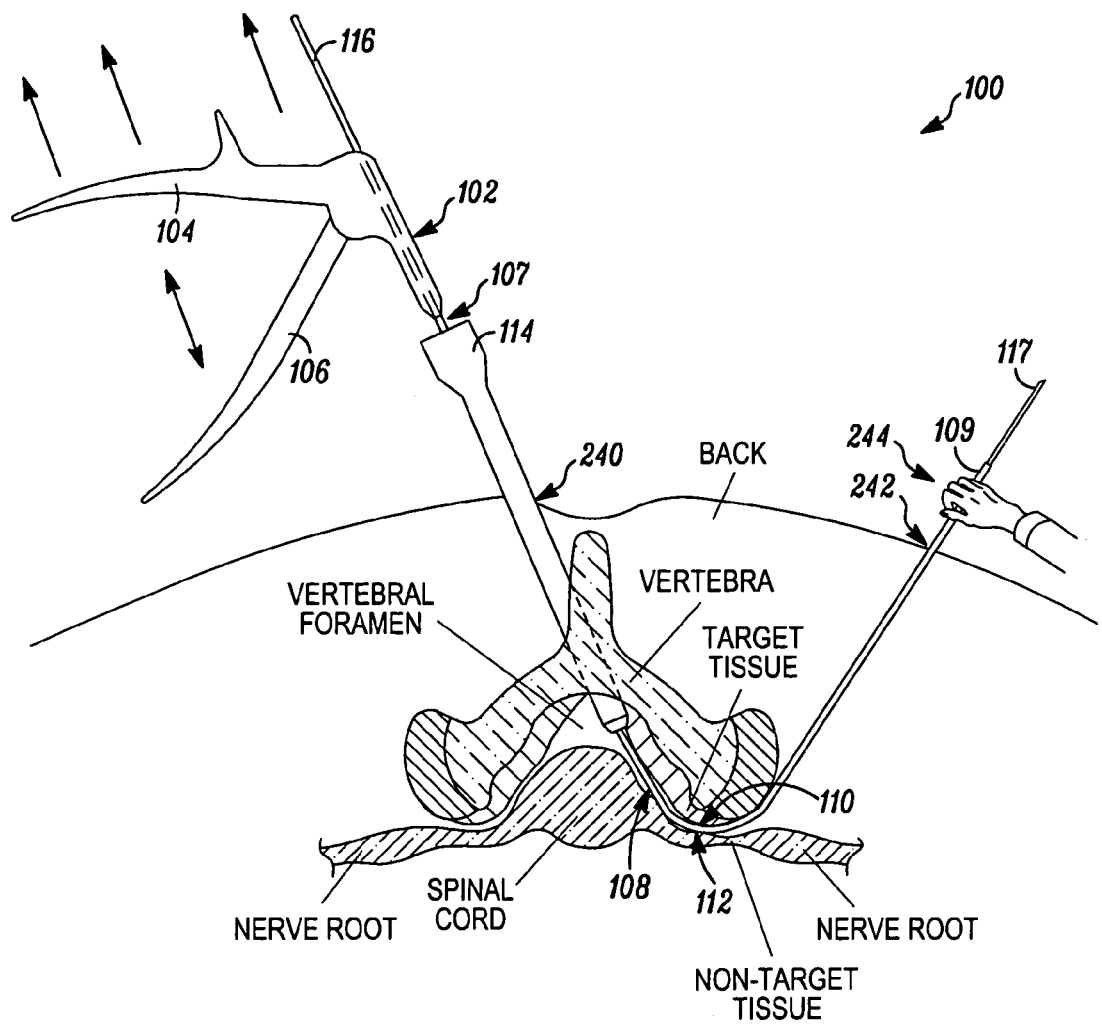
FIG. 2 is a cross-sectional view of a portion of a patient's back and spine, showing part of a vertebra and apparatus in place for modifying tissue according to one embodiment of the present invention.

Referring to FIG. 2, in one embodiment a tissue modification device 102 may include an elongate body 108 having a proximal portion 107 and a distal portion 109, a handle 104 with an actuator 106 coupled with proximal portion 107, one or more tissue modifying members 110, and one or more protective surfaces 112. In various embodiments, some of which are described further below, modification device 102 may be introduced into an area for performing a treatment, such as a spine, using any of a number of different introduction methods, devices and systems 100. In FIG. 2, for example, modification device 102 extends through an introducer device 114 placed through a first incision 240 on the patient's back and into the central spinal canal. Modification device 102 is advanced along a guide member 116, which extends through introducer member 114, through the intervertebral foramen between two adjacent vertebrae (only part of one vertebra is shown in FIG. 2), and out a second (or "distal") incision 242 on the back. In some embodiments, as shown, guide member has a beveled distal tip 117 for facilitating advancement of guide member 116 through tissue.

Generally, tissue modification device 102 may be advanced to a position in the spine such that tissue modifying member 110 faces target tissue to be modified, such as buckled, thickened or otherwise impinging ligamentum flavum tissue as shown in FIG. 2. Modification device 102 is configured such that when tissue modifying member 110 faces the target tissue, protective surface(s) 112 face non-target tissue. Protective surface 112 may be simply a length of elongate body 108 or may have one or more protective features, such as a widened diameter, protective or lubricious coating, extendable barrier, drug-eluting coating or ports, or the like. In some instances, protective surface(s) 112 may act as "non-tissue-modifying" surfaces, in that they may not substantially modify the non-target tissue. In alternative embodiments, protective surface(s) 112 may affect non-target tissue by protecting it in some active way, such as by administering one or more protective drugs, applying one or more forms of energy, providing a physical barrier, or the like.

In some embodiments, once tissue modification device 102 is positioned such that tissue modifying member 110 faces target tissue and protective surface 112 faces non-target tissue, an anchoring force may be applied at or near distal portion 109 of elongate body 108, either inside or outside the patient's body. A tensioning force may also be applied at or near proximal portion 107 of elongate body 108, such as by pulling on handle 104 (one-directional arrows), and actuator 106 may be used (two-headed arrow) to activate tissue modifying member(s) 110 to modify target tissue. In the example shown, anchoring force is applied near distal portion 109 by a user's hand 244, and handle 104 is pulled proximally (arrows) to apply tensioning force. In an alternative embodiment, hand 244 may grasp guide member 116 at or near its distal portion 117 and thus apply anchoring force to it, thus also applying anchoring force to elongate body 108. In one variation of such an embodiment, elongate body 108 or handle 104 may optionally be adjustably clamped to guide member 116 to further enhance or facilitate application of anchoring force to elongate body 108. Tissue modification via tissue modifying members 110 may include cutting, ablating, dissecting, repairing, reducing blood flow in, shrinking, shaving, burring, biting, remodeling, biopsying, debriding, lysing, debulking, sanding, filing, planing, heating, cooling, vaporizing, delivering a drug to, and/or retracting the target tissue. Once tissue has been modified, tissue modification device 102 and any introducer devices 114, guide members 116 or other devices may be removed from the patient.

In various embodiments of the apparatus, tissue modifying member(s) 110 may be disposed along any suitable length of body 108. In one embodiment, for example, such as an embodiment of the device to be used in a spinal treatment, tissue modifying members 110 may be disposed along a length of the device measuring no longer than 10 cm, and preferably no more than 6 cm, and even more preferably no more than 3 cm. In various embodiments, tissue modifying member(s) 110 may include a rongeur, a curette, a scalpel, one or more cutting blades, a scissors, a forceps, a probe, a rasp, a file, an abrasive element, one or more small planes, an electrosurgical device, a bipolar electrode, a unipolar electrode, a thermal electrode, a rotary powered mechanical shaver, a reciprocating powered mechanical shaver, a powered mechanical burr, a laser, an ultrasound crystal, a cryogenic probe, a pressurized water jet, a drug dispensing element, a needle, a needle electrode, or some combination thereof. In various embodiments, all tissue modifying members 110 may be mobile relative to the elongate body, all may be static, or some may be mobile and some may be static. These and other aspects and embodiments are described further below.

Figure 3A:
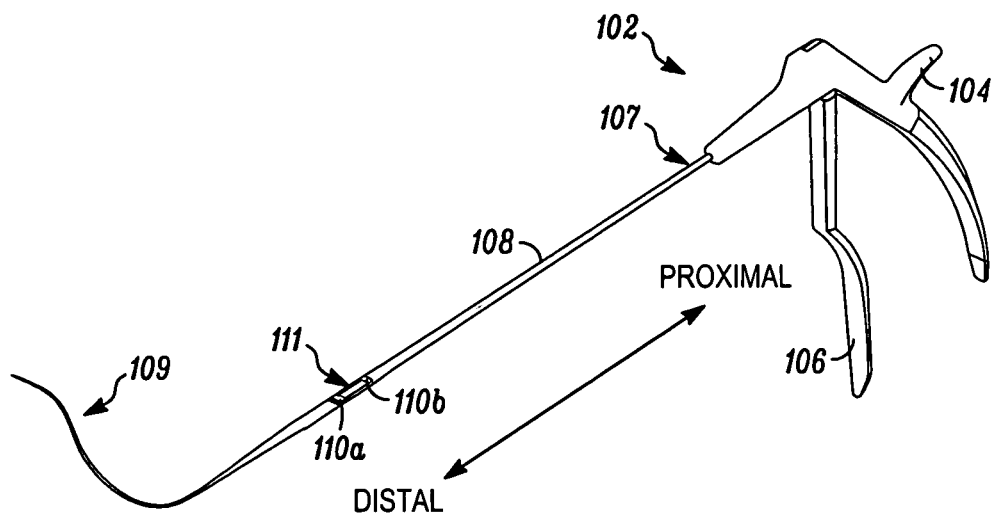
FIG. 3A is a perspective view of a tissue modification device according to one embodiment of the present invention.

Turning now to FIG. 3A-3I, more detailed figures of one embodiment of tissue modification device 102 are shown. Referring to FIG. 3A, tissue modification device 102 may include elongate body 108 having proximal portion 107 and distal portion 109, a window 111 disposed along elongate body 108, two tissue modifying blades 110 exposed through window 111, and handle 104 with actuator 106 coupled with proximal portion 107. In the embodiment shown, the tissue modifying members comprise blades 110, although in alternative embodiments other tissue modifying members may be added or substituted.

In various embodiments, elongate body 108 may have any number of dimensions, shapes, profiles and amounts of flexibility. For example, distal portion 109 is shown having a curved shape to demonstrate that at least a portion of elongate body 108 may be flexible. In various embodiments, elongate body 108 may have one or more of a round, ovoid, ellipsoid, flat, cambered flat, rectangular, square, triangular, symmetric or asymmetric cross-sectional shape. As shown in FIGS. 3C and 3D, in the pictured embodiment, elongate body 108 has a relatively flat configuration, which may facilitate placement of body 108 between target and non-target tissues. Distal portion 109 of body 108 may be tapered, to facilitate its passage into or through narrow spaces as well as through small incisions on a patient's skin. Body 108 may also include a slightly widened portion around the area of window 111 and blades. In one embodiment, such as an embodiment used for modifying tissue in a spine, body 108 may have a small profile, such as having a height of not more than 10 mm at any point along its length and a width of not more than 20 mm at any point along its length, or more preferably a height not more than 5 mm at any point along its length and a width of not more than 10 mm at any point along its length, or even more preferably a height not more than 2 mm at any point along its length and a width of not more than 4 mm at any point along its length. Body 108 may be long enough to extend through a first incision on a patient, between target and non-target tissue, and out a second incision on a patient. Alternatively, body 108 may be long enough to extend through a first incision, between the target and non-target tissue, and to an anchoring location within the patient. In another alternative embodiment, body 108 may be long enough to extend through a first incision, between the target and non-target tissue, to a location nearby but distal to the target tissue within the patient, with some portion of tissue modification device 102 anchored to guide member 116. In some embodiments, elongate body 108 includes at least one feature for allowing passage of the body over a guidewire or other guide member or to allow passage of one or more guide members over or through body 108. For example, in various embodiments body 108 may include one or more guidewire lumens, rails, tracks, lengthwise impressions or some combination thereof.

In one embodiment, elongate body 108 is predominantly flexible along its length and comprises any suitable flexible material, such as thin, flexible metals, plastics, fabrics or the like. In some embodiments, it may be advantageous to include one or more rigid sections in elongate body 108, such as to impart pushability to a portion of body 108 or to facilitate application of force to tissue modification members 110 without causing unwanted bending or kinking of elongate body 108. In such embodiments, rigidity may be conferred by using additional materials in body 108 or by making the rigid portions thicker or wider or of a different shape.

Handle 104 may have any suitable configuration according to various embodiments. Similarly, actuator 106 may include any of a number of actuation devices in various embodiments. In the embodiment shown in FIG. 3A, actuator 106 comprises a trigger or moving handle portion, which is grasped by a user and pulled or squeezed toward handle 164 to bring blades 110 together to cut tissue. In an alternative embodiment, actuator 106 instead may include a switch or button for activating a radiofrequency surgical ablation tissue modifying member. In yet another embodiment, actuator 106 may include a combination trigger and switch, one or more pull wires, any suitable form of lever and/or some combination thereof.

Figure 3B:
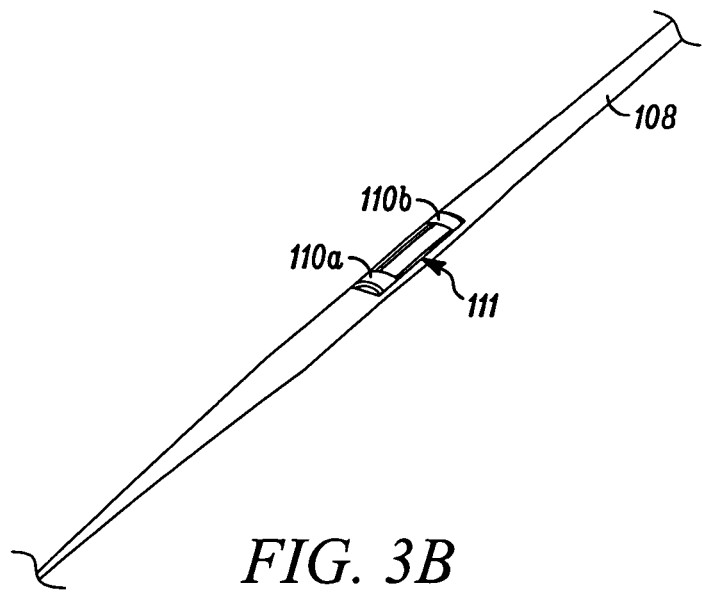
FIG. 3B is a perspective view of a portion of the tissue modification device of FIG. 3A.
Figure 3C:
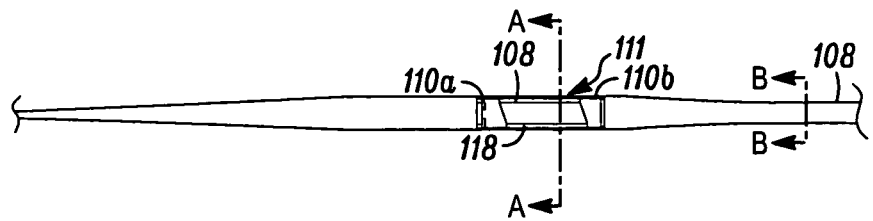
FIG. 3C is a top view of the portion shown in FIG. 3B.
Figure 3D:
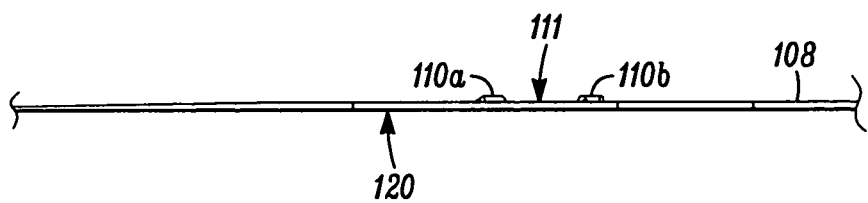
FIG. 3D is a side view of the portion shown in FIGS. 3B and 3C.

FIGS. 3B-3D show in greater detail a portion of tissue modification device 102. In these figures, window 111 and blades 110 are more clearly seen. In one embodiment, at least a portion of elongate body 108 and blades 110 may have a slightly curved configuration. In alternative embodiments, at least a portion of elongate body 108 and blades 110 may be flat. In other alternative embodiments, tissue modification members such as blades 110 may be proud to elongate body 108.

Blades 110 include a distal 110a and a proximal blade 110b that reside at the distal and proximal edges, respectively, of window 111 of elongate body 108. Window 111 of body 108 may accommodate both soft and hard tissue when the device is forcibly applied to the surface of a target tissue site. The top view of the distal portion of elongate body 108, shown in FIG. 3C, depicts the angled edges of distal blade 110a and proximal blade 110b, which facilitate shearing of target tissue. In alternative embodiments, blades 110 may have any of a number of alternative shapes and configurations. The distal portion of body 108 may have a very low profile (height compared to width), as shown in side view FIG. 3D, where only blades 110 protrude from the top surface of the elongate body 108. In one embodiment, also as shown in FIG. 3D, a guidewire tube 120 (or lumen) may extend from (or be coupled with) a lower surface of elongate body 108. The lower surface of elongate body 108 is an example of a protective or non-tissue-modifying surface.

Figure 3E:
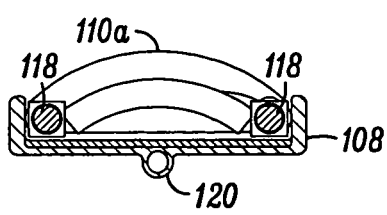
FIGS. 3E and 3F are cross-sectional views of a portion of the tissue modification device taken through lines A-A and B-B, respectively, shown in FIG. 3C.
Figure 3F:
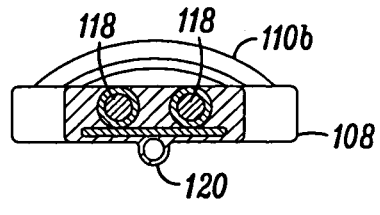

In one embodiment, distal blade 110a is coupled with two pull-wires 118, as seen in FIGS. 3C, 3E and 3F. Pull-wires 118 coupled to and translated by actuator 106 on handle 104 may be used to drive distal blade 110a proximally to contact the cutting edge of proximal blade 110b, thus cutting tissue. Other alternative mechanisms for driving blades 110, such as gears, ribbons or belts, magnets, electrically powered, shape memory alloy, electro magnetic solenoids and/or the like, coupled to suitable actuators, may be used in alternative embodiments. As mentioned, in one embodiment distal blade 110a and/or proximal blade 110b may have an outwardly curvilinear shape along its cutting edge. Alternatively, distal blade 110a may have a different blade shape, including flat, rectilinear, v-shaped, and inwardly curvilinear (concave vs. convex). The cutting edge of either blade 110 may have a sharp edge formed by a simple bevel or chamfer. Alternatively or in addition, a cutting edge may have tooth-like elements that interlock with a cutting edge of an opposing blade, or may have corrugated ridges, serrations, rasp-like features, or the like. In various embodiments, both blades 110 may be of equal sharpness, or alternatively one blade 110 may be sharp and the other substantially flat to provide a surface against which the sharp blade 110 may cut. Alternately or in addition, both cutting edges may be equally hard, or a first cutting edge may be harder than a second, the latter of which deflects under force from the first harder edge to facilitate shearing of the target tissue.

FIGS. 3E and 3F show cross-sectional views through elongate body at lines A-A and B-B, respectively, of FIG. 3C. In some embodiments, all or a portion of elongate body 108, such as the lower surface shown in FIG. 3E, may include a lubricious surface for facilitating manipulation of the tool in the surgical space and at the anatomical site. The lubricious lower surface also provides a barrier between blades 110 and non-target tissue in the surgical space. The lower surface may include a guide member lumen 120 to accommodate a guidewire or other access device or rail. FIG. 3E shows distal blade 110 coupled with pull wires 118. FIG. 3F shows proximal blade 110b, which is not coupled with pull wires 118 but rather fixed to body 108. In various alternative embodiments, proximal blade 110b may be movable distally while distal blade 110a is static, both blades may be moved toward one another, or a different number of blades may be used, such as one blade drawn toward a backstop or more than two blades, one or more of which may be mobile. In various alternative embodiments, guide member lumen 120 may be accommodated on a side surface or more centrally within elongate body 108. In further alternative embodiments, the one or more guide member lumens 120 may comprise one or more various cross sectional shapes, for example substantially round, substantially oval, or substantially rectabular, to accommodate alternative guide members, for example flat or rectangular guidewires, needles or rails. In still other alternative embodiments guide member lumen 120 may be adjustably coupled with the elongate body 108 to enable manipulation of the location of the elongate body 108 and therefore the tissue modifying members 110 relative to the guiding member.

Figure 3G:
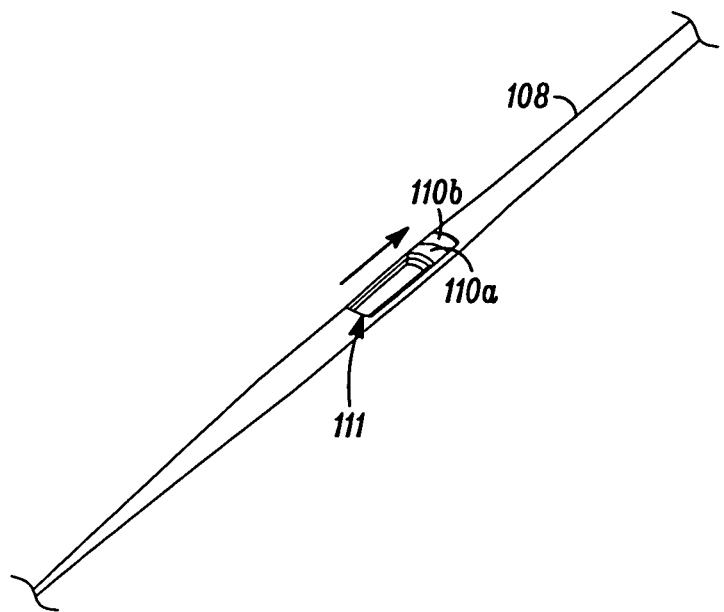
FIG. 3G is a perspective view of a portion of the tissue modification device of FIGS. 3B-3F, shown with a blade of the device in a closed position according to one embodiment of the present invention.
Figure 3H:
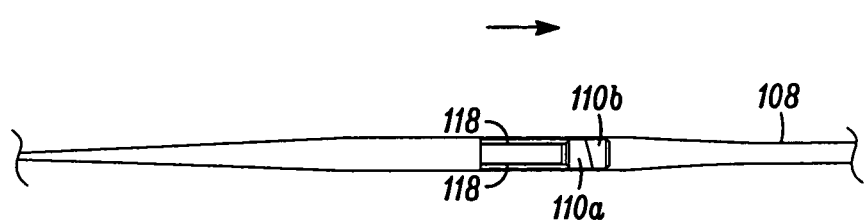
FIG. 3H is a top view of the portion shown in FIG. 3G.
Figure 3I:
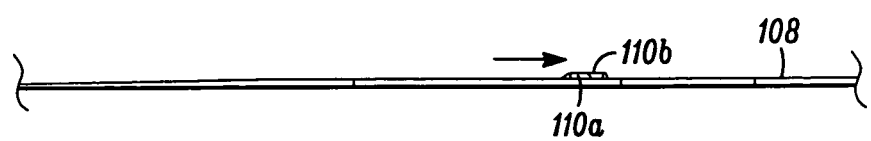
FIG. 3I is a side view of the portion shown in FIGS. 3G and 3H.

Referring now to FIGS. 3G-3I, blades 110 are shown in their closed position. In one embodiment, when distal blade 110a is drawn proximally to cut tissue, at least some of the cut tissue is captured in a hollow interior portion of elongate body 108. Various embodiments may further include a cover, a cut tissue housing portion and/or the like for collecting cut tissue and/or other tissue debris. Such collected tissue and debris may then be removed from the patient during or after a tissue modification procedure. During a given tissue modification procedure, distal blade 110a may be drawn proximally to cut tissue, allowed to retract distally, and drawn proximally again to further cut tissue as many times as desired to achieve a desired amount of tissue cutting.

Blades 110 may be made from any suitable metal, polymer, ceramic, or combination thereof. Suitable metals, for example, may include but are not limited to stainless steel, nickel-titanium alloy, tungsten carbide alloy, or cobalt-chromium alloy, for example, Elgiloy™ (Elgin Specialty Metals, Elgin, Ill., USA), Conichrome™ (Carpenter Technology, Reading, Pa., USA), or Phynox™ (Imphy SA, Paris, France). In some embodiments, materials for the blades or for portions or coatings of the blades may be chosen for their electrically conductive or thermally resistive properties. Suitable polymers include but are not limited to nylon, polyester, Dacron™, polyethylene, acetal, Delrin™ (DuPont, Wilmington, Del.), polycarbonate, nylon, polyetheretherketone (PEEK), and polyetherketoneketone (PEKK). In some embodiments, polymers may be glass-filled to add strength and stiffness. Ceramics may include but are not limited to aluminas, zirconias, and carbides. In various embodiments, blades 110 may be manufactured using metal injection molding (MIM), CNC machining, injection molding, grinding and/or the like. Pull wires 118 be made from metal or polymer and may have circular, oval, rectangular, square or braided cross-sections. In some embodiments, a diameter of a pull wire 118 may range from about 0.001"-0.050", and more preferably from about 0.010"-0.020".

Depending on the tissue to be treated or modified, activating blades 110 (or other tissue modifying members in alternative embodiments) may cause them to modify target tissue along an area having any of a number of suitable lengths. In use, it may also be advantageous to limit the extent of action of blades 110 or other tissue modifying members to a desired length of tissue, thus not allowing blades 110 to affect tissue beyond that length. In so limiting the effect of blades, unwanted modification of, or damage to, surrounding tissues and structures may be limited or even eliminated. In one embodiment, for example, where the tissue modification device is used to modify tissue in a spine, blades 110 may operate along a length of target tissue of no more than 10 cm, and preferably no more than 6 cm, and even more preferably no more than 3 cm. Of course, in other parts of the body and to address other tissues, different tissue modification devices may be used and tissue modifying members may have many different lengths of activity. In one embodiment, to facilitate proper location of tissue modifying members, such as blades 110, relative to target tissue, the tissue modifying members and/or the elongate body and/or one or more additional features intended for just such a purpose may be composed of a material readily identifiable via x-ray, fluoroscopic, magnetic resonance or ultrasound imaging techniques.

In various embodiments, a number of different techniques may be used to prevent blades 110 (or other tissue modifying members) from extending significantly beyond the target tissue. In one embodiment, for example, preventing blades 110 from extending significantly beyond the target tissue involves holding tissue modification device 102 as a whole predominantly stable to prevent device 102 from translating in a direction toward its proximal portion or toward its distal portion while activating blades 110. Holding device 102 stable is achieved by anchoring one end of the device and applying tensioning force at or near the other end, as described further below.

In the embodiment shown in FIGS. 3A-3I, pull wires 118 are retracted proximally by squeezing actuator 106 proximally. In an alternative embodiment, squeezing actuator 106 may cause both blades 110 to translate inward so that they meet approximately in the middle of window 111. In a further embodiment, distal blade 110a may be returned to it's starting position by a pulling force generated from the distal end of device 102, for example by using a distal actuator that is attached to distal wires, or by pulling on the distal guide member which is attached to distal blade 110a. In yet another alternative embodiment, proximal blade 110b may be moved to cut by a pulling force generated from the distal end of device 102, for example by using a distal actuator that is attached to distal wires, or by pulling on the distal guide member which is attached to proximal blade 110b. In yet another embodiment, squeezing actuator 106 may cause proximal blade 110b to move distally while distal blade 110a stays fixed. In other alternative embodiments, one or more blades 110 may move side-to-side, one or more blades 110 may pop, slide or bow up out of window 111 when activated, or one or more blades 110 may expand through window. In another embodiment, one or more blades 110 and/or other tissue modifying members of device 102 may be powered devices configured to cut, shave, grind, abrade and/or resect target tissue. In other embodiments, one or more blades may be coupled with an energy transmission device, such as a radiofrequency (RF) or thermal resistive device, to provide energy to blade(s) 110 for cutting, ablating, shrinking, dissecting, coagulating or heating and thus enhancing tissue modification. In another embodiment, a rasp or file may be used in conjunction with or coupled with one or more blades. In any of these embodiments, use of actuator 106 and one or more moving blades 110 provides for tissue modification with relatively little overall translation or other movement of tissue modification device 102. Thus, target tissue may be modified without extending blades 110 or other tissue modification members significantly beyond an area of target tissue to be treated.

Figure 4A:
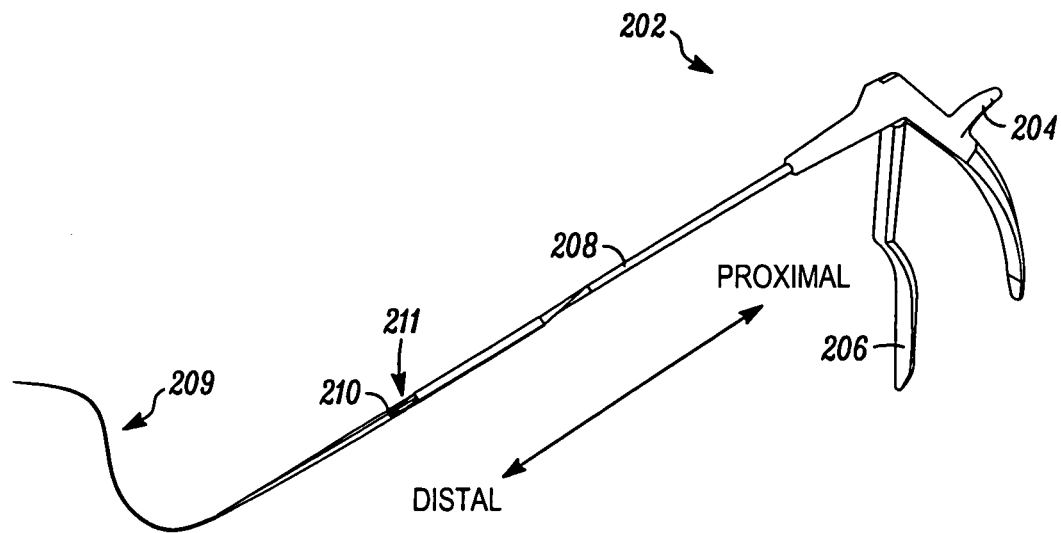
FIG. 4A is a perspective view of a tissue modification device according to one embodiment of the present invention.
Figure 4B:
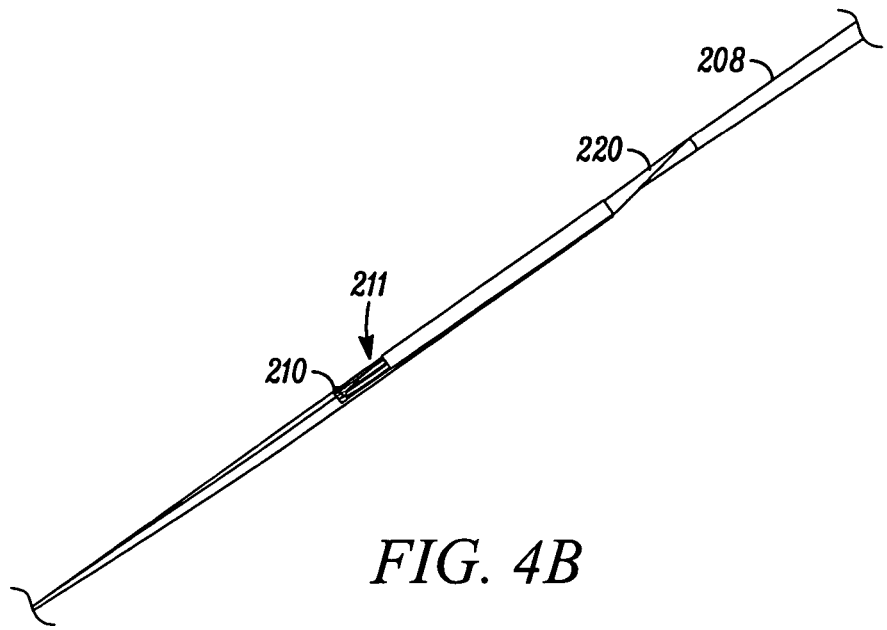
FIG. 4B is a perspective view of a portion of the tissue modification device of FIG. 4A.
Figure 4C:
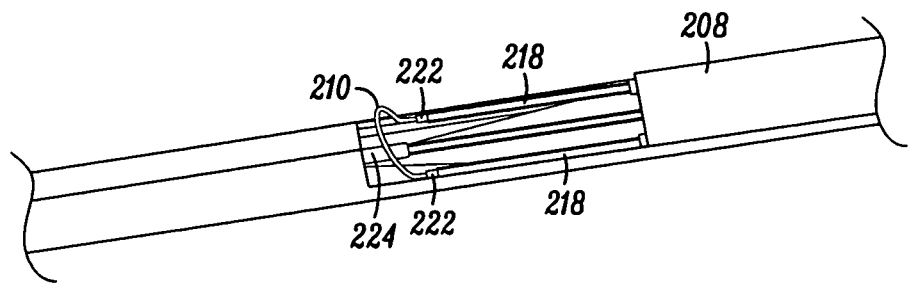
FIG. 4C is a close-up, perspective view of a portion of the tissue modification device of FIGS. 4A and 4B, showing a tissue modifying member according to one embodiment of the present invention.

Referring now to FIGS. 4A-4C, in an alternative embodiment, a tissue modification device 202 may include an elongate body 208 having a proximal portion and a distal portion 209, a handle 204 and actuator 206 coupled with proximal portion, and a window 211 and tissue modifying member 210 disposed near distal portion 209. As seen more clearly in FIGS. 4B and 4C, in the embodiment shown, tissue modifying member 210 comprises an RF electrode wire loop. Wire loop 210 may comprise any suitable RF electrode, such as those commonly used and known in the electrosurgical arts, and may be powered by an internal or external RF generator, such as the RF generators provided by Gyrus Medical, Inc. (Maple Grove, Minn.). Any of a number of different ranges of radio frequency may be used, according to various embodiments. For example, some embodiments may use RF energy in a range of between about 70 hertz and about 5 megahertz. In some embodiments, the power range for RF energy may be between about 0.5 Watts and about 200 Watts. Additionally, in various embodiments, RF current may be delivered directly into conductive tissue or may be delivered to a conductive medium, such as saline or Lactate Ringers solution, which may in some embodiments be heated or vaporized or converted to plasma that in turn modifies target tissue. Distal portion 209 includes a tapered tip, similar to that described above, to facilitate passage of elongate body 208 into narrow anatomical sites. Handle 204 and actuator 206 are similar to those described above, although in the embodiment of FIGS. 4A-4C, actuator 206 may be used to change the diameter of the wire loop 210. Using actuator 206, wire loop 210 may be caused to extend out of window 211, expand, retract, translate and/or the like. Some embodiments may optionally include a second actuator (not shown), such as a foot switch for activating an RF generator to delivery RF current to an electrode.

Elongate body 208 may be fabricated from any suitable material and have any of a number of configurations. In one embodiment, body 208 comprises a metal tube with a full-thickness slit (to unfold the tube into a flat form--not shown) or stiffening element (not shown). The split tube provides for a simple manufacturing process as well as a conductive pathway for bi-polar RF operation. The tube may include a waist region 220.

Referring to FIG. 4C, insulators 222 may be disposed around a portion of wire loop 210 so that only a desired portion of wire loop 210 may transfer RF current into the tissue for tissue modifying capability. Wire loop 210, covered with insulators 222 may extend proximally into support tubes 218. In various alternative embodiments, an electrode tissue modifying member (of which wire loop 210 is but one example) may be bipolar or monopolar. For example, as shown in FIG. 4C, a sleeve 224 housed toward the distal portion of window 211 may act as a return electrode for wire loop 210 in a bipolar device. Wire loop electrodes 210 may be made from various conductive metals such as stainless steel alloys, nickel titanium alloys, titanium alloys, tungsten alloys and the like. Insulators 222 may be made from a thermally and electrically stable polymer, such as polyimide, polyetheretherketone (PEEK), polytetrafluoroethylene (PTFE), polyamide-imide, or the like, and may optionally be fiber reinforced or contain a braid for additional stiffness and strength. In alternative embodiments, insulators 222 may be composed of a ceramic-based material.

In one embodiment, wire loop 210 may be housed within elongate body 208 during delivery of tissue modification device 202 into a patient, and then caused to extend up out of window 211, relative to the rest of body 208, to remove tissue. Wire loop 210 may also be flexible so that it may pop or bow up out of window 211 and may deflect when it encounters hard tissue surfaces. Wire loop 210 may have any of a number of shapes, such as curved, flat, spiral or ridged. Wire loop 210 may have a diameter similar to the width of body 208, while in alternative embodiments it may expand when extended out of window 211 to have a smaller or larger diameter than that of body 208. Pull wires (not shown) may be retracted proximally, in a manner similar to that described above, in order to collapse wire loop 210, decrease the diameter and lower the profile of the wire loop 210, and/or pull wire loop 210 proximally to remove tissue or be housed within body 208. The low profile of the collapsed wire loop 210, facilitates insertion and removal of tissue modification device 202 prior to and after tissue modification. As the wire loop 210 diameter is reduced, support tubes 218 deflect toward the center of elongate body 208.

In an alternative embodiment (not shown), tissue modification device 202 may include multiple RF wire loops 210 or other RF members. In another embodiment, device 202 may include one or more blades as well as RF wire loop 210. In such an embodiment, wire loop 210 may be used to remove or otherwise modify soft tissues, such as ligamentum flavum, or to provide hemostasis, and blades may be used to modify hard tissues, such as bone. In other embodiments, as described further below, two separate tissue modification devices (or more than two devices) may be used in one procedure to modify different types of tissue, enhance modification of one type of tissue or the like.

In other alternative embodiments, tissue modification devices 202 may include tissue modifying members such as a rongeur, a curette, a scalpel, a scissors, a forceps, a probe, a rasp, a file, an abrasive element, one or more small planes, a rotary powered mechanical shaver, a reciprocating powered mechanical shaver, a powered mechanical burr, a laser, an ultrasound crystal a cryogenic probe, a pressurized water jet, a drug dispensing element, a needle, a needle electrode, or some combination thereof. In some embodiments, for example, it may be advantageous to have one or more tissue modifying members that stabilize target tissue, such as by grasping the tissue or using tissue restraints such as barbs, hooks, compressive members or the like. In one embodiment, soft tissue may be stabilized by applying a contained, low-temperature substance (for example, in the cryo-range of temperatures) that hardens the tissue, thus facilitating resection of the tissue by a blade, rasp or other device. In another embodiment, one or more stiffening substances or members may be applied to tissue, such as bioabsorbable rods.

Figure 5A:
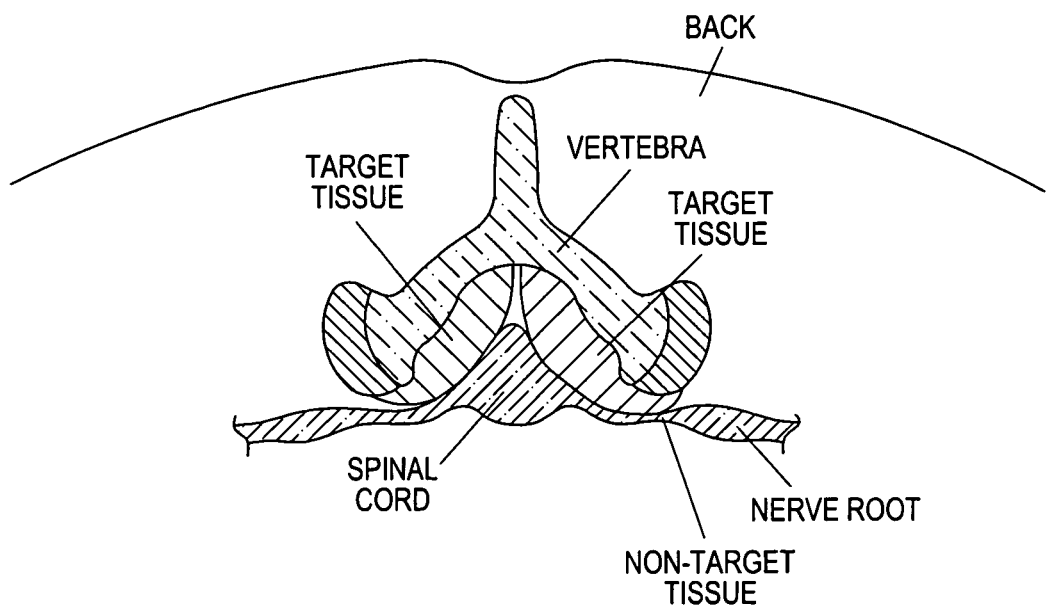
FIGS. 5A-5D are cross-sectional views of a spine and demonstrate a method for using a tissue modification device according to one embodiment of the present invention.

Referring now to FIGS. 5A-5D, one embodiment of a method for modifying tissue in a spine is demonstrated in simplified, diagrammatic, cross-sectional views of a portion of a patient's back and spine. FIG. 5A shows a portion of the patient's back in cross section, with a portion of a vertebra, the spinal cord with branching nerve roots, and target tissue, which in this illustration is the ligamentum flavum and possibly a portion of the facet capsule. The target tissue is typically impinging directly on one or more of the group including nerve roots, neurovascular structures, dorsal root ganglia, cauda equina, or individual nerves.

Figure 5B:
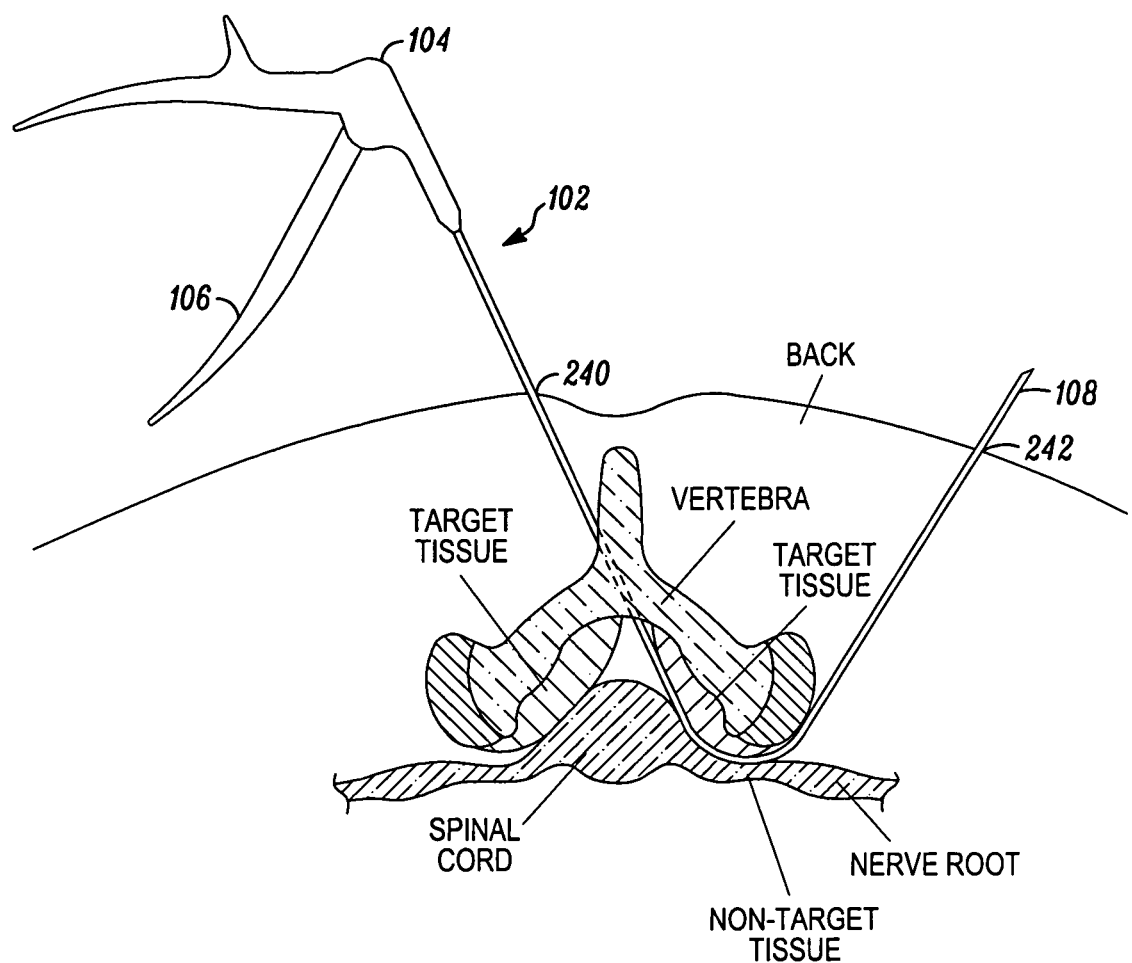

In FIG. 5B, tissue modification device 102 has been positioned in the patient's back to perform a tissue modification procedure. Various methods, devices and systems for introducing device 102 into the patient and advancing it to the position for modifying tissue are described in further detail below. Generally, device 102 may be positioned via a percutaneous or open surgical procedure, according to various embodiments. In one embodiment, device 102 may be inserted into the patient through a first incision 240, advanced into the spine and between target tissue and non-target tissue (such as spinal cord, nerve roots, nerves and/or neurovascular tissue), and further advanced so a distal portion of elongate body 108 exits a second (or distal) incision 242 to reside outside the patient. In positioning device 102, one or more tissue modifying members (not shown) are positioned to face the target tissue, while one or more protective portions of elongate body 108 face non-target tissue.

Figure 5C:
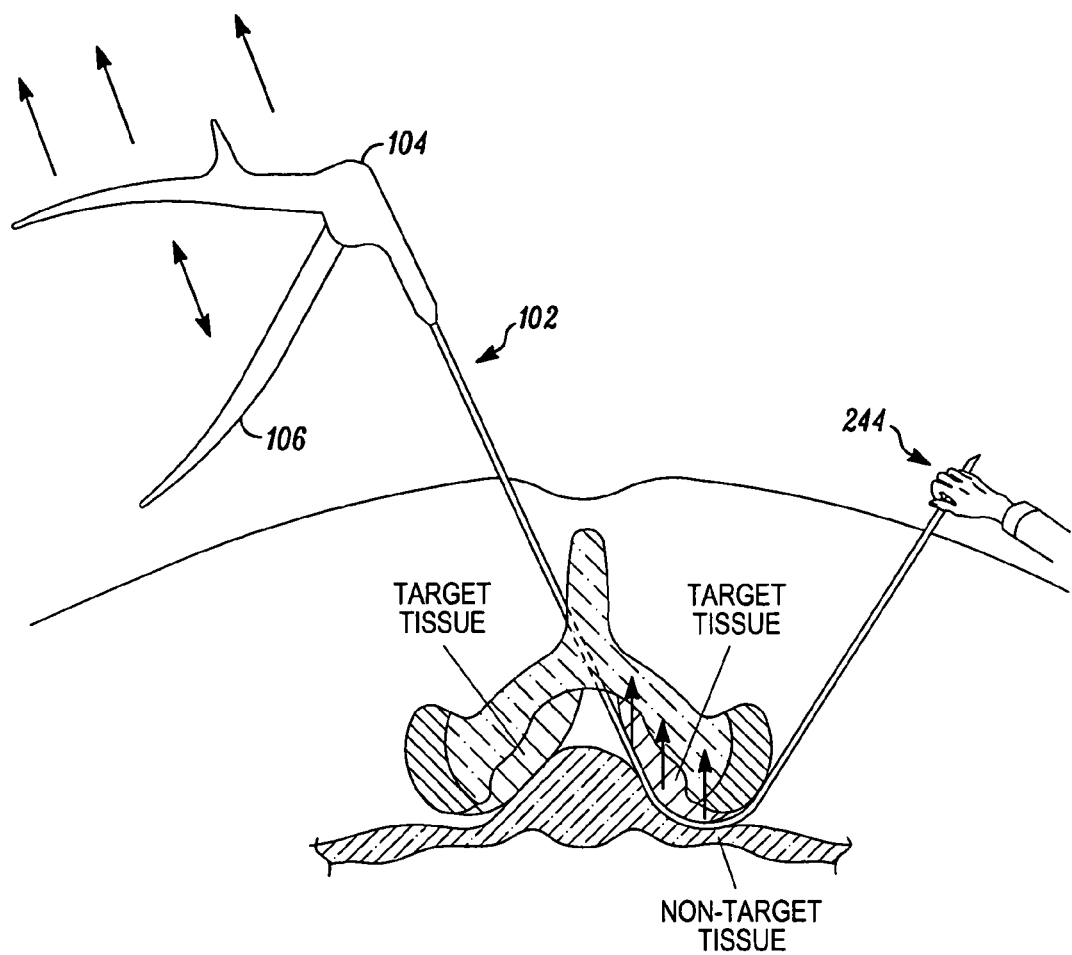

Referring to FIG. 5C, once device 102 is positioned in a desired location, anchoring force may be applied at or near the distal portion of elongate body 108. In one embodiment, applying anchoring force involves a user 244 grasping body 108 at or near its distal portion. In alternative embodiments, as described further below, anchoring force may be applied by deploying one or more anchor members disposed at or near the distal portion of body 108, or by grasping a guidewire or other guide member extending through at least part of body 108. Once the anchoring force is applied, proximally-directed tensioning force may be applied to device 102, such as by pulling proximally on handle 104 (one-directional, diagonal arrows). This tensioning force, when applied to the substantially anchored device 102, may help urge the tissue modifying member(s) against the target tissue (one-directional, vertical arrows near target tissue), thus enhancing contact with the target tissue and facilitating its modification. With the tissue modifying member(s) contacting the target tissue, actuator 106 may be squeezed or pulled (two-headed arrow) to cause the tissue modifying member(s) to modify tissue. (Alternative actuators may be activated in different ways in alternative embodiments.)

In various alternative embodiments, certain of the above-described steps may be carried out in different order. For example, in one embodiment the distal portion of elongate body 108 may be anchored within or outside the patient before the tissue modifying members are positioned adjacent the target tissue. In another alternative embodiment, the proximal portion of device 102 may be anchored, and the tensioning force may be applied to the distal portion of device 102. In yet another embodiment, tensioning force may be applied to both ends of the device. In yet another embodiment, a second handle and actuator may be coupled with the distal end of body 108 after it exits the patient's back, allowing tensioning forces as well as tissue modifying actuation to occur at both the proximal and distal portions of device 102. By anchoring one end of device 102 and applying tensioning force to the opposite end, contact of the tissue modifying members with the target tissue is enhanced, thus reducing or eliminating the need for translating or otherwise moving device 102 as a whole and reducing the overall profile and the resulting access pathway required to position the device. Reducing movement and profile of device 102 and using tissue modifying members confined to a relatively small area of device 102 helps facilitate target tissue modification while minimizing or eliminating damage to surrounding tissues or structures.

As mentioned above, tissue may be modified using one tissue modification device or multiple devices, according to various embodiments. In one embodiment, for example, an RF electrosurgical tissue modification device may be used in the patient to remove soft tissue such as ligament, and a bladed tissue modification device such as a rongeur may then be used to remove additional soft tissue, calcified soft tissue, or hard tissue such as bone. In some embodiments, such multiple devices may be inserted, used and removed serially, while in alternative embodiments such devices may be inserted into the patient at the same time to be used in combination.

Figure 5D:
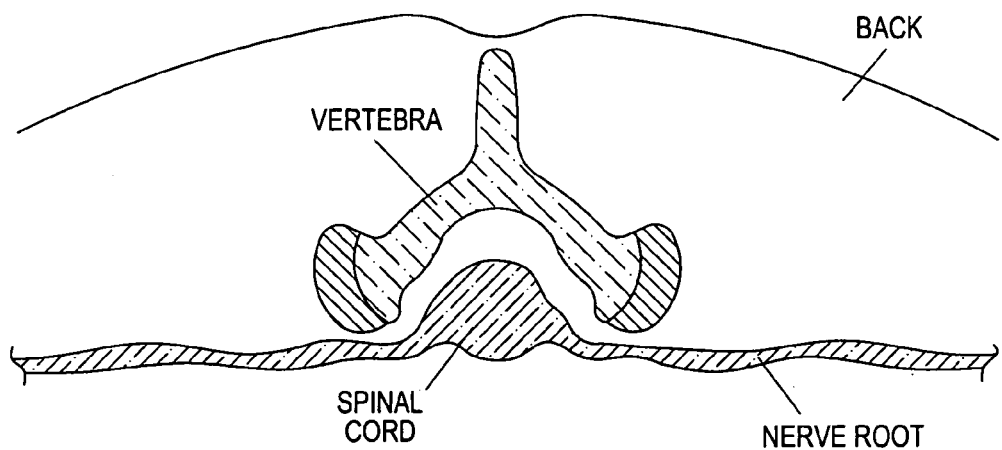

Referring to FIG. 5D, using one or more tissue modification devices 102, a desired amount of target tissue may be removed from more than one area in the spine. FIGS. 5A-5C demonstrate removal of target tissue on one side of the spine, and that method or a similar method may also be used to remove target tissue on an opposite side of the spine, as shown in FIG. 5D, where target tissue has been removed from both sides. That the desired amount of tissue has been removed may be confirmed by tactile feedback from the device or from a separate device, by testing nerve conduction through one or more previously impinged nerves, by testing blood flow through one or more previously impinged blood vessels, by passing (independently or over the guide member) a measurement probe or sound through the treated portion, through one or more radiographic tests, through some combination thereof, or by any other reasonable means.

Figure 6A:
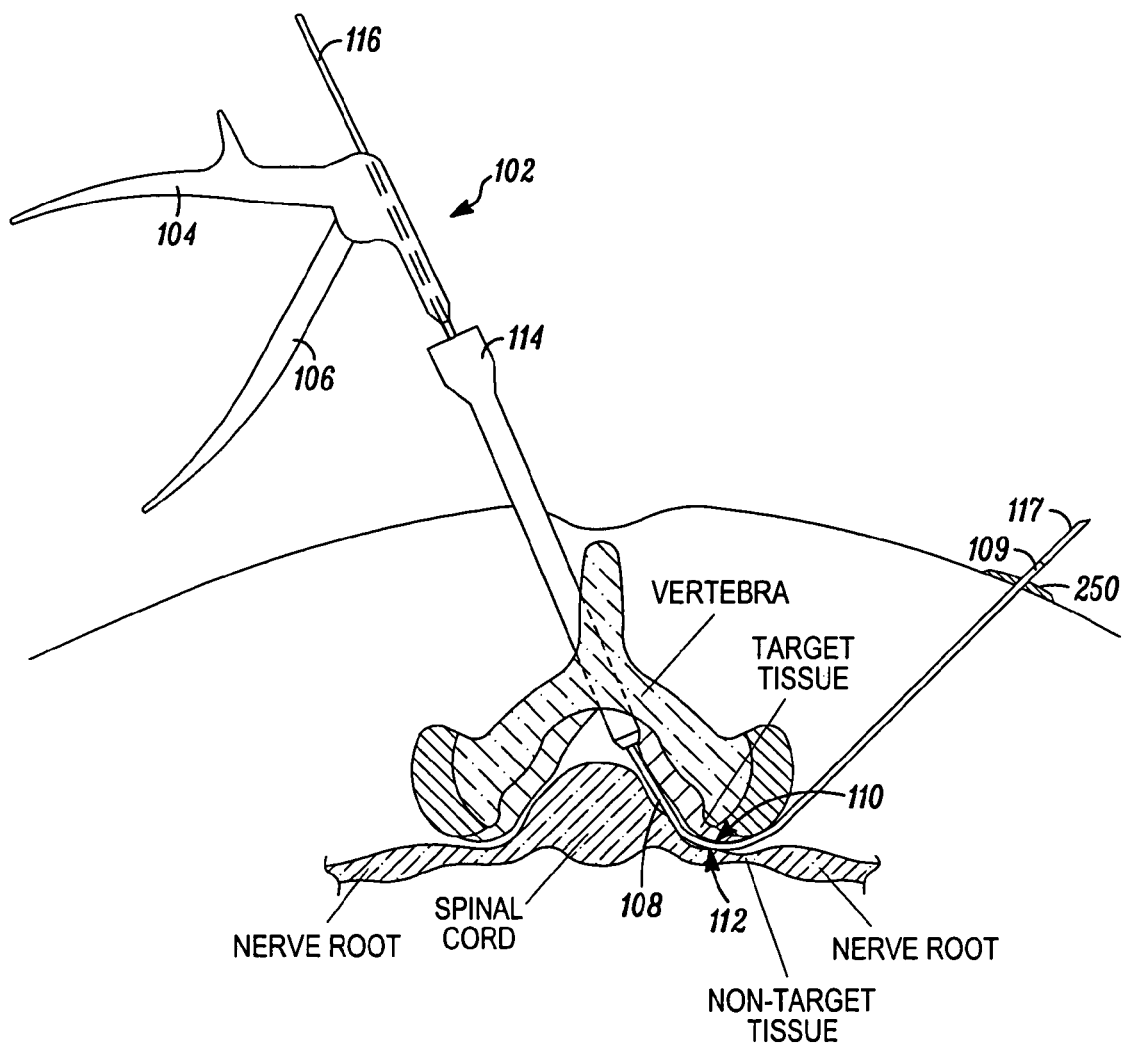
FIG. 6A is a cross-sectional view of a portion of a patient's spine and back, with apparatus for modifying tissue in position for modifying spinal tissue and with a distal portion of the apparatus anchored outside the patient according to one embodiment of the present invention.

Referring now to FIG. 6A, tissue modification device 102 is shown with one embodiment of a distal anchoring member 250 deployed at the patient's skin. In various embodiments, anchoring members may include but are not limited to one or more handles, barbs, hooks, screws, toggle bolts, needles, inflatable balloons, meshes, stents, wires, lassos, backstops or the like. In some embodiments, anchoring members 250 may be disposed at the extreme distal portion 109 of elongate body 108, while in other embodiments anchoring members 250 may be located more proximally. In the embodiment shown, anchoring members 250 are deployed at the patient's skin. In an alternative embodiment, anchoring may be achieved outside the patient by deploying one or more anchoring members 250 above the skin and having a user grasp the anchoring members 250. In an alternative embodiment, anchoring may be achieved outside the patient by deploying one or more anchoring members 250 above the skin and having a user grasp anchoring members 250, after tissue modification device 102 has been anchored to the guide member. In another alternative embodiment, anchoring may be achieved outside the patient by attaching anchoring member 250 to an external device, for example one that is mounted on the patient or on the procedure table. In a further alternative embodiment, anchoring may be achieved outside the patient by attaching the guide member to an external device, for example one that is mounted to on the patient or on the procedure table, after tissue modification device 102 has been anchored to the guide member. Anchoring members 250 generally are deployable from a first, contracted configuration to facilitate delivery of device 102, to a second, expanded configuration to facilitate anchoring. This change in configuration may be achieved, for example, by using shape memory or super-elastic materials, by spring loading anchoring members 250 into body 108 or the like. In most embodiments, anchoring members 250 may also be collapsed down into the first, contracted configuration after a tissue modification procedure has been performed, to facilitate withdrawal of device 102 from the patient. In an alternative embodiment, anchoring members 250 may detach from body 108 and may be easily removable from the patient's skin.

Figure 6B:
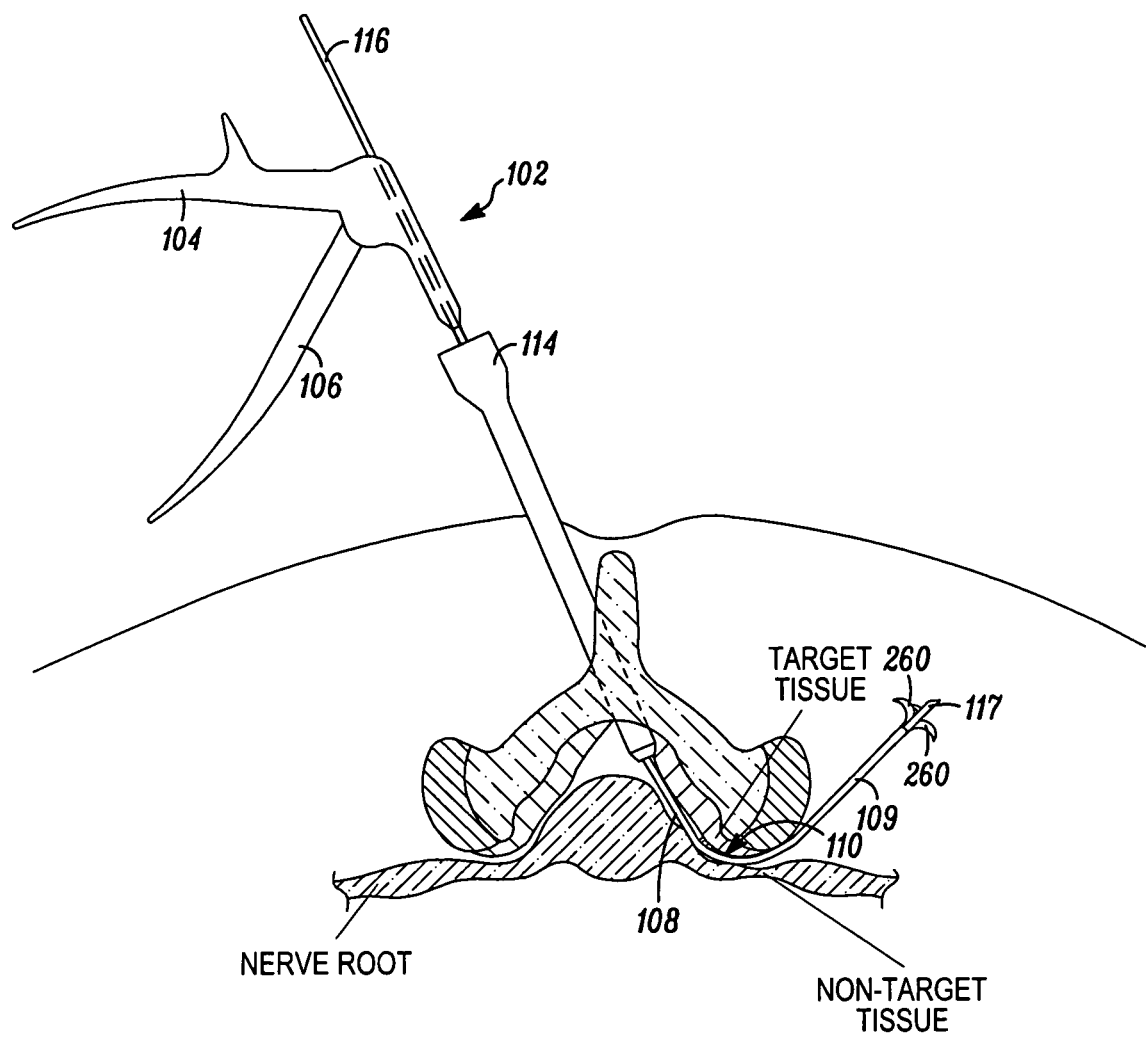
FIG. 6B is a cross-sectional view of a portion of a patient's spine and back, with apparatus for modifying tissue in position for modifying spinal tissue and with a distal portion of the apparatus anchored inside the patient according to one embodiment of the present invention.

FIG. 6B shows tissue modification device 102 with an alternative embodiment of a distal anchoring member 260. Here, distal anchoring member 260 includes multiple hooks or barbs extended out the distal portion 109 of elongate body 108 within the patient's back. In using such an embodiment, it may not be necessary to pass guide member 117 through a second, distal incision on the patient, although in some embodiments guide member 117 may extend significantly beyond distal portion 109. Anchoring member(s) 260, according to various embodiments, may be deployed so as to anchor to bone, ligament, tendon, capsule, cartilage, muscle, or any other suitable tissue of the patient. They may be deployed into vertebral bone or other suitable tissue immediately adjacent an intervertebral foramen or at a location more distant from the intervertebral foramen. When a tissue modification procedure is complete, anchoring members 260 are retracted within elongate body for removal of device 102 from the patient.

Figure 7A:
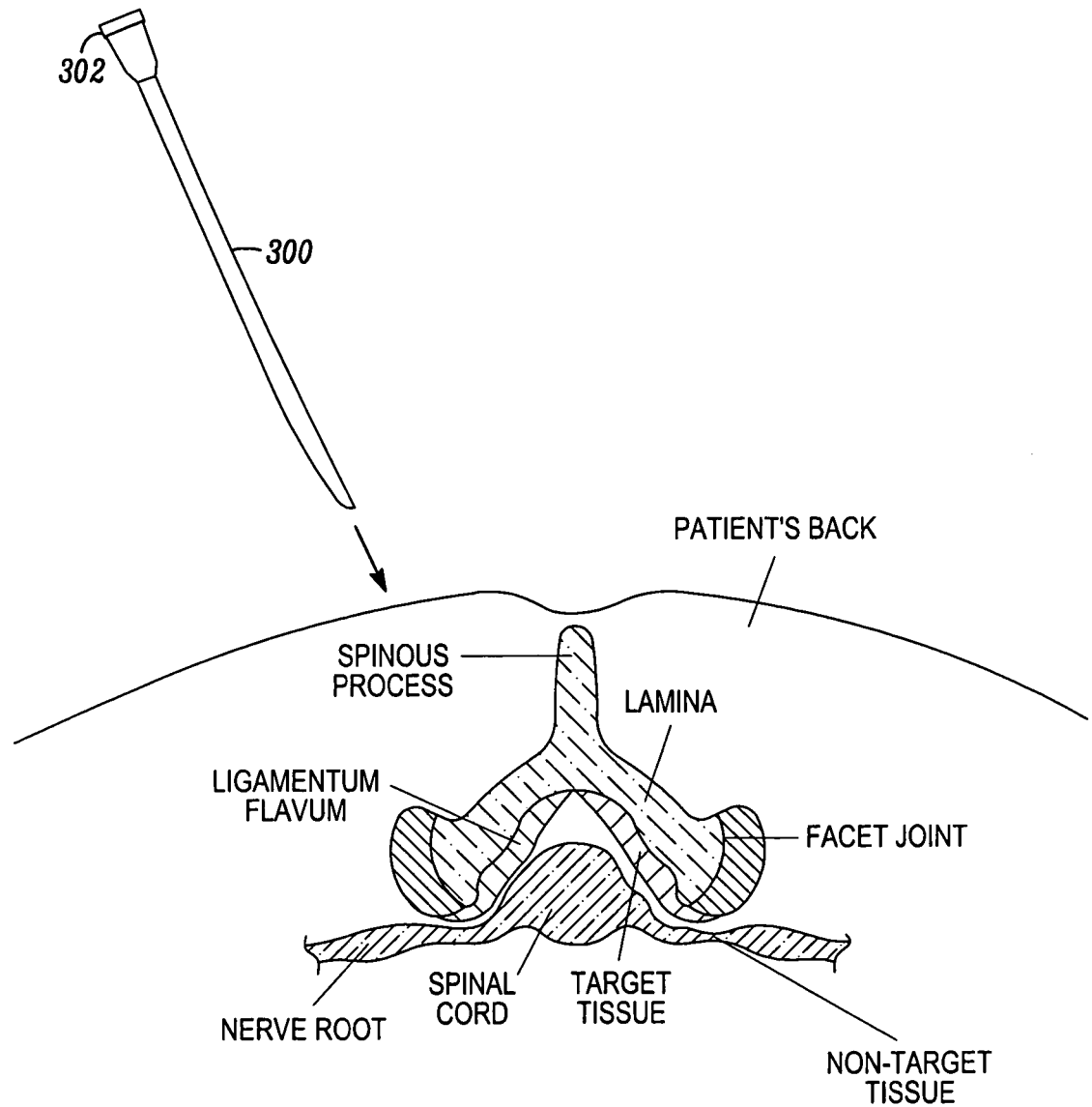
FIGS. 7A-7S are cross-sectional views of a portion of a patient's spine and back, demonstrating a method for introducing apparatus for modifying spinal tissue to an area in the spine for performing the tissue modification according to one embodiment of the present invention.
Figure 7B:
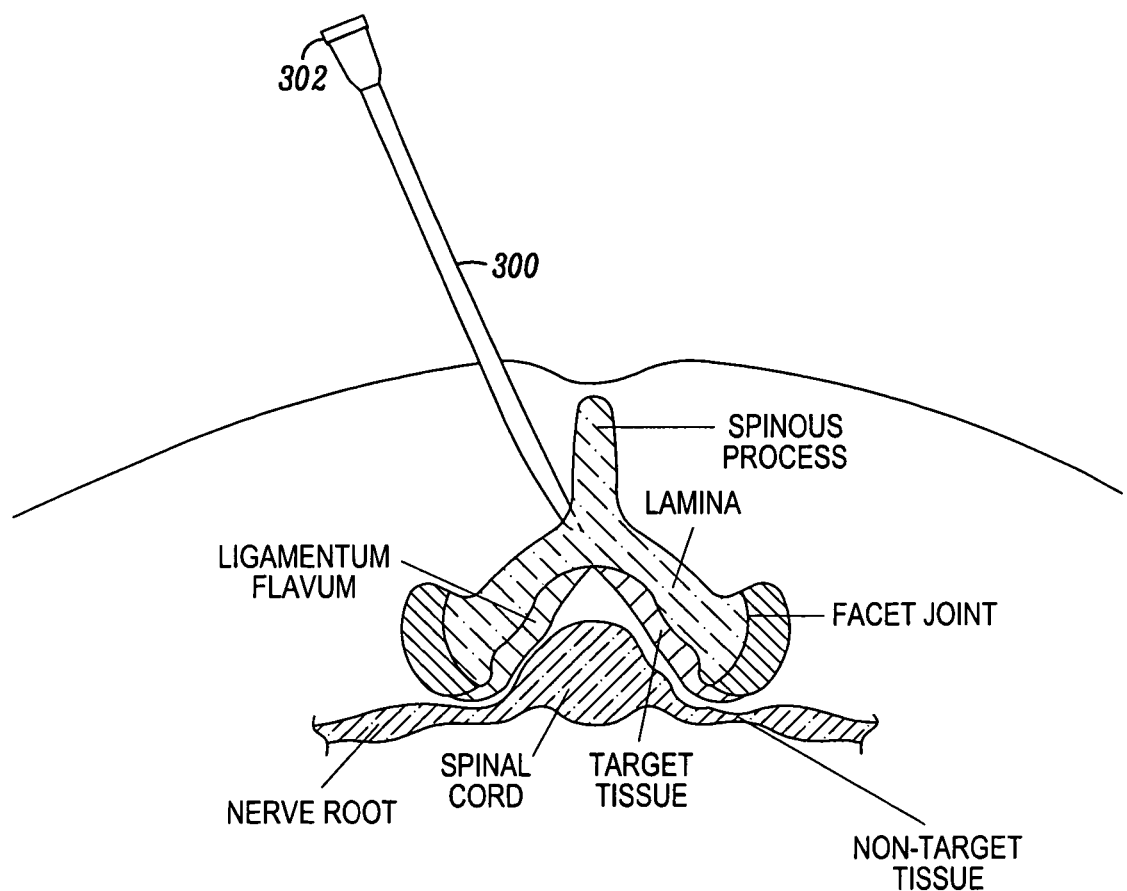
Figure 7C:
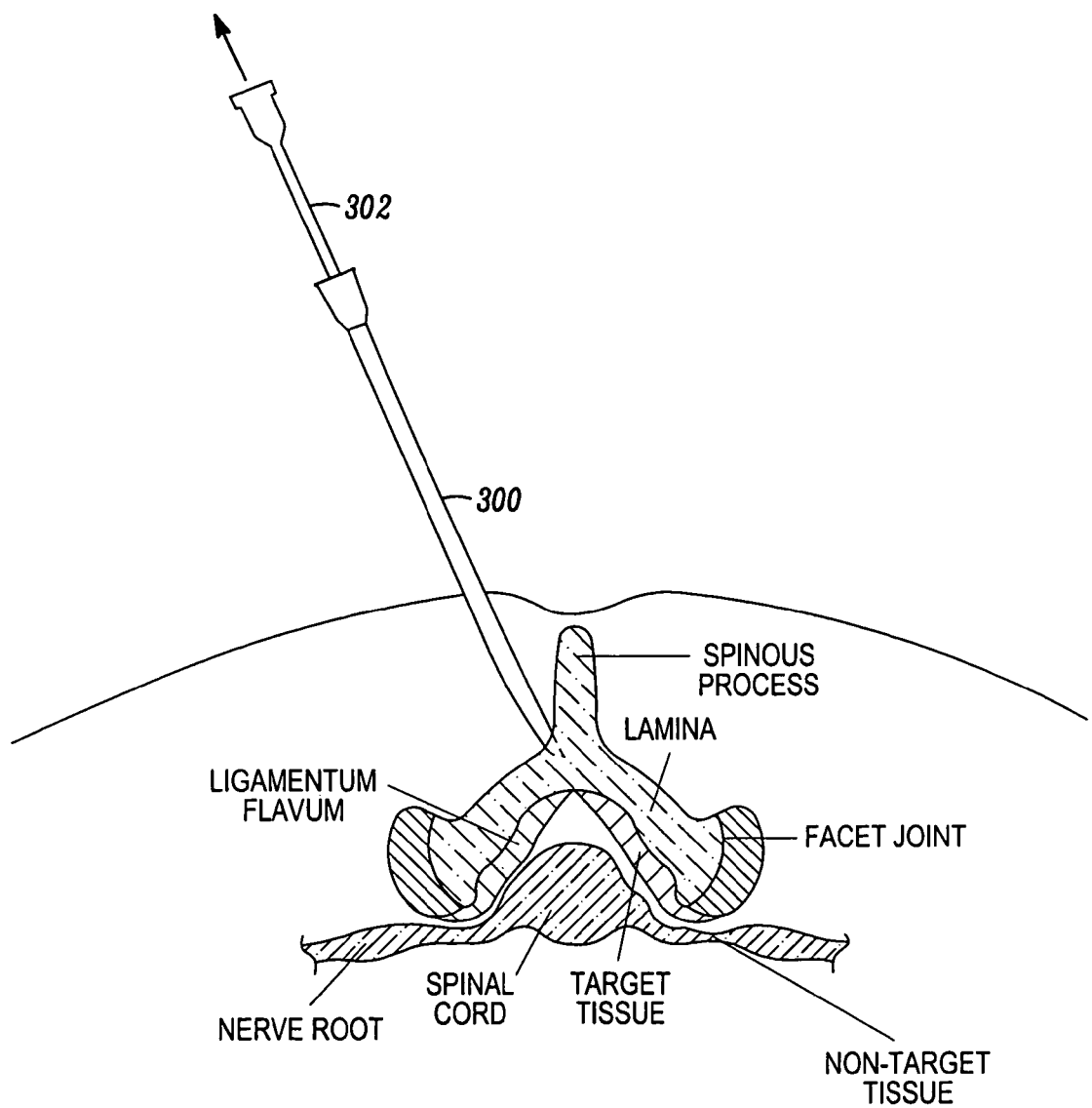
Figure 7D:
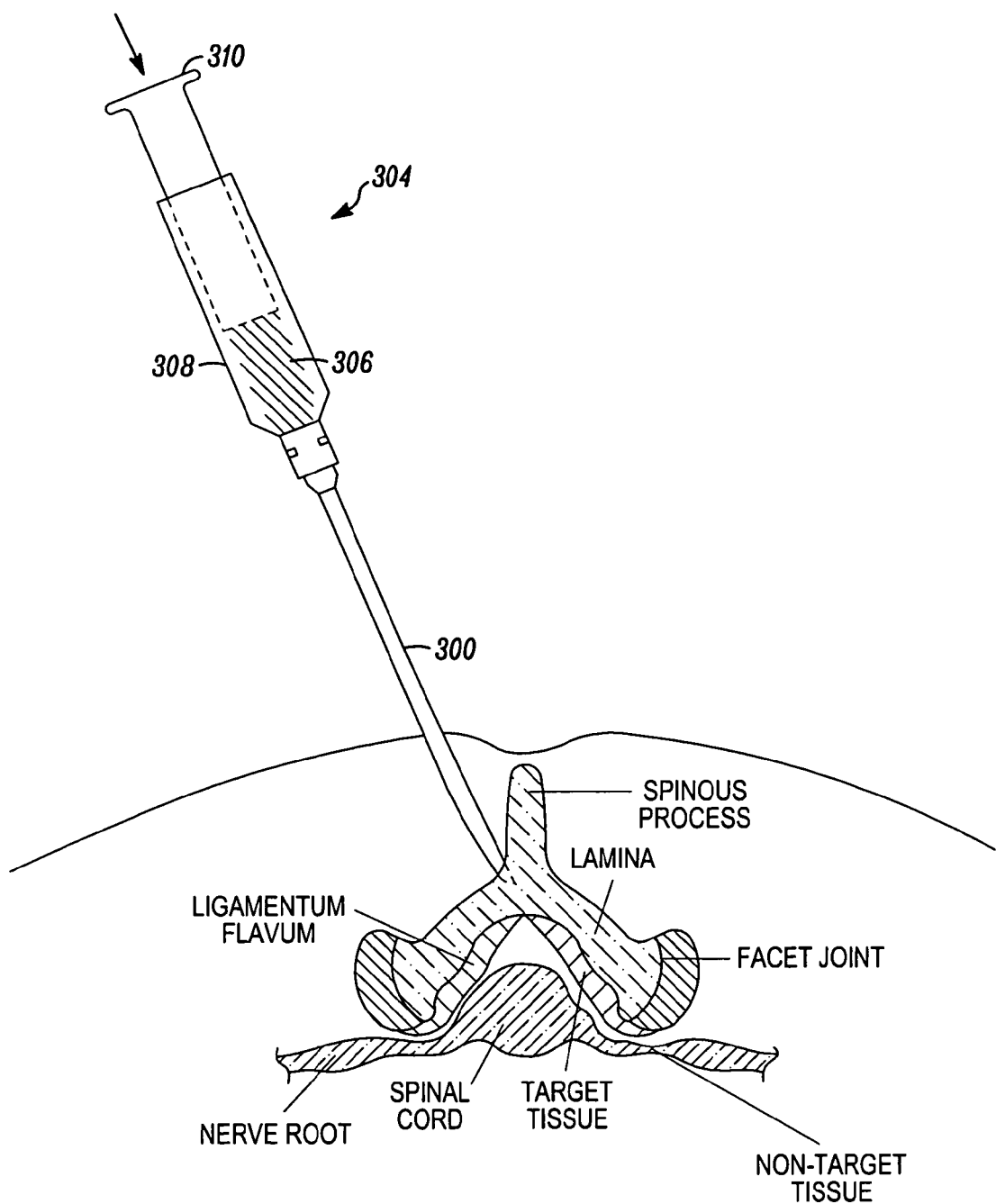
Figure 7E:
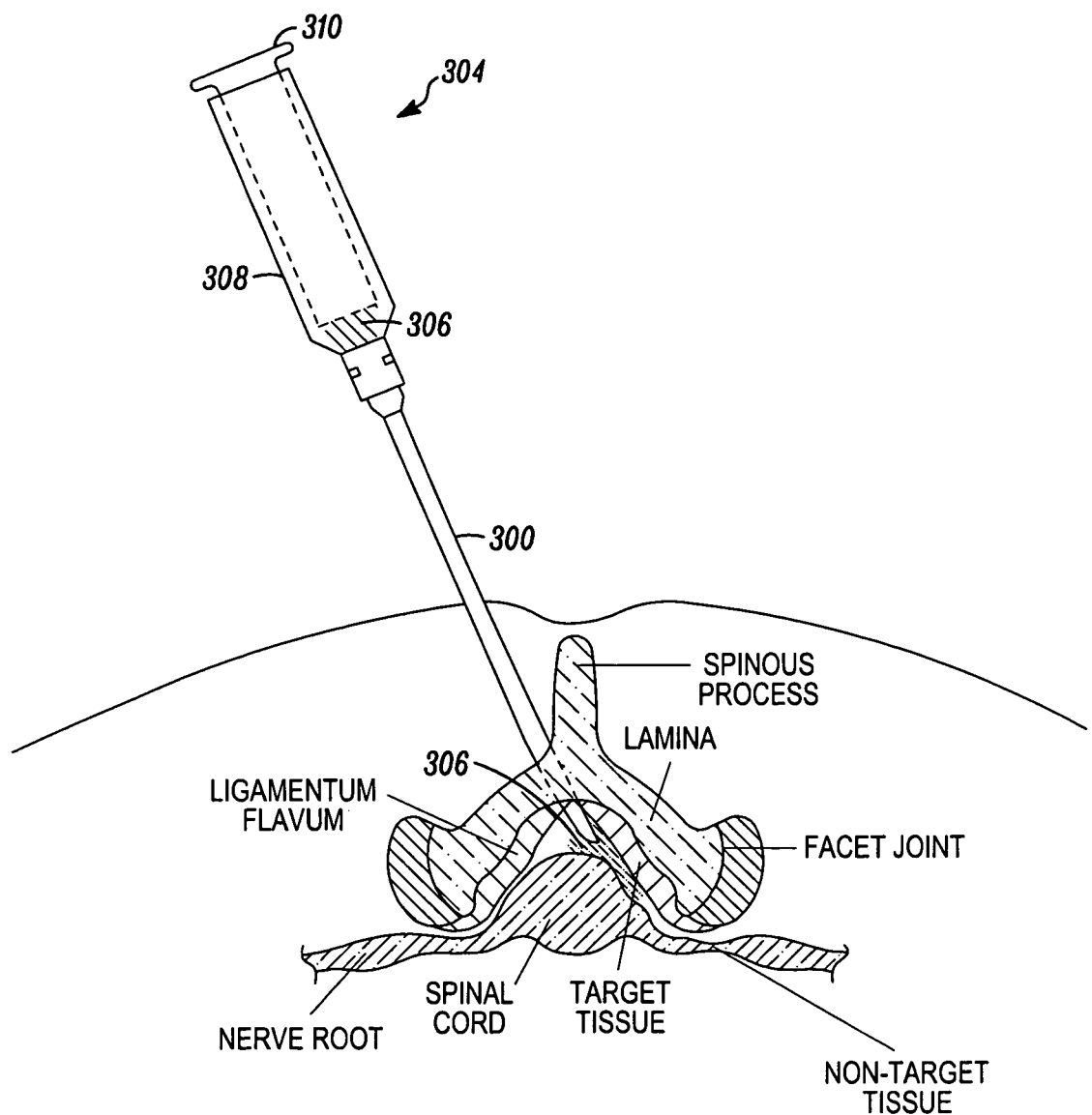
Figure 7F:
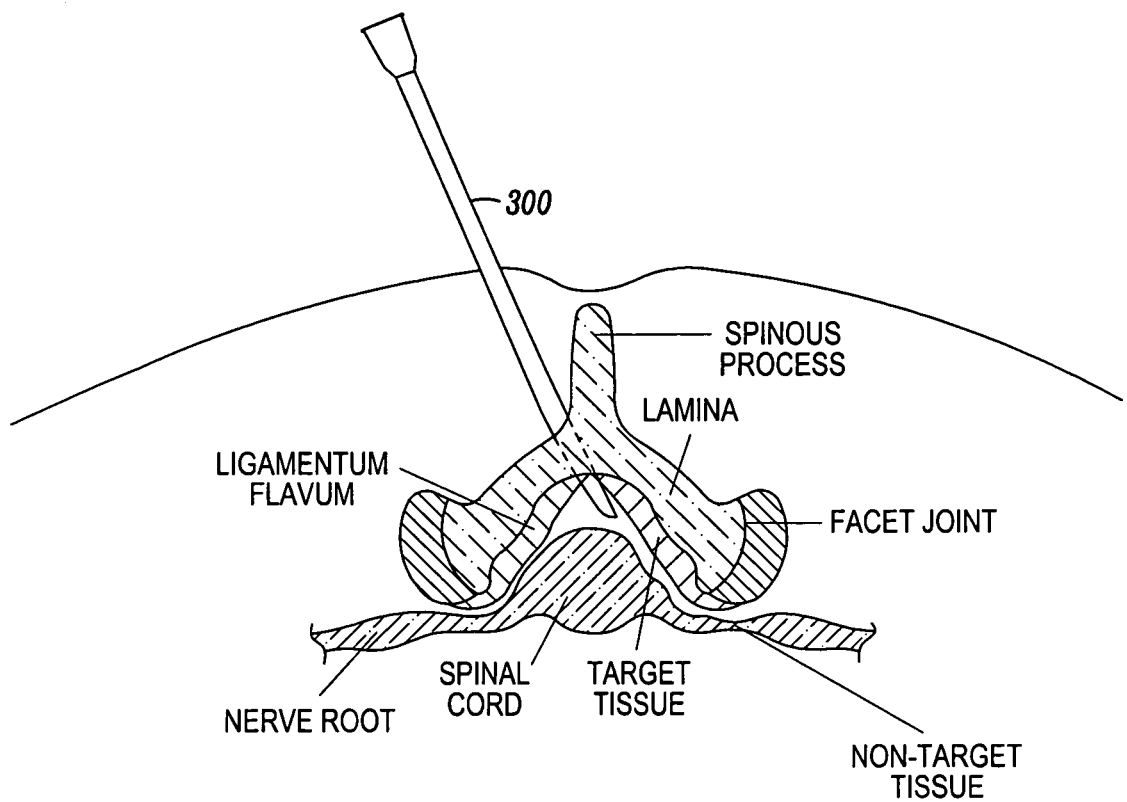
Figure 7G:
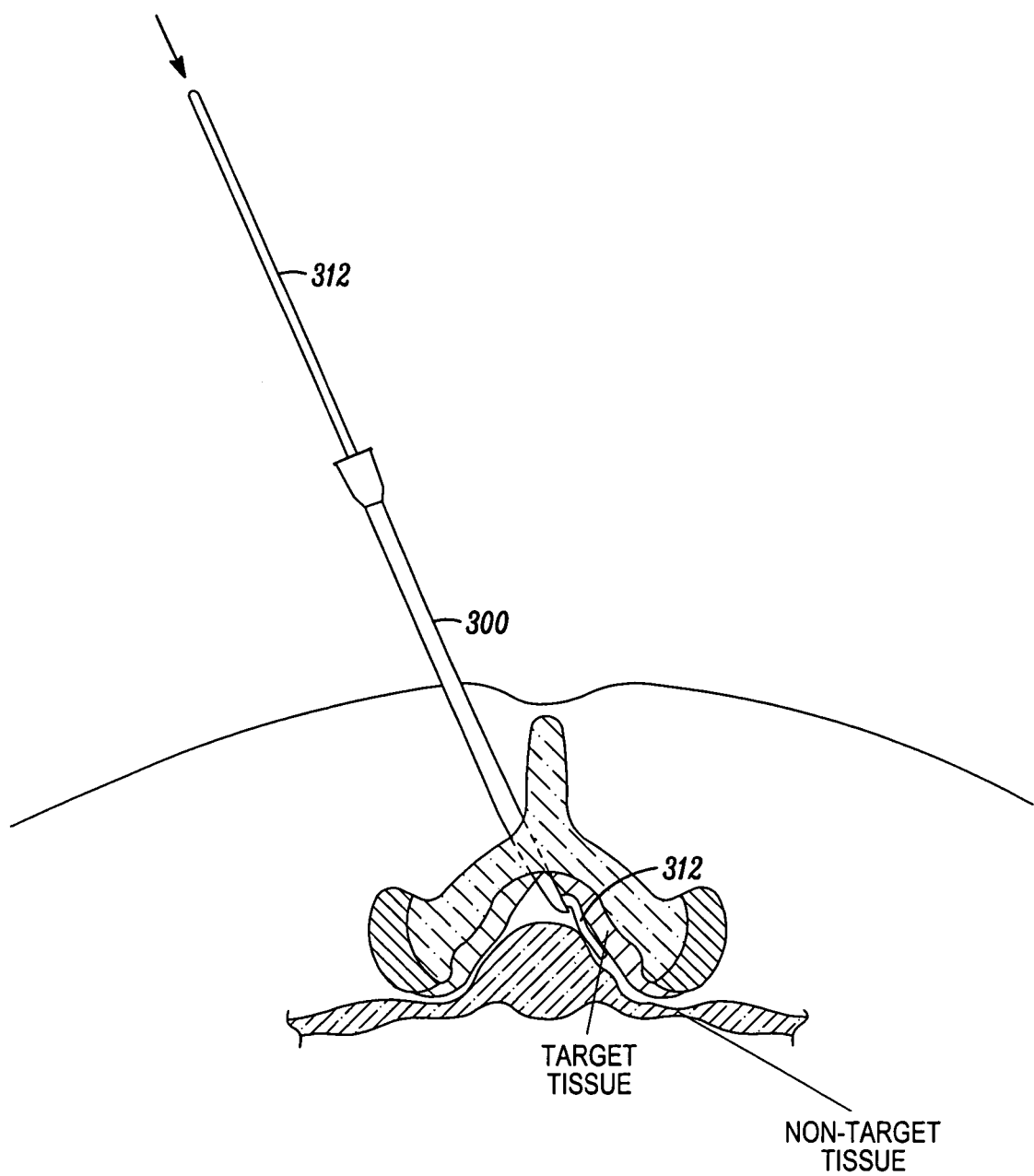
Figure 7H:
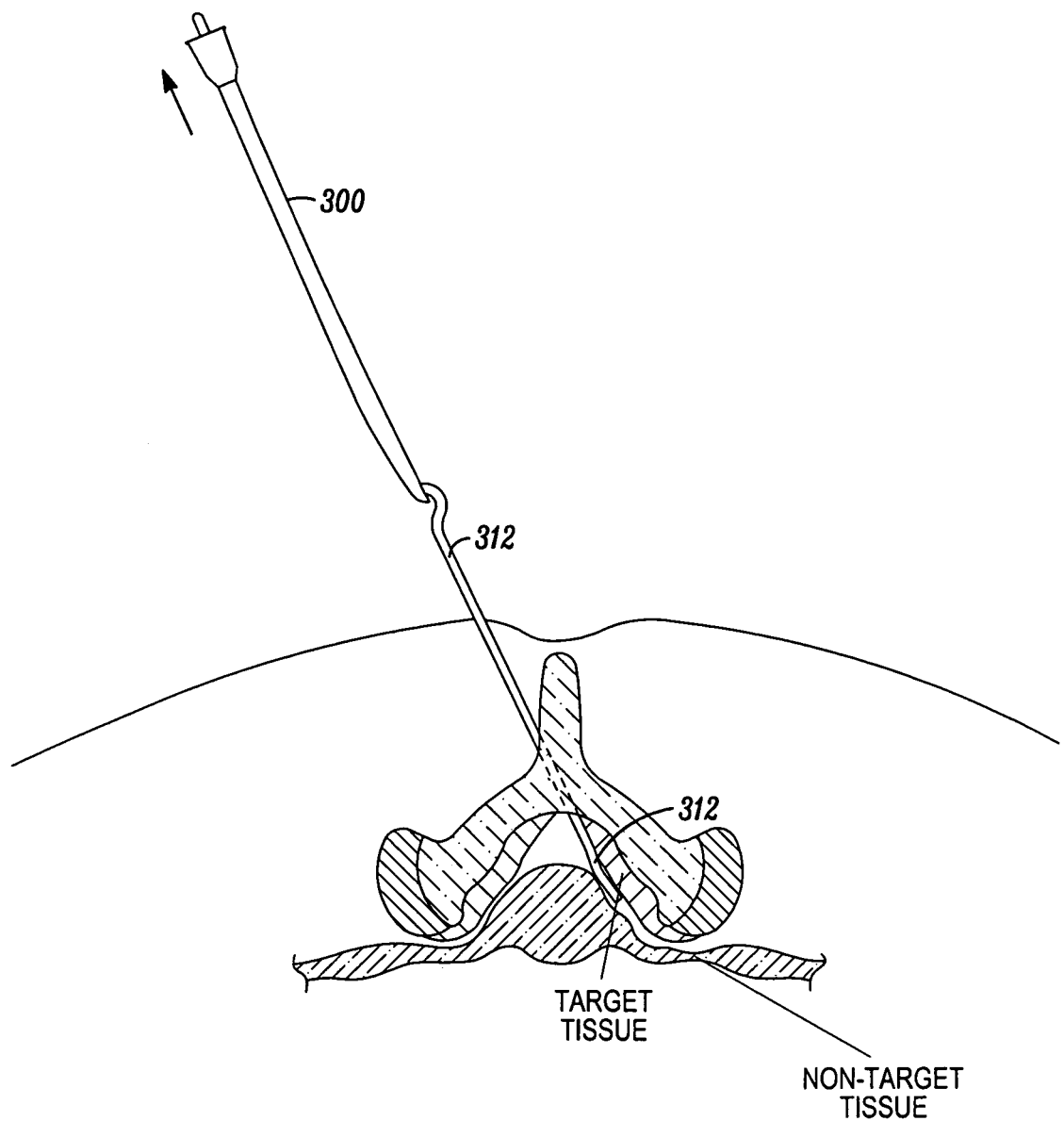
Figure 7I:
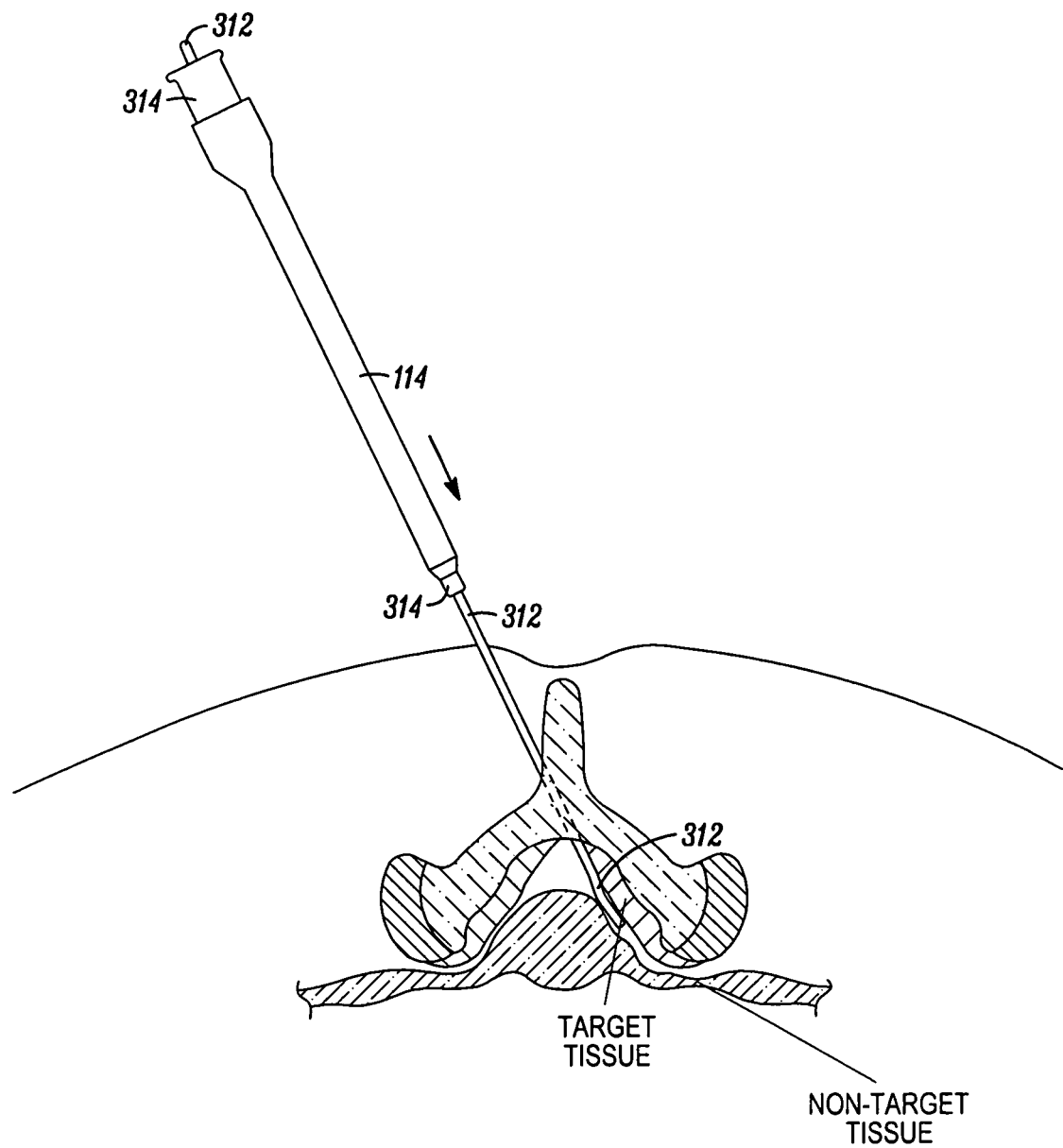
Figure 7J:
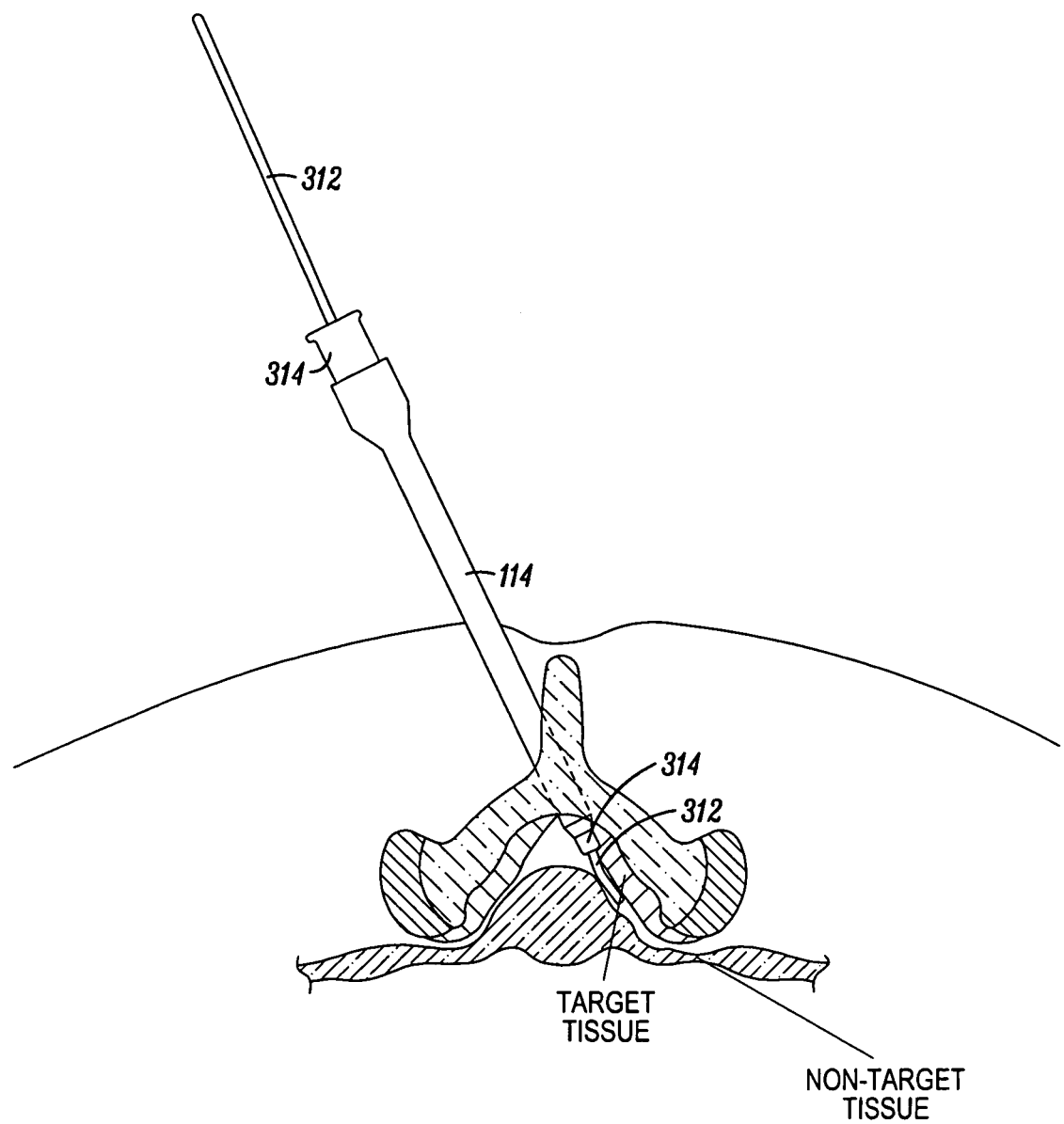
Figure 7K:
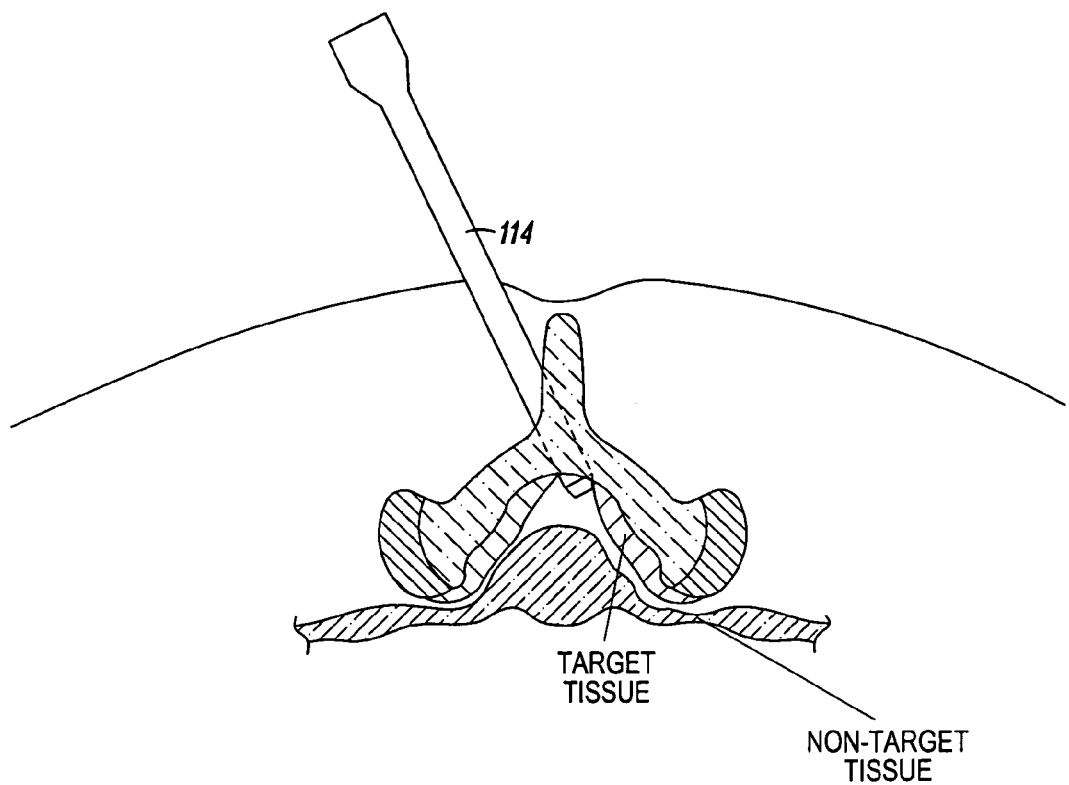
Figure 7L:
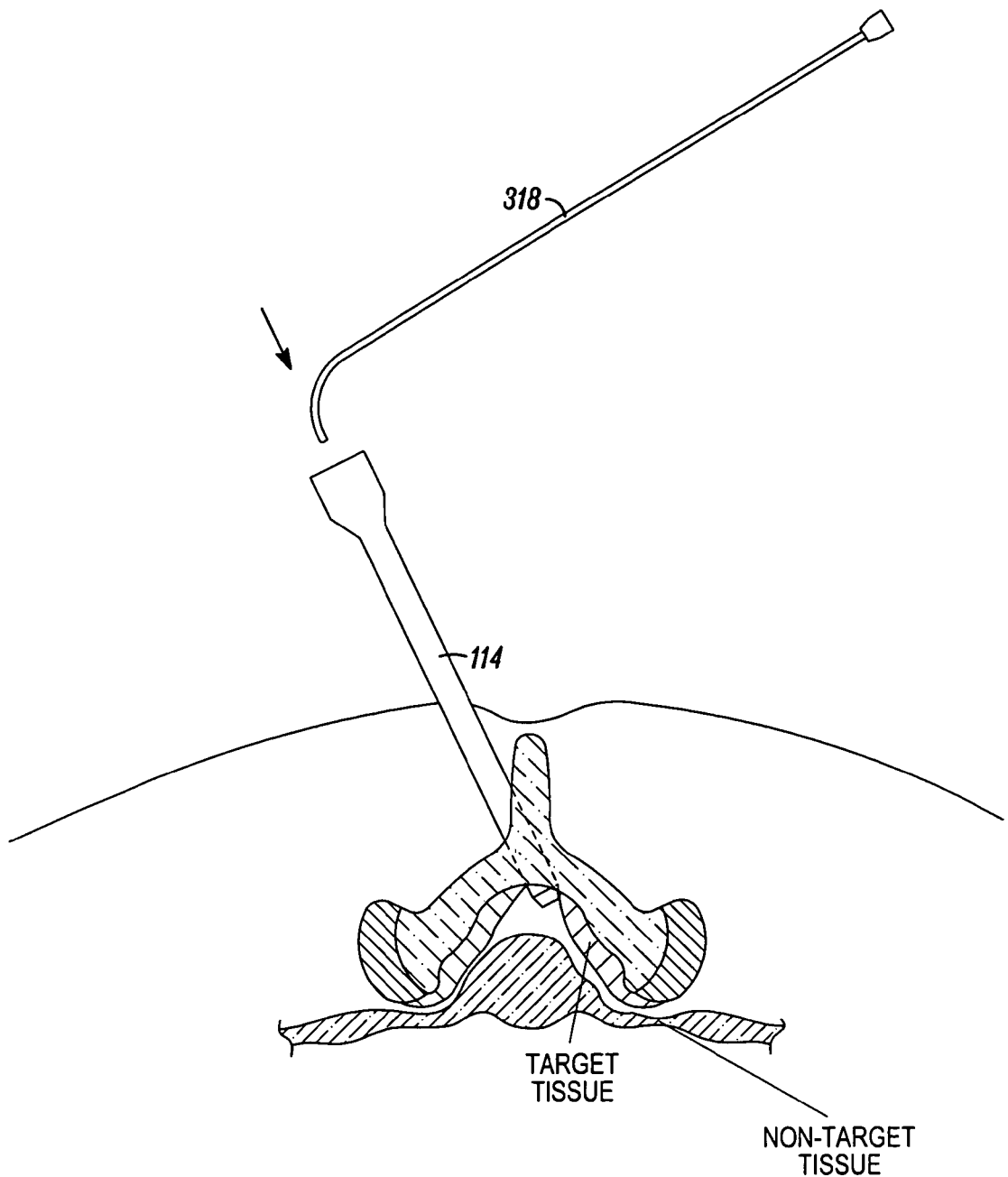
Figure 7M:
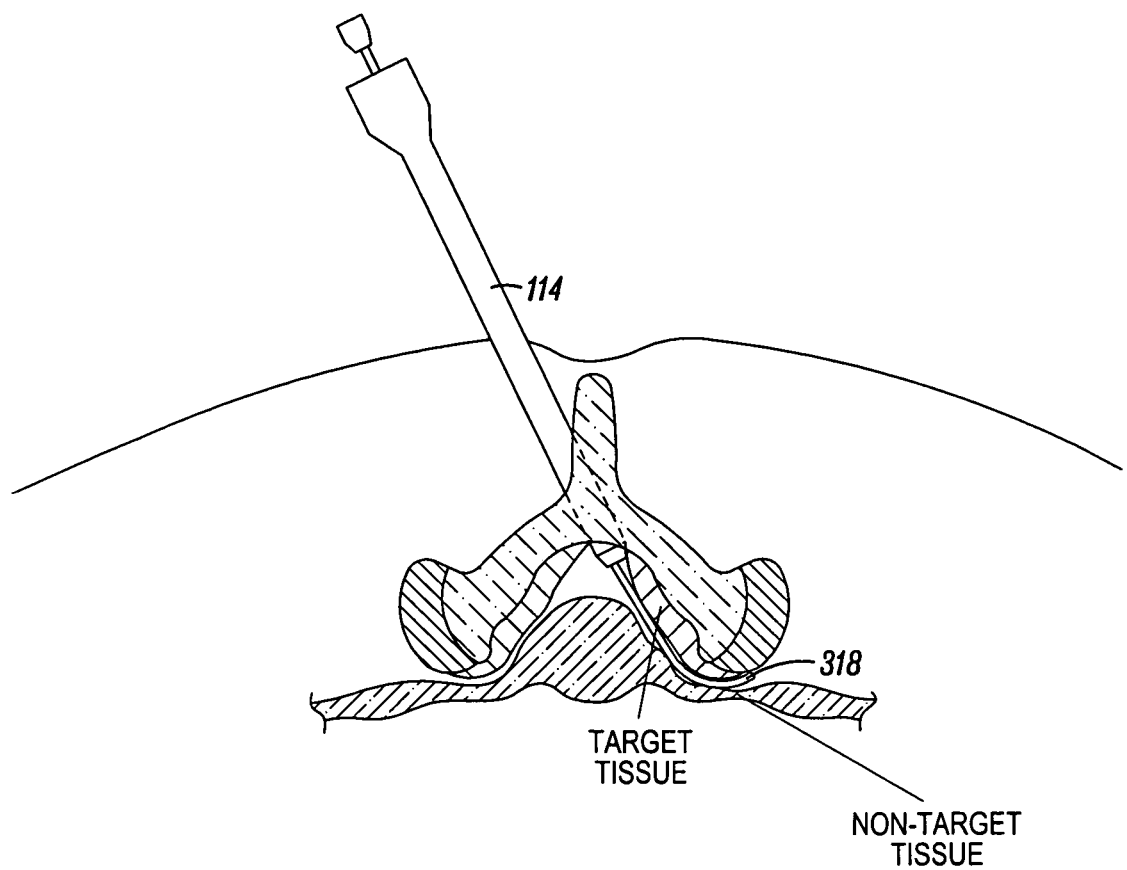
Figure 7N:
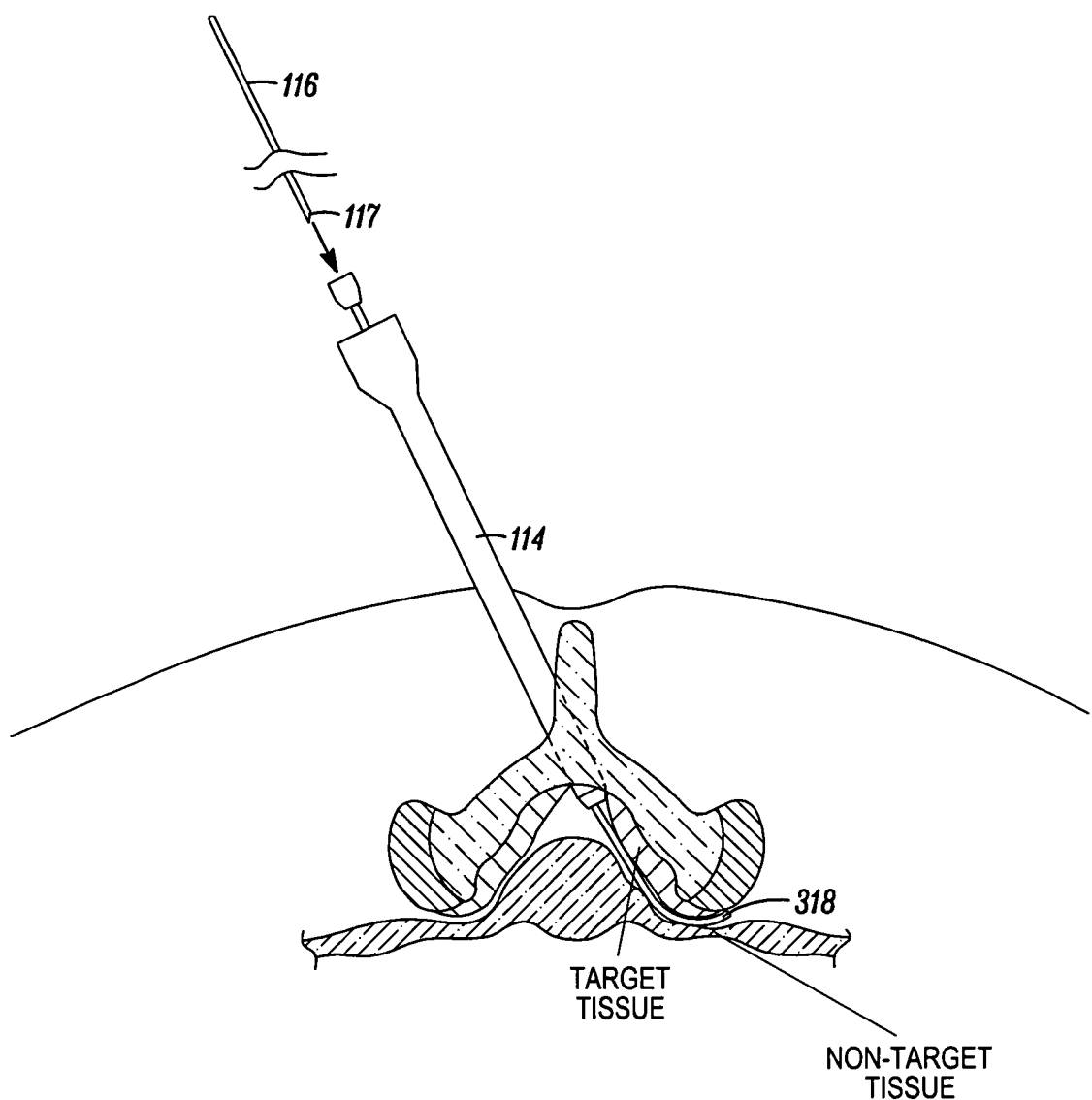
Figure 7O:
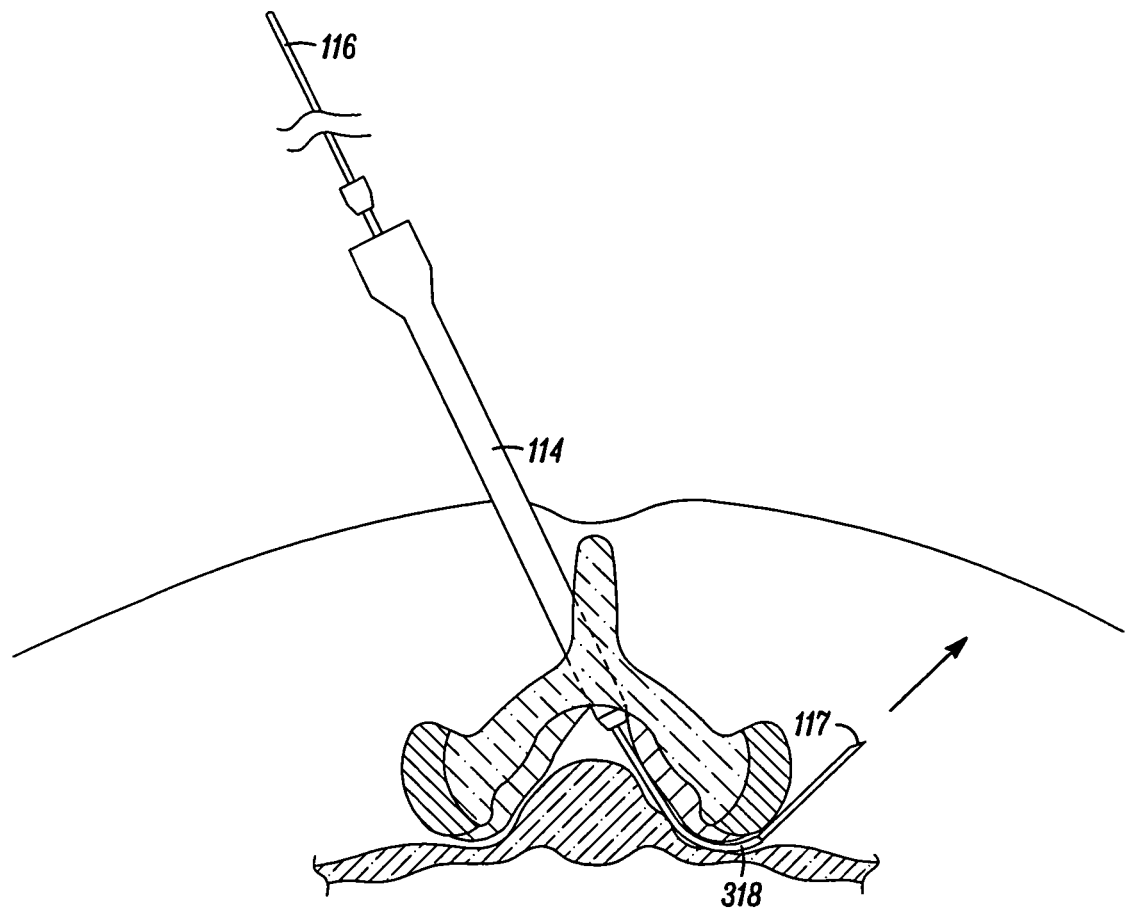
Figure 7P:
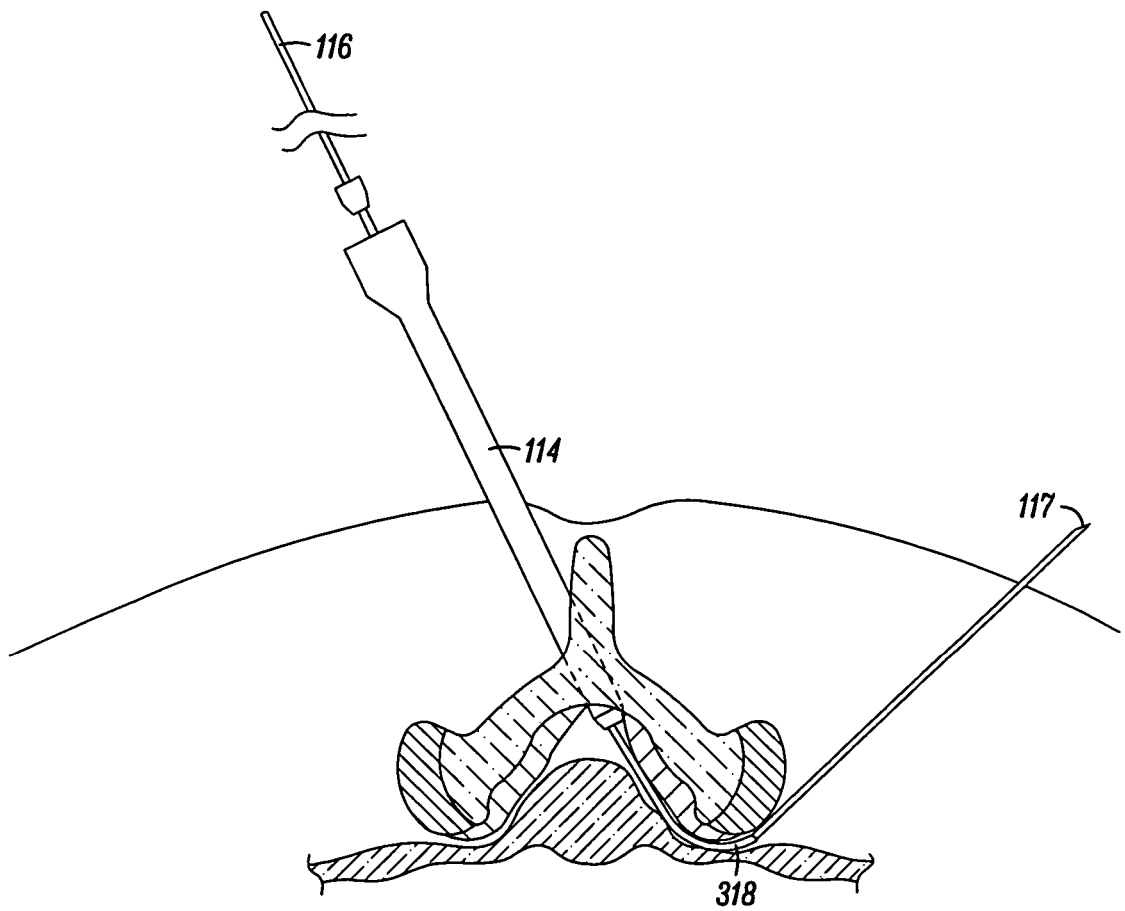
Figure 7Q:
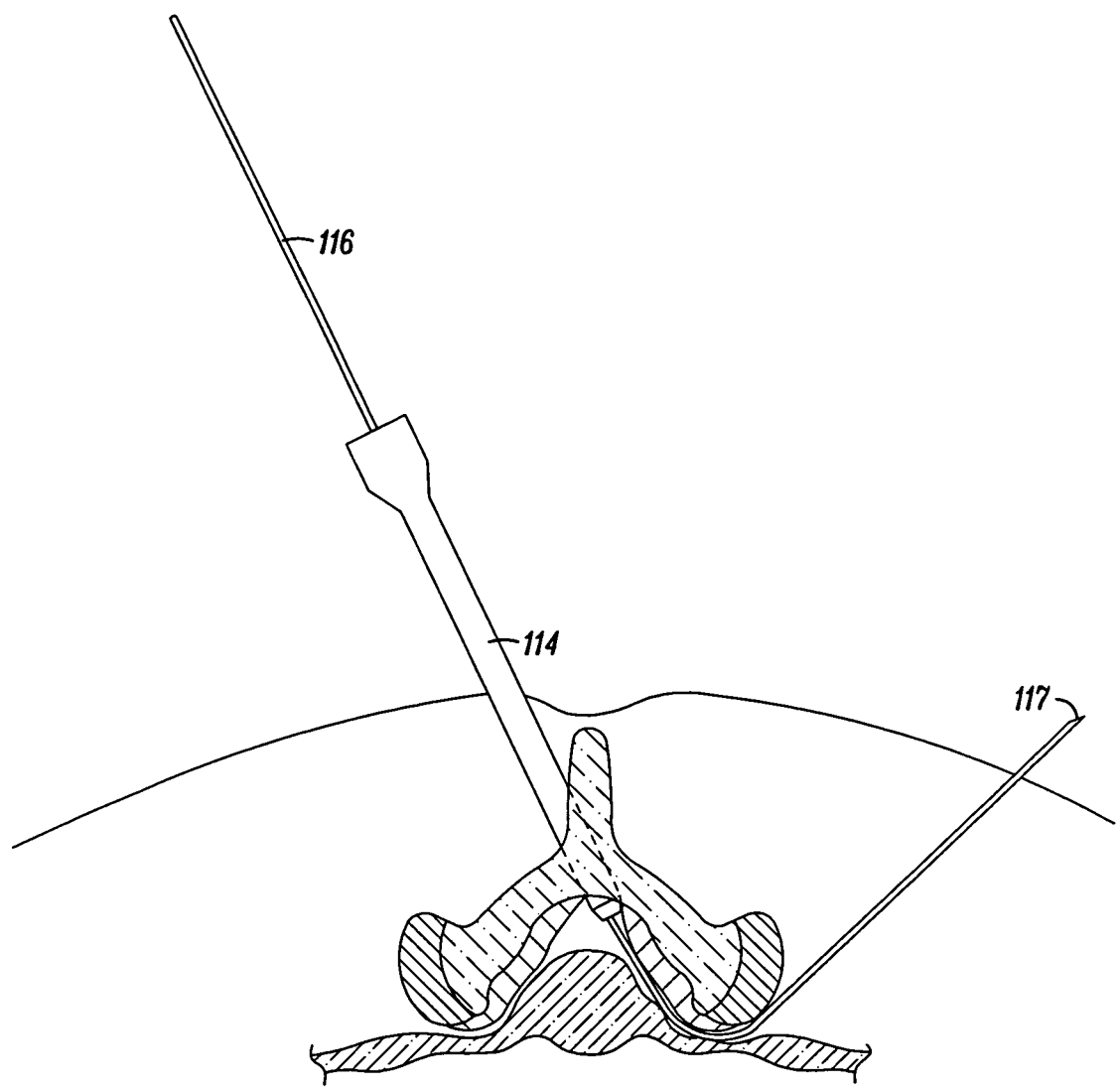
Figure 7R:
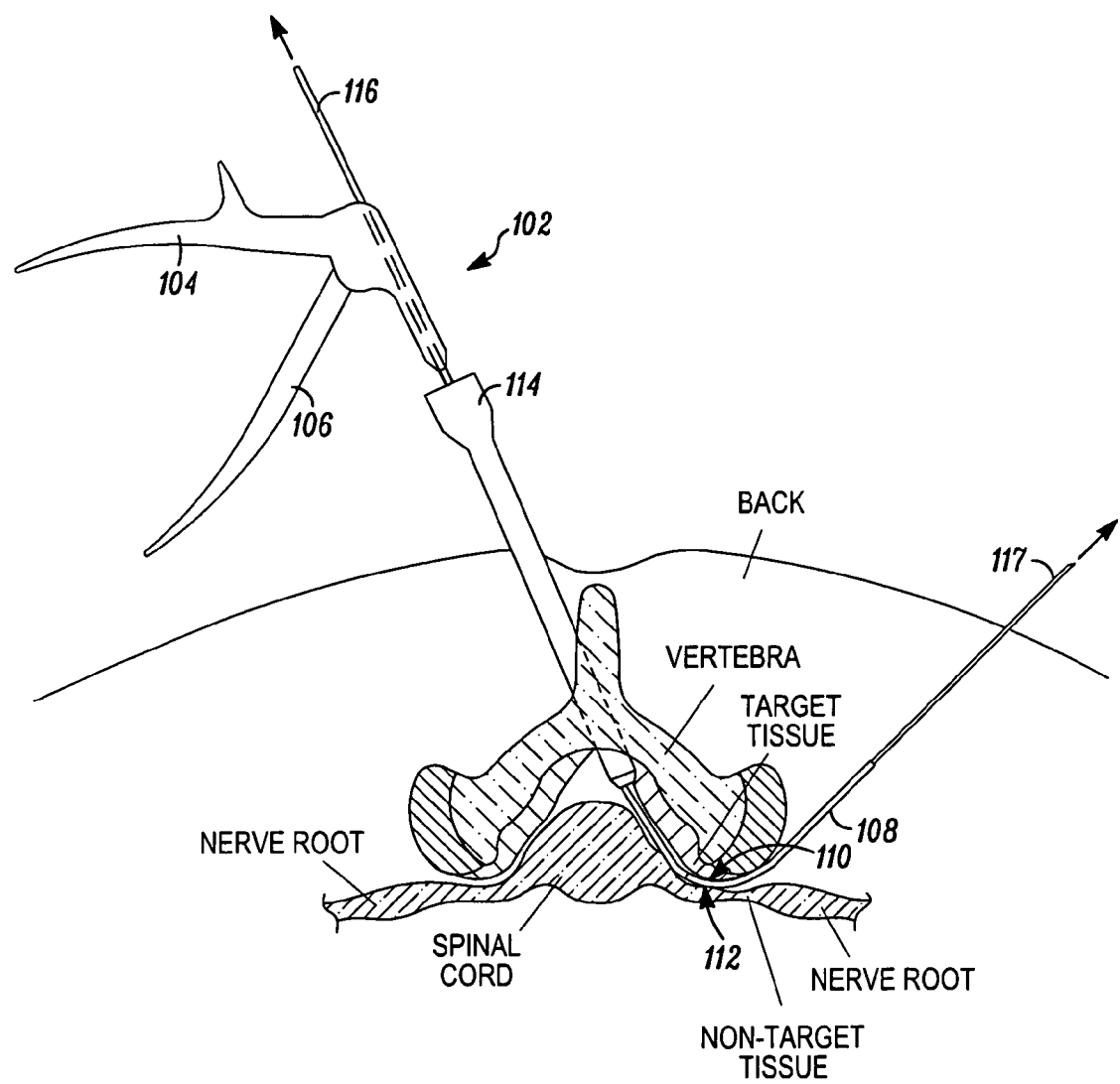
Figure 7S:
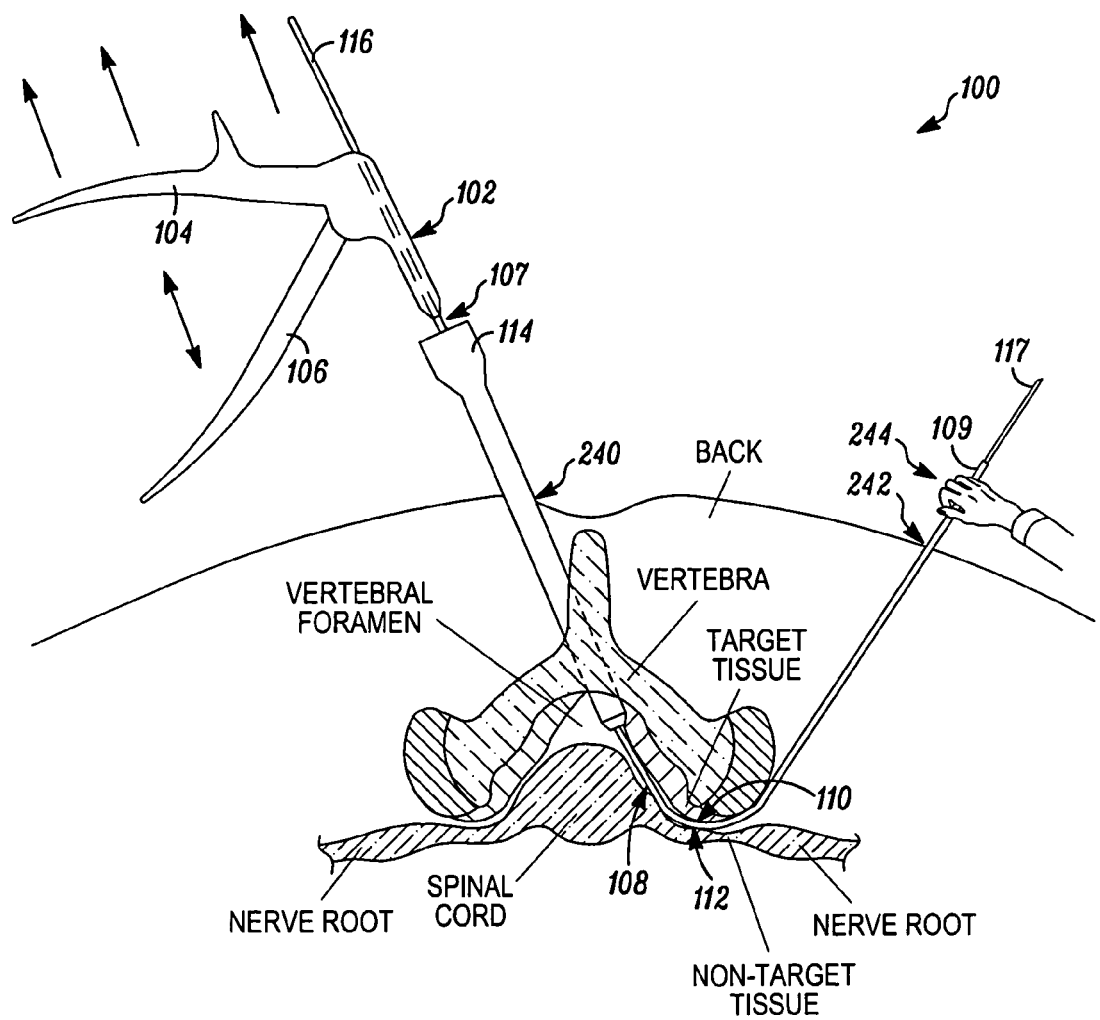

Referring now to FIGS. 7A-7S, a system and method for introducing a tissue modification device into a spine is demonstrated. This system and method may be referred to as an "access system" or "access method," in that they provide or facilitate gaining access to a target tissue to be modified. Of course, the embodiment shown is merely one exemplary embodiment, and any of a number of other suitable methods, devices or systems may be used to introduce one or more devices for modifying tissue in spine. For example, in one alternative embodiment a spinal tissue modification procedure may be carried out through an open surgical approach. Therefore, the following description is provided primarily for exemplary purposes and should not be interpreted to limit the scope of the invention as it is defined in the claims.

Referring to FIG. 7A, in one embodiment a device delivery method first involves advancing an introducer cannula 300 coupled with a stylet 302 into the patient's back. Cannula 300 and stylet 302 are then passed between adjacent vertebrae and into the ligamentum flavum or an adjacent spinal ligament, as shown further in FIG. 7B. As shown in FIG. 7C, when the distal tip of cannula is positioned as desired, stylet 302 is removed. Referring to FIGS. 7D and 7E, a loss of resistance syringe 304 including a plunger 310, barrel 308 and fluid and/or air 306, is coupled with the proximal portion of cannula 300. The distal portion of cannula 300 is advanced through the ligamentum flavum until it enters the central spinal canal where a loss of resistance to pressure placed on plunger 310 is encountered, and fluid and/or air 306 is injected into central spinal canal to confirm correct placement of cannula 300 as shown in FIG. 7E. Syringe 304 is then removed, as in FIG. 7F, and a guidewire 312 with a non-rigid, atraumatic tip is advanced through cannula 300 into the central spinal canal, as in FIG. 7G. Next, cannula 300 is removed, as in FIG. 7H, leaving behind guidewire 312. As shown in FIGS. 7I and 7J, an introducer sheath 114, coupled with a dilator 314, is then advanced over guidewire 312 to position a distal portion of sheath 114 at a desired location within the spine. Dilator 314 and guidewire 312 are then removed, as in FIG. 7K.

Once introducer sheath 114 is in place, one or more curved or steerable guide devices 318 may be advanced through it to desired positions in and/or through the spine, as shown in FIGS. 7L and 7M. One or more guide members 116, may then be advanced through the guide device 318, as shown in FIGS. 7N-7P. Finally, guide device 318 may be removed, as in FIG. 7Q, and elongate body 108 of tissue modification device 102 may be advanced over guide member 116 and through introducer sheath 114 to a desired position in the spine, as in FIG. 7R. As shown in FIG. 7S, elongate body 108 may be tensioned to urge tissue modifying members 110 against target tissue, as shown with arrows at opposite ends of device 102, while distal portion 109 is anchored, in this case by hand 244. In an alternative embodiment, guide member 116 may be tensioned to urge tissue modifying members 110 against target tissue as shown in FIG. 7R.

Once tissue modification device 102 is in a desired position, tissues which may be modified in various embodiments include, but are not limited to, ligament, tendon, tumor, cyst, cartilage, scar, "bone spurs," inflammatory and bone tissue. In some embodiments, modifying the target tissue reduces impingement of the tissue on a spinal cord, a branching nerve or nerve root, a dorsal root ganglia, and/or vascular tissue in the spine. Actuator 106 on handle 104 is activated to modify target tissue using tissue modification member(s) 110, while elongate body 108 is held relatively stable by hand 244 and by tension force applied to handle 104.

In various embodiments, the system and method described immediately above may include additional features or steps, may have fewer features or steps, may have an alternate order of implementation of steps, or may have different features or steps. For example, in some embodiments placement of device 102 will be performed in a medial-to-lateral direction (relative to the patient), while in alternative embodiments device placement will be performed lateral-to-medial. In some embodiments, one or more components of the system described may be anchored to the patient, such as guide member 116 or introducer sheath 114. In various embodiments, one or more guide members 116 may include one or more wires, rails or tracks and may be inserted through guide device 318, introducer sheath 114 without guide device 318, cannula 300, an epidural needle, a lumen of an endoscope, a lumen of a tissue shield or barrier device, a curved guide device 318 placed through a lumen of an endoscope, or the like. In other embodiments, for example, guide device 318 may be placed through introducer cannula 300 and then introducer sheath 114 may be passed over guide device 318. Tissue modification device 102 may similarly be inserted with or without using any of these devices or components in various combinations. Various guidewires 312, guide devices 318 and/or guide members 116 may be pre-shaped to have one or more curves, may be steerable, and/or may include one or more rails, tracks, grooves, lumens, slots, partial lumens, or some combination thereof.

In some embodiments, tissue modification device 102 is inserted through one or more hollow devices as described above (such as introducer sheath 114, as shown, or cannula 300 in an alternative embodiment) in such a way that device 102 expands upon extending out of a distal portion of the hollow delivery device thereby assuming a wider profile for modifying a greater amount of target tissue from a single location. In an alternative embodiment, device 102 retains the same overall profile during insertion and during use. In some embodiments, one or more delivery devices will remain in the patient during use of tissue modification device 102, while in alternative embodiments all delivery devices are removed from the patient when tissue modification device 102 is operating. In some embodiments, tissue modification device 102 may be slidably coupled with one or more delivery devices during delivery and/or during use. In one embodiment, tissue modification device 102 is advanced through introducer sheath 114 and sheath 114 is used as an irrigation and evacuation lumen to irrigate the area of the target tissue and evacuate removed tissue and other debris, typically by applying a vacuum. In alternative embodiments, tissue modification device 102 may include an irrigation and/or evacuation lumen to irrigate an area of the target tissue and evacuate removed tissue and other debris.

Some embodiments of an access system for facilitating tissue modification may further include one or more visualization devices (not shown). Such devices may be used to facilitate placement of the access system for introducing the tissue modification device, to facilitate tissue modification itself, or any combination of these functions. Examples of visualization devices that may be used include flexible, partially flexible, or rigid fiber optic scopes, rigid rod and lens-endoscopes, CCD or CMOS chips at the distal portion of rigid or flexible probes, LED illumination, fibers or transmission of an external light source for illumination or the like. Such devices may be slidably couplable with one or more components of an access system or may be slidably or fixedly coupled with a tissue modification device. In other embodiments, additional or alternative devices for helping position, use or assess the effect of a tissue modification device may be included. Examples of other such devices may include one or more neural stimulation electrodes with EMG or SSEP monitoring, ultrasound imaging transducers external or internal to the patient, a computed tomography (CT) scanner, a magnetic resonance imaging (MRI) scanner, a reflectance spectrophotometry device, and a tissue impedance monitor disposed across a bipolar electrode tissue modification member or disposed elsewhere on a tissue modification device or disposed on the access system.

Figure 8A:
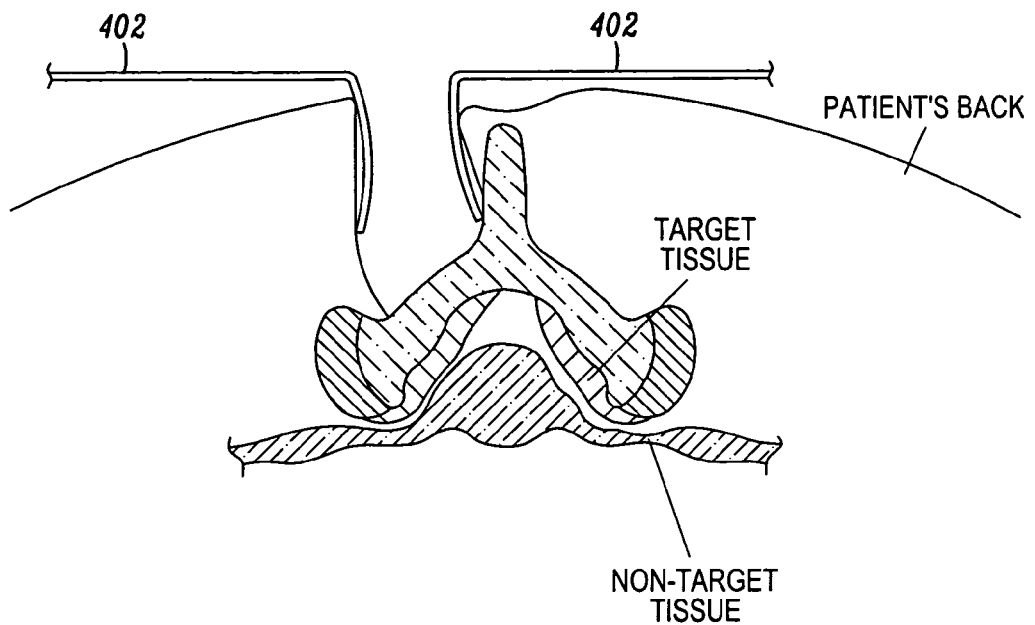
FIGS. 8A-8F are cross-sectional views of a portion of a patient's spine and back, demonstrating a method for introducing apparatus for modifying spinal tissue to an area in the spine for performing the tissue modification according to an alternative embodiment of the present invention.
Figure 8B:
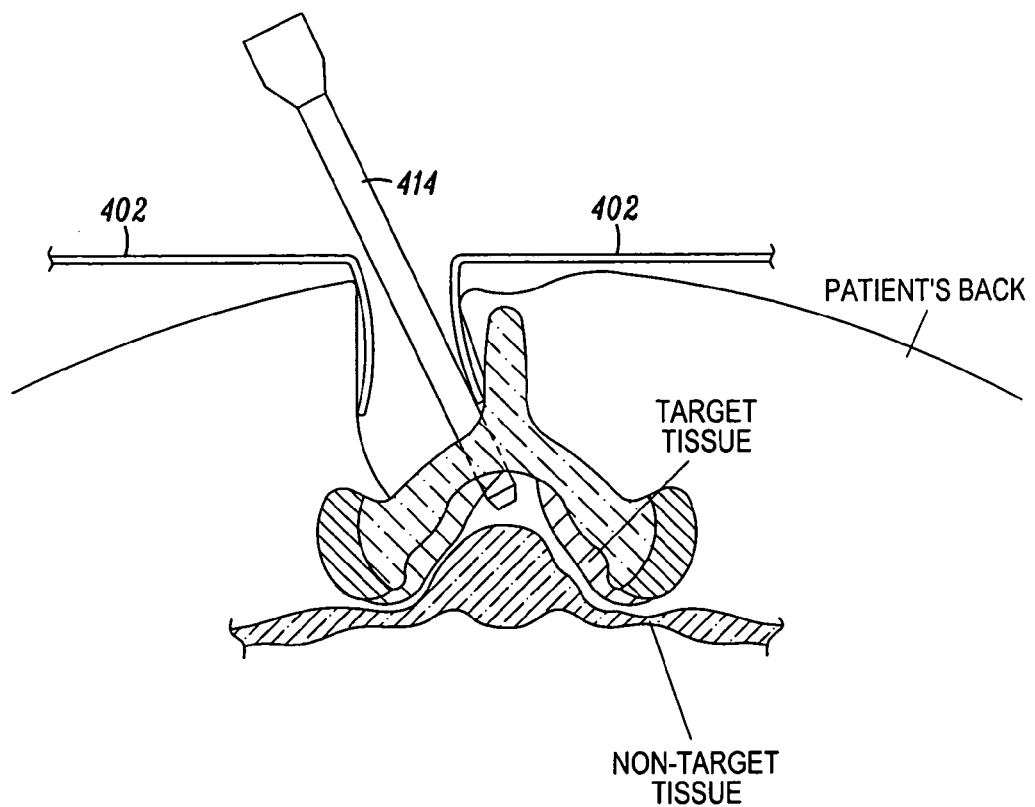
Figure 8C:
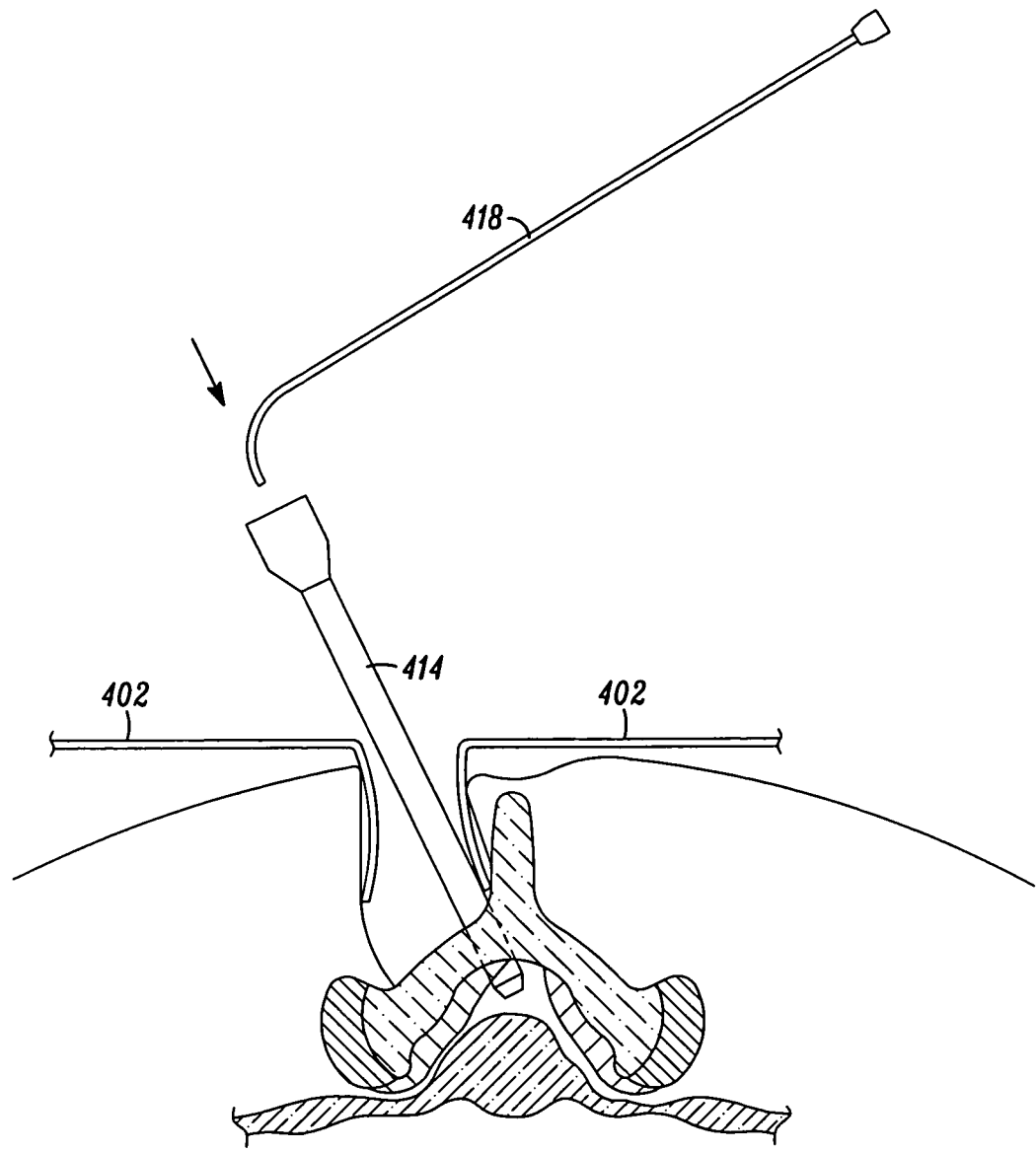
Figure 8D:
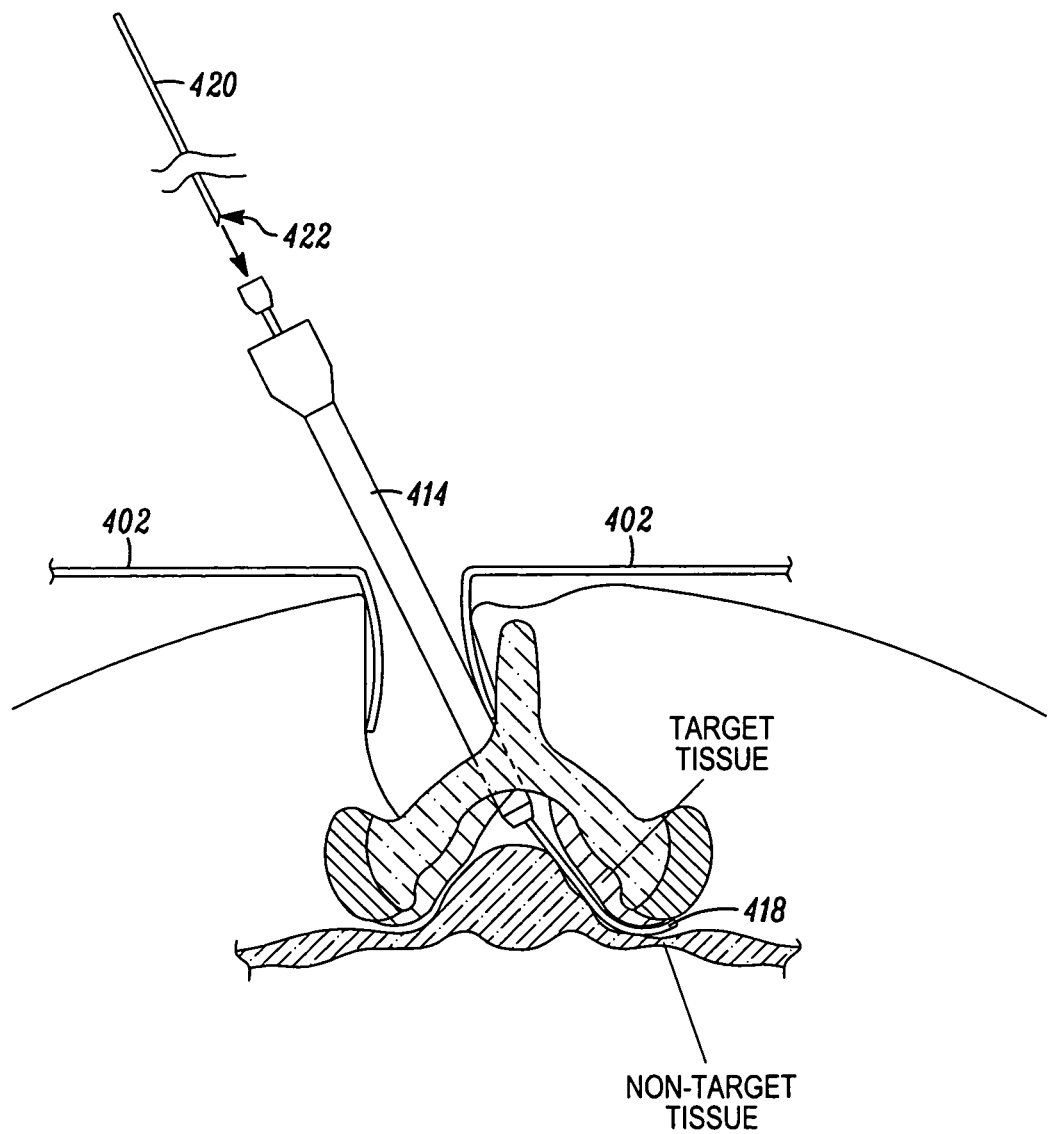

Referring now to FIGS. 8A-8E, in an alternative embodiment, a tissue modification device and optionally one or more introduction/access devices may be positioned in a patient using an open surgical technique. As shown in FIG. 8A, for example, in one embodiment an open surgical incision is made on a patient's back, and two retractors 402 are used to expose a portion of the patient's vertebra. As shown in FIG. 8B, an introducer sheath 414 may then be inserted through the incision, between retractors 402. As in FIG. 8C, a curved guide device 418 may then be inserted through introducer sheath 414. Guide device 418 extends into the epidural space and through the intervertebral foramen as shown in FIG. 8D.

In some embodiments, a curved and cannulated thin, blunt probe may be placed directly through the open incision into the epidural space of the spine, or alternatively may be placed through introducer sheath 414. The probe tip may be advanced to or through a neural foramen. Such a probe may be similar in shape, for example, to a Woodson elevator, Penfield 3, hockey stick probe, ball tipped probe, or the like. In alternative embodiments, probes that may be manually bent to change their shapes, or probes with articulating tips, or probes with shape lock portions, and/or probes having grooves instead of cannulas may be used.

Figure 8E:
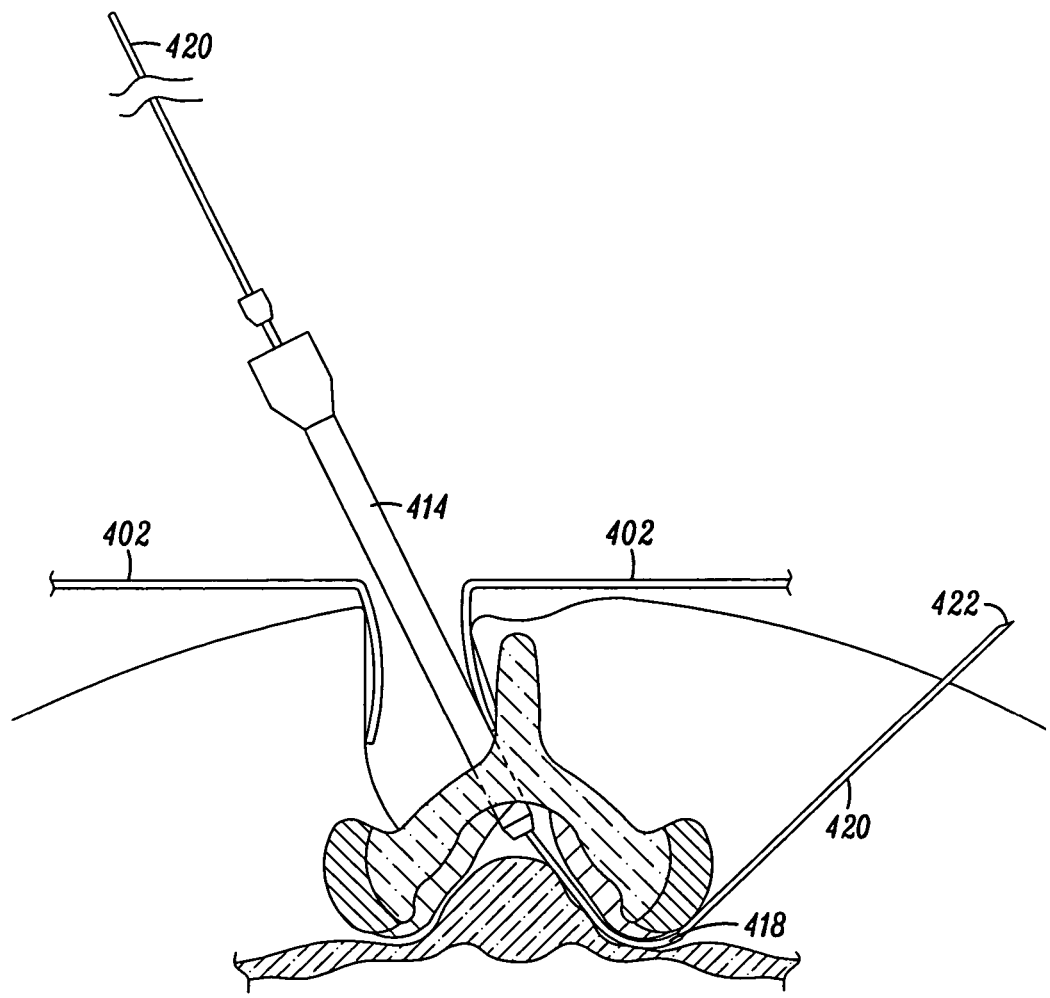
Figure 8F:
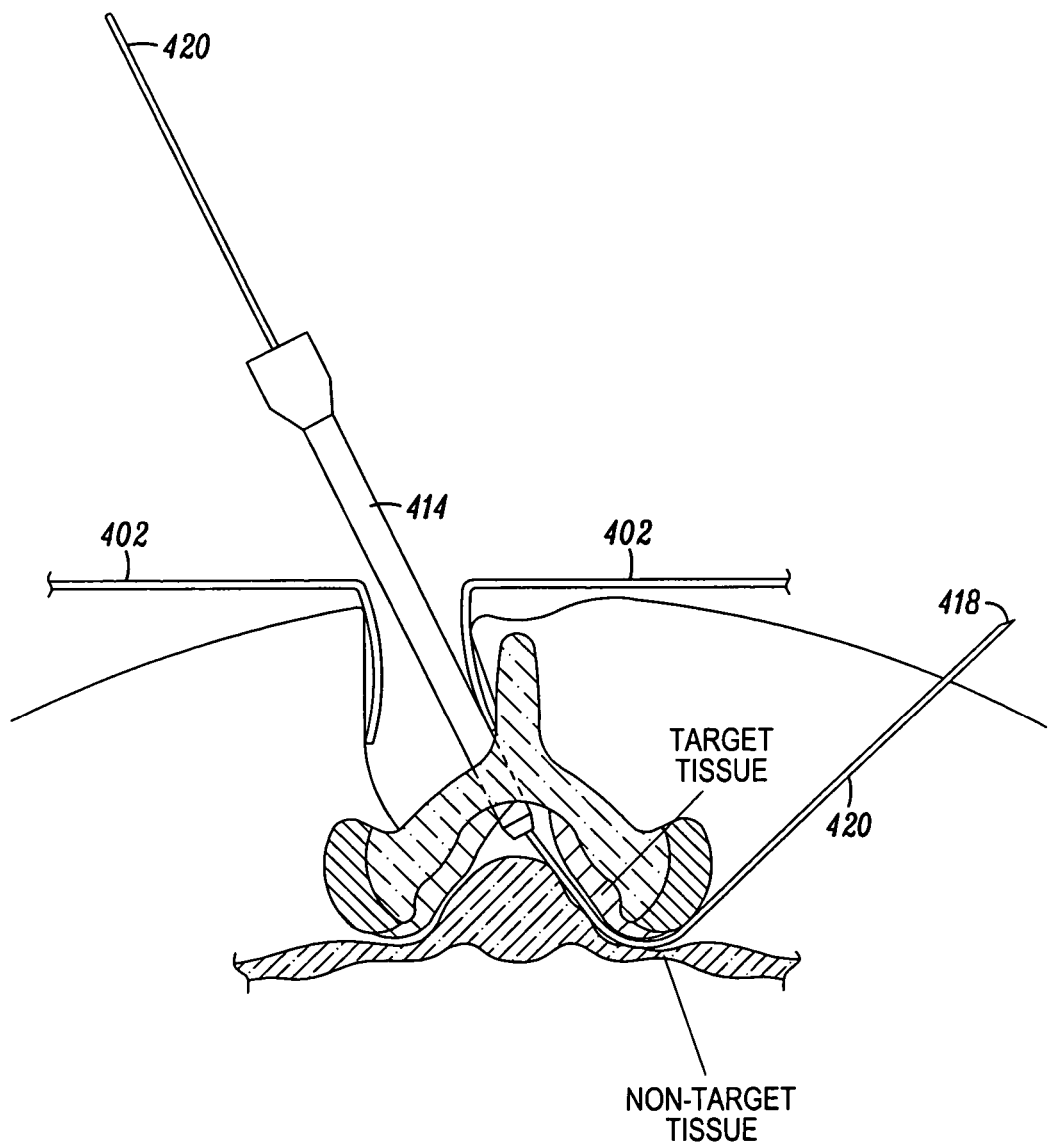

As shown in FIGS. 8D-8E, a substantially straight, flexible guidewire 420 with a sharp tip 422 may then be inserted through curved. guide device 418 and advanced so that its distal portion with sharp tip 422 extends outside the patient's back at a location separate from the open incision (FIG. 8E). Guide device 418 may then be removed, as in FIG. 8F, and in subsequent steps a tissue modification device may be inserted over guide wire 420 and through introducer sheath 414 and used to modify tissue as described in more detail above. In an alternative embodiment, a curved, flexible cannula may be inserted through the curved guide device, until it extends lateral to the neural foramen, after which a substantially straight, flexible guidewire with a sharp tip may then be inserted through curved cannula and advanced so that its distal portion with sharp tip extends outside the patient's back.

Figure 9A:
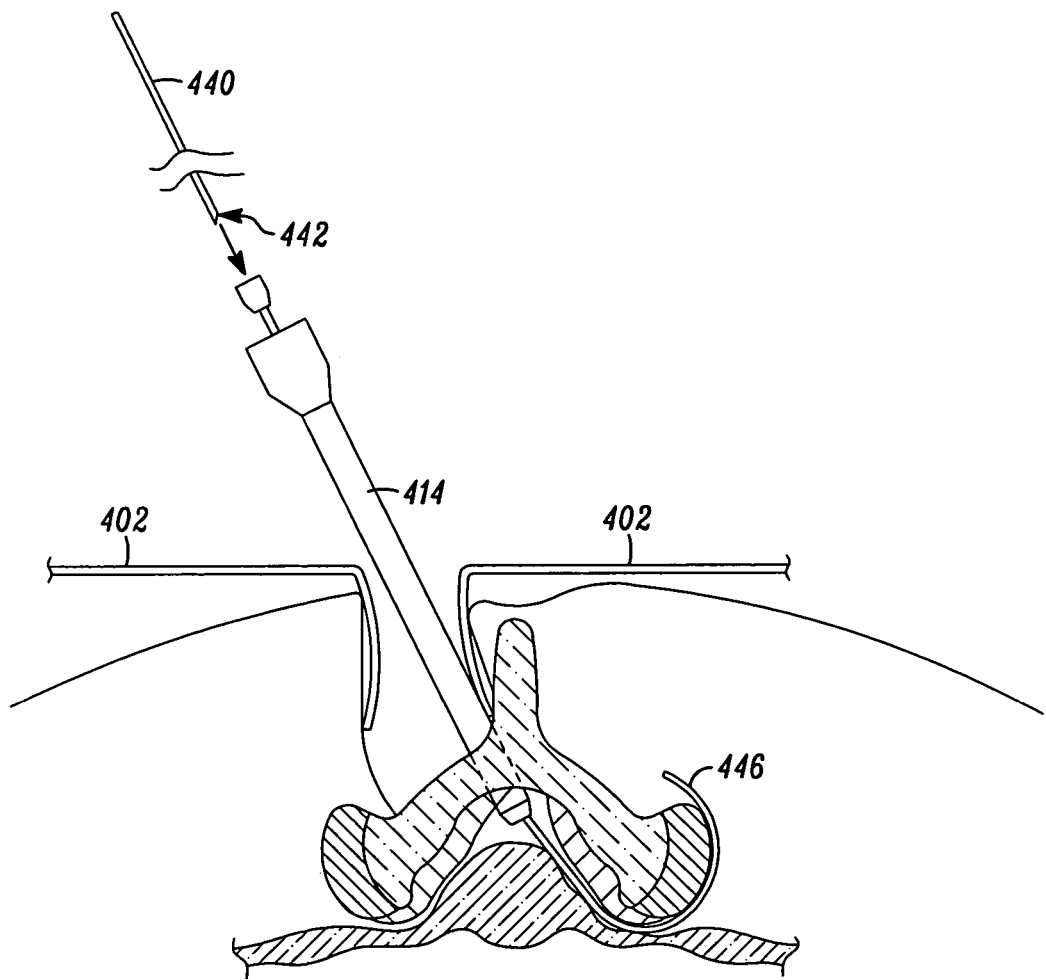
FIGS. 9A-9B are cross-sectional views of a portion of a patient's spine and back, demonstrating a method for introducing apparatus for modifying spinal tissue to an area in the spine for performing the tissue modification according to an alternative embodiment of the present invention.
Figure 9B:
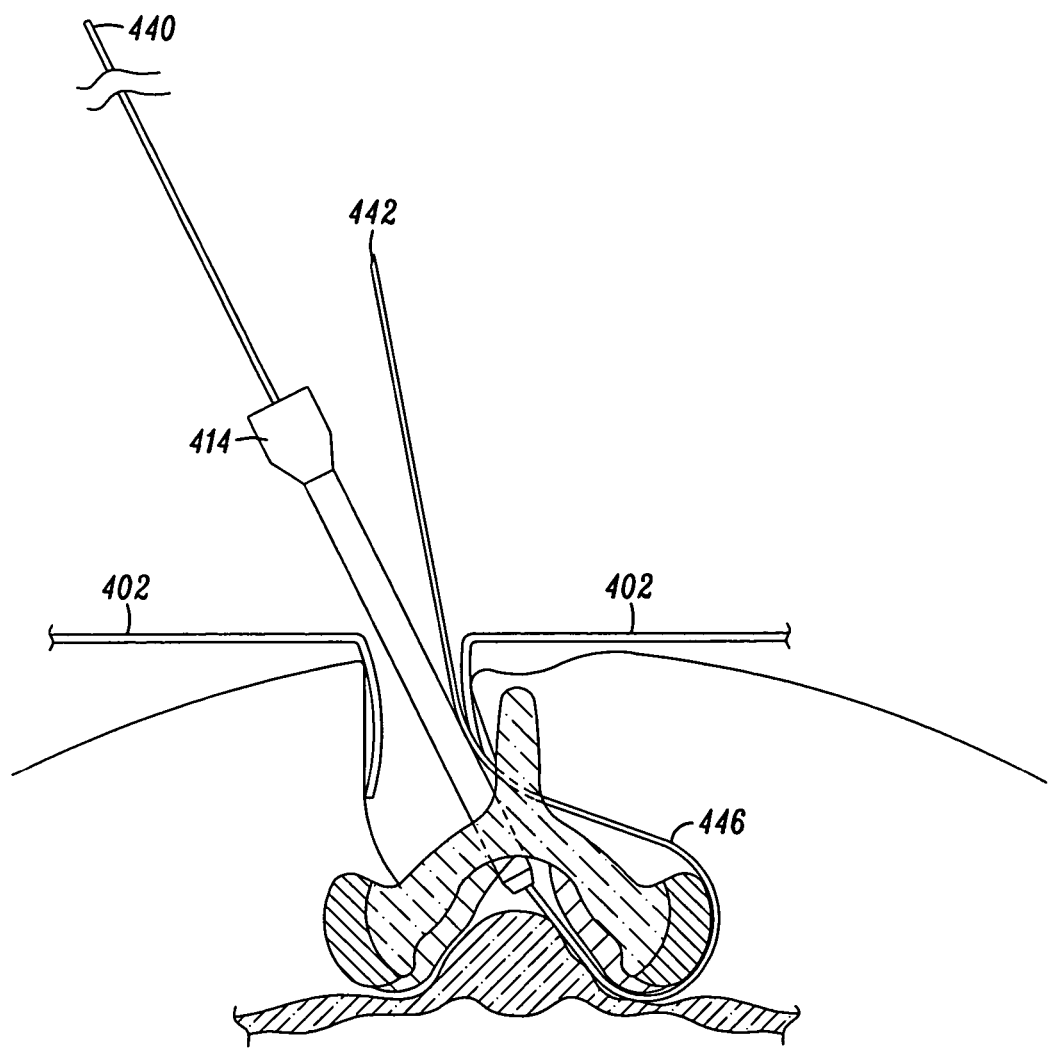

Referring now to FIGS. 9A and 9B, another alternative open surgical access method is shown. In FIG. 9A, a curved guide device 446 is shown in place through the epidural space and intervertebral foramen, and a guidewire 440 with a beveled distal tip 442 is about to be advanced through guide device 446. As shown in FIG. 9B, in this embodiment, guidewire 440 is directed by guide device 446 back through the open incision through which the various access devices are introduced. In such an embodiment, then, only one incision is created and the proximal and distal portions of one or more devices extend out of the patient's back through the same incision.

In various alternative embodiments, open surgical access may be through exposure down to a vertebral lamina, through ligamentum flavum without lamina removal, through ligamentum flavum with partial or complete lamina removal, through ligamentum flavum with or without lamina removal with partial or complete medial facet joint removal, through open exposure and out through skin laterally, through open exposure and back out through the open exposure, or through a lateral open exposure that accesses the neural foramen from the lateral side. One or more visualization devices may be used with open surgical access procedures as well as with percutaneous or other less invasive procedures. In another alternative embodiment (not shown), a tissue modification device may be placed in the patient directly, without any introduction devices.

Referring now to FIGS. 10A-10E, in the embodiments described above, the tissue modification devices 102, 202 include at least one non-tissue-modifying (or "protective") portion, side or surface. The non-tissue-modifying portion is located on tissue modification device 102, 202 so as to be positioned adjacent non-target tissue when tissue modifying members 110, 210 are facing the target tissue. The non-tissue-modification surface of the device is configured so as to not modify or damage tissue, and thus the non-target tissue is protected from unwanted modification or damage during a tissue modification procedure. Alternatively, in some embodiments, a protective surface or portion of tissue modification device 102, 202 may actually modify non-target tissue in a protective manner, such as by delivering a protective drug, coating, fluid, energy or the like to the non-target tissue.

Optionally, in some embodiments, tissue modification devices or systems may further include one or more tissue barriers (or "shields") for further protecting non-target tissues. Such barriers may be slidably coupled with, fixedly coupled with, or separate from the tissue modification devices with which they are used. In various embodiments, a barrier may be delivered between target and non-target tissues before delivering the tissue modification device, may be delivered along with the tissue modification device, or may be delivered after delivery of the tissue modification device but before the device is activated or otherwise used to modify target tissue. Generally, such a barrier may be interposed between the non-target tissue and one or more tissue modification devices to prevent unwanted damage of the non-target tissue.

Figure 10A:
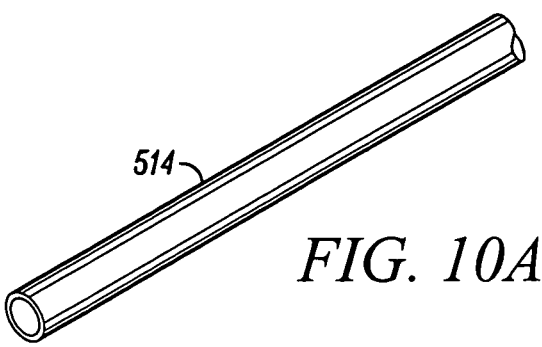
FIG. 10A is a perspective view of a distal portion of an introducer sheath according to one embodiment of the present invention.
Figure 10B:
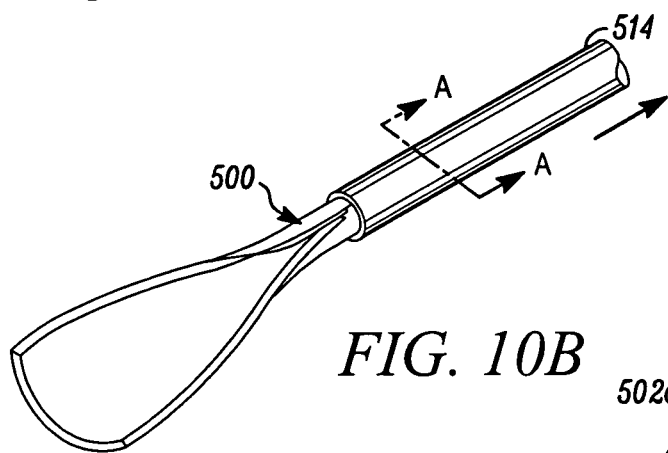
FIGS. 10B and 10C are perspective and cross-sectional views, respectively, of a tissue shield device according to one embodiment of the present invention.
Figure 10C:
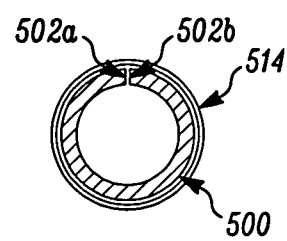
Figure 10D:
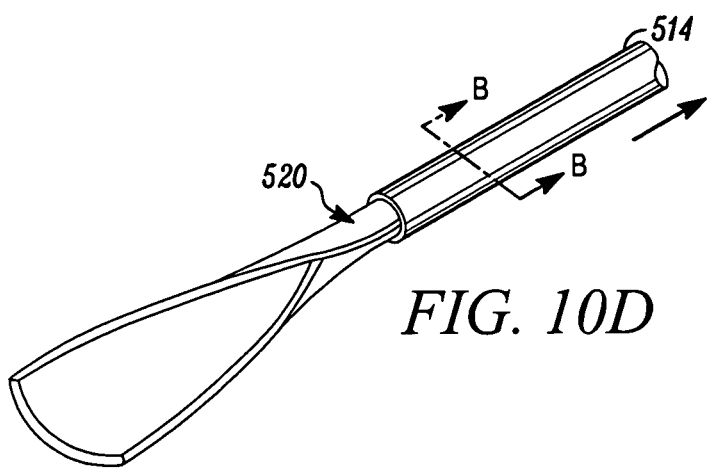
FIGS. 10D and 10E are perspective and cross-sectional views, respectively, of a tissue shield device according to an alternative embodiment of the present invention.
Figure 10E:
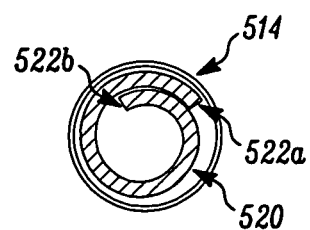

FIG. 10A shows a distal portion of an introducer device 514 through which a barrier may be introduced. FIGS. 10B and 10C show one embodiment of a barrier 500 partially deployed and in cross-section, respectively. Typically, barrier 500 will have a first, small-profile configuration for delivery to an area near non-target tissue and a second, expanded configuration for protecting the non target tissue. In various embodiments, some of which are described more fully below, barrier 500 may be configured as one piece of super-elastic or shape-memory material, as a scaffold with material draped between the scaffolding, as a series of expandable wires or tubes, as a semicircular stent-like device, as one or more expandable balloons or bladders, as a fan or spring-loaded device, or as any of a number of different devices configured to expand upon release from delivery device 514 to protect tissue. As shown in FIGS. 10B and 10C, barrier 500 may comprise a sheet of material disposed with a first end 502a abutting a second end 502b within introducer device 514 and unfurling upon delivery. In an alternative embodiment, as shown in FIGS. 10D and 10E, opposite ends 522a and 522b of a barrier 520 may overlap in introducer device 514. Generally, barrier 500, 520 may be introduced via introducer device 514 in one embodiment or, alternatively, may be introduced via any of the various means for introducing the tissue modification device, such as those described in conjunction with FIGS. 7A-7S, 8A-8F and 9A-9B. In some embodiments, barrier 500, 520 may be fixedly coupled with or an extension of a tissue modification device. Barrier 500, 520 may also include one or more lumens, rails, passages or the like for passing a guidewire or other guide member, for introducing, removing or exchanging any of a variety of tissue modification, drug delivery, or diagnostic devices, for passing a visualization device, for providing irrigation fluid at the tissue modification site, and or the like. In some embodiments, barrier 500, 520 is advanced over multiple guidewires and the guidewires remain in place during a tissue modification procedure to enhance the stability and/or maintain positioning of barrier 500, 520.

Figure 11A:
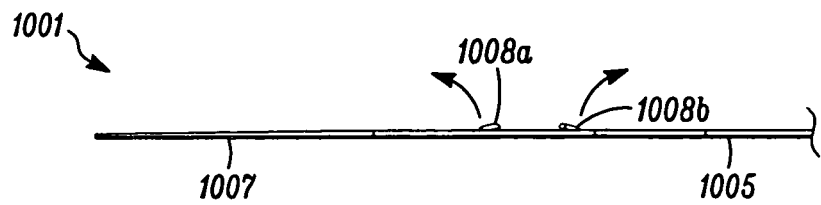
FIGS. 11A and 11B are side views of a portion of a bladed tissue modification device according to one embodiment of the present invention.
Figure 11B:
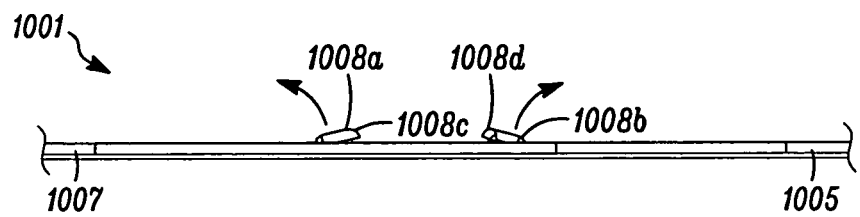

Referring now to FIGS. 11A and 11B, an alternative embodiment of a tissue modification device suitably includes an elongate body 1005 having a distal portion 1007, a distal cutting blade 1008a, and a proximal cutting blade 1008b, each blade 1008 having a cutting edge 1008c, 1008d. In this embodiment, distal cutting blade 1008a and proximal cutting blade 1008b may be rotated away from elongate body 1005 to further expose cutting edges 1008c, 1008d. The height of cutting edges 1008c, 1008d relative to the elongate body 1005 may be used, for example, to control the depth of the cut into hard and/or soft target tissue.

The embodiment shown in FIGS. 11A and 11B, as well as many of the embodiments described below, include two movable, opposing blades 1008a, 1008b, which may be moved toward one another to cut tissue. Alternative embodiments, however, may include two immobile blades, one movable blade and one immobile blade, one movable blade, one immobile blade, more than two immobile blades facing in one direction, more that two immobile blades facing in different directions, a movable blade and a backstop against which the blade may be driven, or any other suitable combination of movable and/or immobile blades. Furthermore, any blade of any given embodiment may have any suitable shape, size and overall configuration. In some embodiments, blades may be flat, while in others they may be curved, squared off, ridged, bent or the like. Blades may be long or short, multiple blades may be aligned closely one after the other, such as in a typical multi-blade razor used for shaving a face, multiple blades may be disposed apart from one another by several millimeters or even centimeters, and/or the like. Blades may have any suitable amount of sharpness or dullness, and in some embodiment a combination of sharper and duller blades may be used. Therefore, although exemplary embodiments of blades are described in detail above and below, any other suitable blades or combinations of blades may be substituted in various embodiments, without departing from the scope of the present invention.

In the embodiments described previously or in any other embodiments described herein, blades may be fabricated from metals, polymers, ceramics, composites or any other suitable material or combination of materials. According to various embodiments, suitable metals for blades may include, but are not limited to, stainless steel, nickel-titanium alloy, or cobalt-chromium alloy, for example, Elgiloy™ (Elgin Specialty Metals, Elgin, Ill., USA), Conichrome™ (Carpenter Technology, Reading, Pa., USA), or Phynox™ (Imphy S A, Paris, France). Polymer materials include nylon, polyester, Dacron™, polyethylene, acetal, Delrin™ (DuPont), polycarbonate, nylon, polyetheretherketone (PEEK), and polyetherketoneketone (PEKK). In some embodiments where polymers are used, such polymers may be glass-filled or carbon-filled to add strength and stiffness. Ceramics may include, but are not limited to, aluminas, zirconias, and carbides. Blades may be manufactured using skills known in the art, for example, metal injection molding (MIM), CNC machining, injection molding, grinding, electrodischarge madhining (EDM), sheet metal bending, etching, electrodeposition, or the like. Pull wires 1011 may similarly be fabricated from any suitable material and may have any of a number of suitable shapes and dimension. In some embodiments, for example, pull wires 1011 may be made from metal or polymer and may have substantially circular, oval, rectangular or square cross sections, although this is by no means a comprehensive list. In some embodiments, pull wires 1011 may range in diameter from about 0.001 inches to about 0.10 inches, and more preferably between about 0.010 inches and 0.020 inches. Other portions of a tissue modification device, such as a cover over one or more blades or other features, may be made of any suitable material now known or hereafter discovered. A blade cover, for example, may be fabricated in various embodiments of one or more polymeric materials, such as nylon, silicone, polyetheretherketone (PEEK), polyetherketoneketone (PEKK), polytetrafluoroethylene (PTFE), polyurethane (Tecothane,), Pebax (co, USA), polycarbonate, Delrin (co, USA), high-density polyethylene (HDPE), low-density polyethylene (LDPE), HMWPE, UHMWPE, or the like. In some embodiments, one or more materials may be chosen for their compatibility with one or more imaging techniques or systems, such as magnetic resonance imaging (MRI), for example.

In various embodiments, elongate body 1005 may include one or more hollow chambers (not shown) at or near a distal portion of body 1005. Such hollow chamber(s) may serve any of a number of suitable functions. In some embodiments, for example, a chamber may be located distal and/or proximal to one or more blades 1008a, 1008b and may serve to collect removed tissue during and/or after a tissue modification procedure. In some embodiments, one or more blades 1008a, 1008b may help push removed tissue into such a chamber or chambers. In some embodiments, one or more chambers may house one or more blades 1008a, 1008b, such that blades 1008a, 1008b are housed within the chamber(s) while elongate body 1005 is passed into a patient and between target and non-target tissues. Once elongate body 1005 is in a desired position, blades 1008a, 1008b may then be deployed out of one or more windows or similar openings in the chamber(s) to remove or otherwise modify tissue. Such chambers may include, in various embodiments, a hollow distal portion or nosecone of elongate body 1005, a hollow portion of elongate body 1005 just proximal to proximal cutting blade 1008b, and/or the like.

Figure 12A:
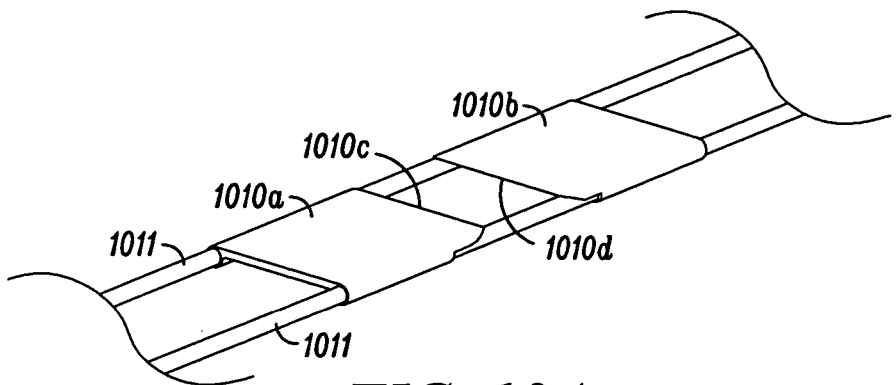
FIGS. 12A and 12B are perspective views of a portion of a bladed tissue modification device according to an alternative embodiment of the present invention.
Figure 12B:
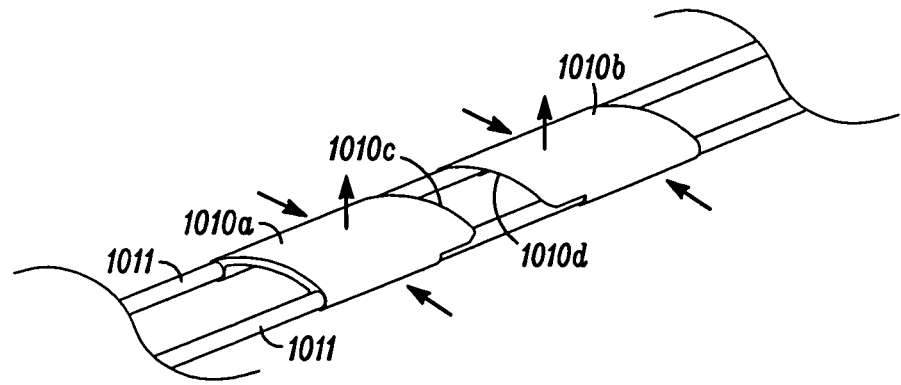

Another embodiment, as shown in FIGS. 12A and 12B, suitably includes a thin distal cutting blade 1010a and a thin proximal cutting blade 1010b, each blade 1010 having a cutting edge 1010c, 1010d and both blades 1010 being attached to two parallel pull wires 1011. In FIG. 12A, blades 1010a, 1010b are shown their flat configuration. In one embodiment, as shown in FIG. 12B, when a load is applied that is planar to pull wires 1011 and normal to the long axis of pull wires 1011, thin blades 1010a, 1010b flex or bow out of plane to increase the height of the cutting edges 1010c, 1010d.

Figure 13A:
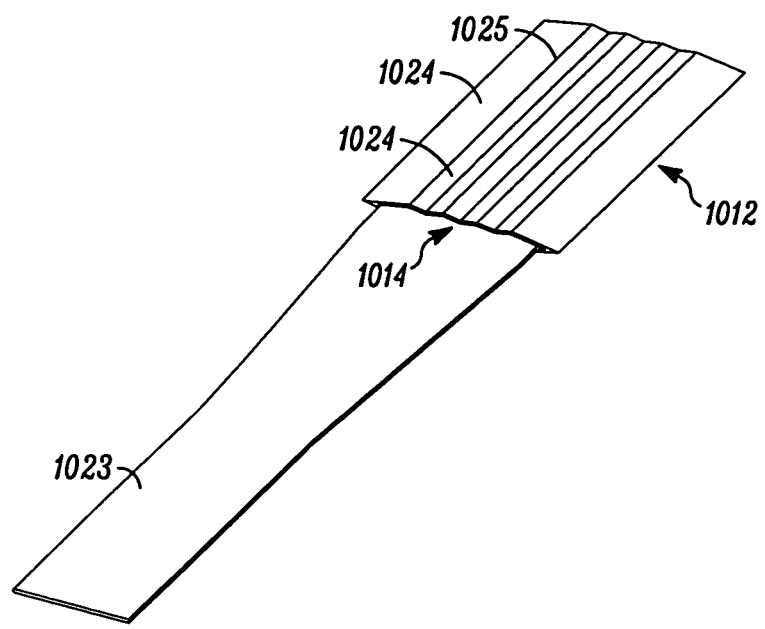
FIGS. 13A and 13B are perspective views of a portion of a bladed tissue modification device according to an alternative embodiment of the present invention.
Figure 13B:
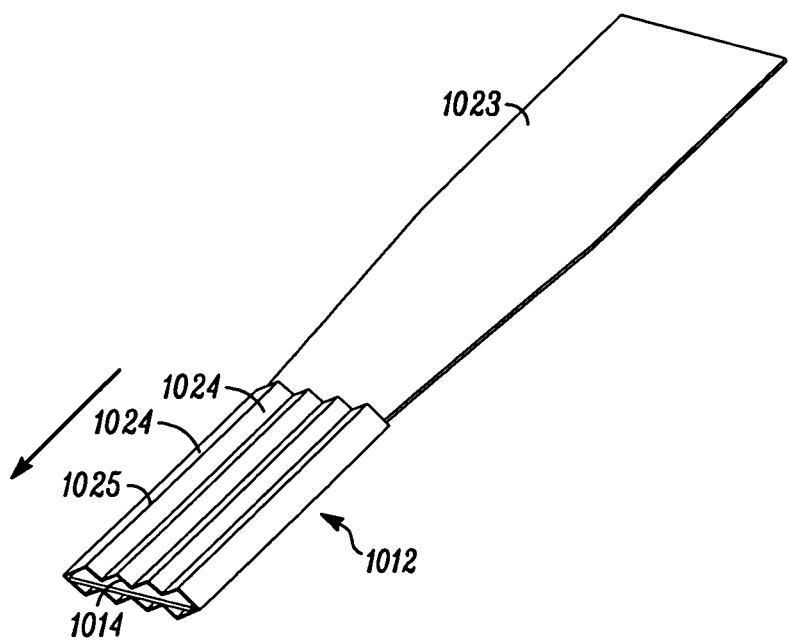

Referring now to FIGS. 13A and 13B, another alternative embodiment of a blade 1012 that changes shape as it translates along a device is shown. Blade 1012 includes multiple flat members 1024 joined at edges 1025, which may form bends, creases, folds, or hinges that allow blade 1012 to widen (FIG. 13A) and contract (FIG. 13B). Blade 1012 includes a cutting edge 1014, which may be formed using methods known in the art, for example, grinding, molding, cutting, EDM machining, etching, laser cutting, electropolishing, electrodeposition, etc. In various embodiments, blade 1012 may be made from metal, polymer, or a combination of both. In some embodiments, blade 1012 may be translated along a central member 23 that causes blade 1012 to widen and contract at various locations along central member 23. When blade 1012 is located over a wider section of central member, as in FIG. 13A, blade 1012 has a flatter, wider configuration. When blade 1012 slides or otherwise translates along central member 1023 to a narrower section, as in FIG. 13B, blade 1012 assumes a taller, narrower configuration. Such a taller configuration may facilitate cutting tissue with blade edge 1014, in some embodiments. Edges 1025 of blade 1012 allow it to change shape more readily between the wider and narrower configurations, and the bends or ridges formed in blade 1012 in the narrower configuration (FIG. 13B) may help limit the amount of material that is removed with each pass of blade 1014 along a surface of target tissue.

Figure 14A:
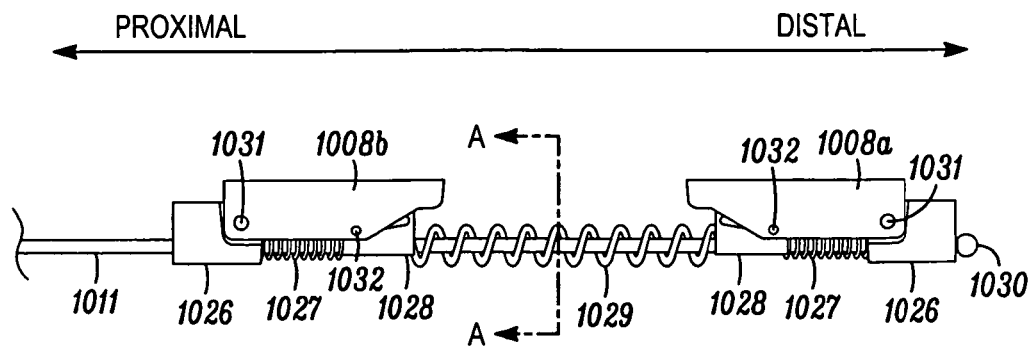
FIGS. 14A-14D are side, end-on cross-sectional, top, and lateral cross-sectional views, respectively, of a blade mechanism of a tissue modification device according to one embodiment of the present invention.

Referring now to FIGS. 14A-14D, one embodiment of a blade system for a tissue modification device is shown. FIG. 14A is a side view showing distal cutting blade 1008a and proximal cutting blade 1008b, each of which is free to pivot about an external pin 1031 that may be rigidly fixed to an external support block 1026 that is free to slide along a pull wire 1011. An internal pin 1032 may be contained within an angled slot 1033 (shown in FIG. 14D) in an internal support block 1028 that freely slides along pull wire 1011. A wire stop 1030 is securely fixed to the end of pull wire 1011 to prevent pull wire 1011 from pulling through distal external support block 1026 as axial force is applied to pull wire 1011. In various embodiments, wire stop 1030 may include but is not limited to a mechanical squeeze-type clamp, a ball formed at the end using a laser, TIG welder, or torch, a crimped hypotube, a sleeve with a set-screw, a loop, bend or twist in the wire, or the like. A pair of external springs 1027 may maintain blades 1008a, b in a low-profile (or "flat") configuration. An internal spring 1029 may act to separate blades 1008a, 1008b.

Figure 14B:
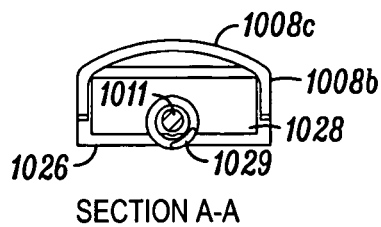

FIG. 14B provides a cross-sectional view along the line A-A in FIG. 14A. Proximal cutting blade 1008b is shown to have a curved profile, and centrally located pull wire 1011 and internal spring 1029 are also shown. Internal support block 1028 and external support block 1026 remain within the profile of proximal cutting blade 1008b. Cutting blade edge 1008c is positioned in a low profile configuration.

Figure 14C:
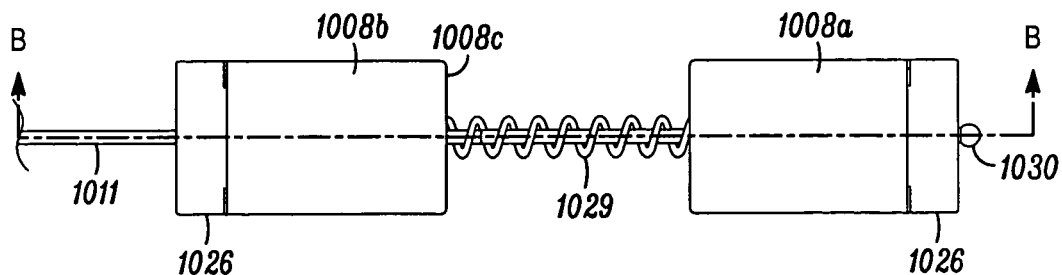

As shown in FIG. 14C, in one embodiment, the width of distal blade 1008a and proximal blade 1008b may be approximately the same as the width of external support block 1026. Pull wire 1011 may be centrally located to facilitate uniform movement of the cutting blade 1008a and therefore uniform cutting with cutting blade edge 1008c.

Figure 14D:
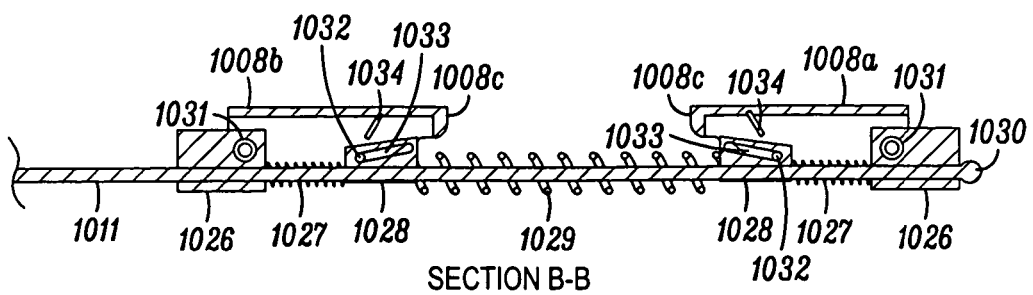

In the cross-sectional view of FIG. 14D, an angled slot 1033 is shown that constrains internal pin 1032 that controls the height of blades 1008a, 1008b at a given. axial displacement of internal support block 1028 relative to external support block 1026. In some embodiments, a baffle 1034 may be used as a one-way mechanism for debris transport down the open channel of blade 1008a, 1008b.

Figure 15A:
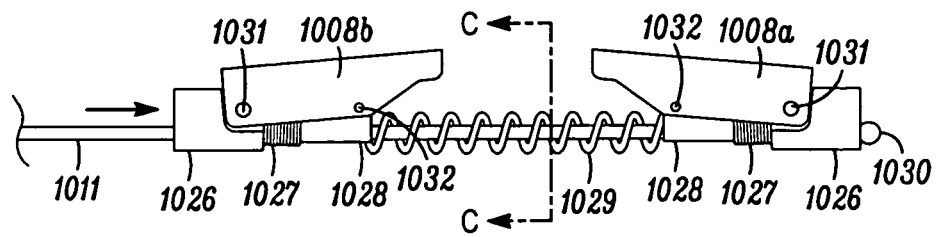
FIGS. 15A-15D are side, end-on cross-sectional, top, and lateral cross-sectional views, respectively, of the blade mechanism of FIGS. 14A-14D, shown with the blades disposed at an angle, relative to the mechanism according to one embodiment of the present invention.
Figure 15B:
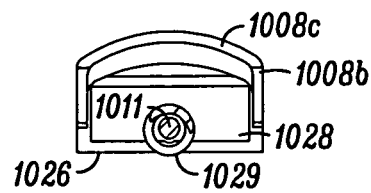
Figure 15C:
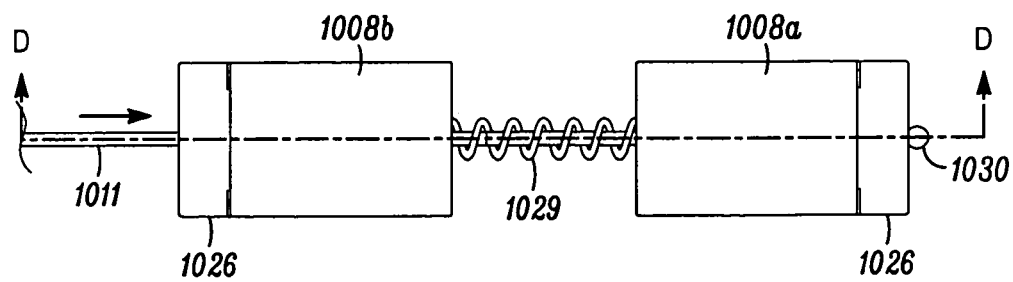
Figure 15D:
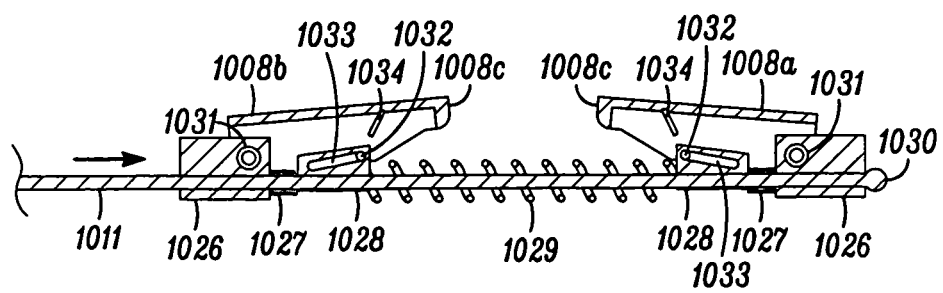

Referring now to FIGS. 15A-15D, in one embodiment, as proximal external support block 1026 is driven distally towards wire stop 1030, external springs 1027 compress to increase the height of the proximal and distal cutting blades 1008a, 1008b, as shown in side view in FIG. 15A. External springs 1027 may have a lower spring rate (lb./in.) than that of internal spring 1029, such that external springs 1027 displace more readily than internal spring 1029 during the initial loading of the mechanism in order to preferentially drive blades 1008a, 1008b upward. This increase in blade height may help control the amount of tissue material that will be removed during a cutting cycle. The blade height can be adjusted by adjusting the length, angle, and endpoint positions for angled slot 1033. To help support blades 1008a, 1008b during the cuffing process, blades 1008a, 1008b may stop at the limits of the angled slot 1033 and may also be limited by the angled cut on the sides of external support blocks 1026 near external pin 1031.

Figure 16A:
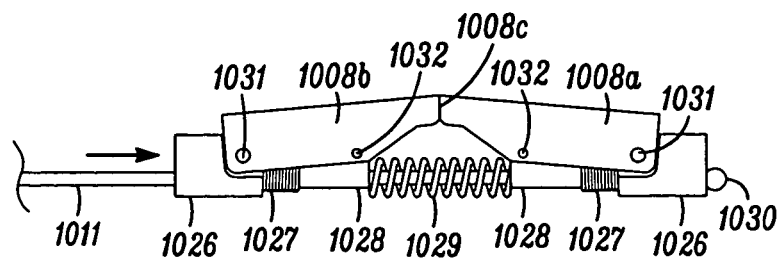
FIGS. 16A-16C are side, top, and lateral cross-sectional views, respectively, of the blade mechanism of FIGS. 15A-15D, shown with the blades disposed at an angle with their cutting edges brought together according to one embodiment of the present invention.
Figure 16B:
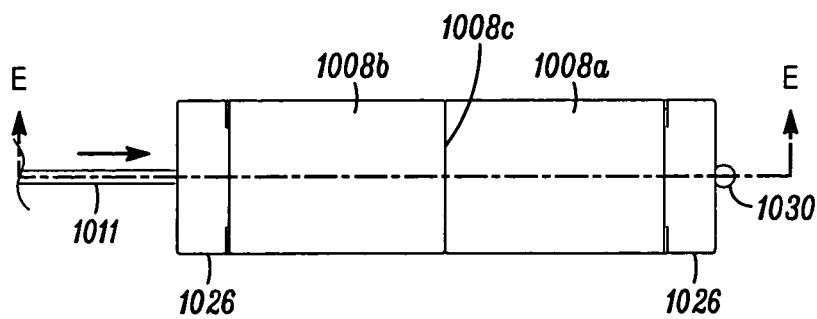
Figure 16C:
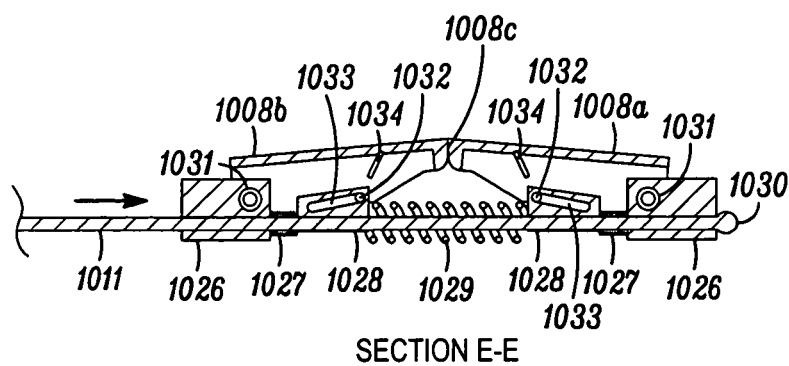

With reference now to FIGS. 16A-16C, in one embodiment blades 1008a, 1008b may be made to rotate to a desired height, such as their maximum height, and may then be driven toward one another by applying an additional load to further compress internal spring 1029, as depicted in side-view in FIG. 16A. In some embodiments, blades 1008a, 1008b are driven together until cutting blade edges 1008c contact each other to complete a cutting cycle. In some embodiments, relative spring rates for external spring 1027 and internal spring 1029 may be customized/selected to provide a desired cutting action and penetration behavior for blades 1008a, 1008b into target tissue. After a cutting cycle is complete, blades 1008a, 1008b may be driven apart and further pushed into a low profile state by internal spring 1029 and external springs 1027. Baffle 1034 may be displaced as debris is driven into the blade channel, and baffle 1034 then may return to its original position to hold the debris in place. In some embodiments, for example, baffle 1034 may include a metal tab or a polymer flap molded into blade 1008a, 1008b. An alternative debris capture mechanism is shown in the cross-sectional view of blade 1008 depicted in FIG. 17F. Multiple ramps 1034a and stops 1034b allow debris to slide away from cutting edge 1008c but prevent the debris from sliding back.

Figure 17A:
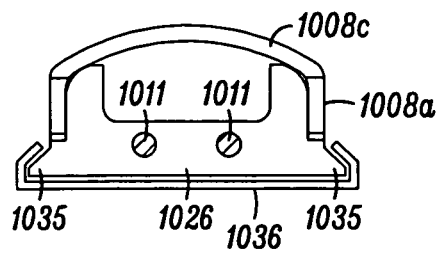
FIGS. 17A-17D are cross-sectional end-on views of various embodiments of a blade mechanism of a tissue modification device with a track having different configurations in the various embodiments.
Figure 17B:
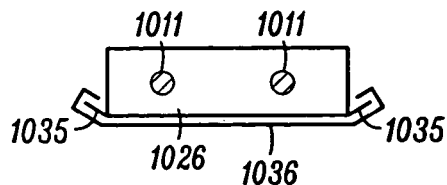
Figure 17C:
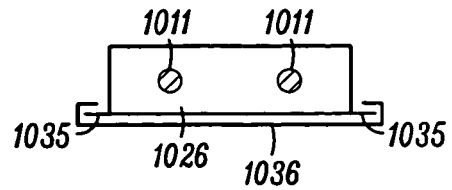
Figure 17D:
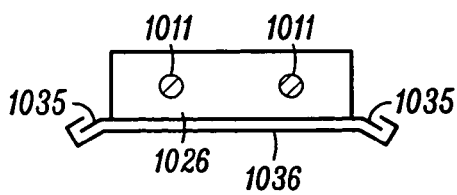
Figure 17F:
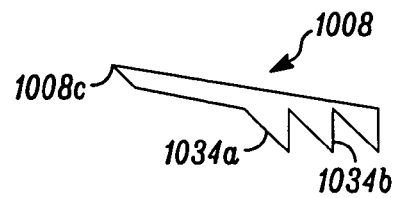
FIG. 17F is a cross-sectional view of a blade with means for directing cut tissue according to one embodiment of the present invention.

Referring to FIG. 17A, in one embodiment, to prevent a cutting blade 1008a from rotating about the axis of a single pull wire 1011 and/or to allow for more force or more distributed force along cutting edge 1008c, multiple pull wires 1011 may be used to actuate the blade mechanism. In addition, external support block 1026 may optionally include ridge features 1035 that slidably engage with a track 1036 that may serve as an anti-rotation mechanism and may also provide additional strength and stiffness along the length of the blade mechanism. In various embodiments, orientation of such ridge features 1035 may be varied. For example, ridge feature 1035 may be folded inward as in FIG. 17B, flat as in FIG. 17C or folded outward as in FIG. 17D. In various embodiments, ridge feature 1035 have any suitable shape or configuration, such as but not limited to a round, square, dove-tailed, rectangular, or triangular cross-sectional shape.

Figure 18A:
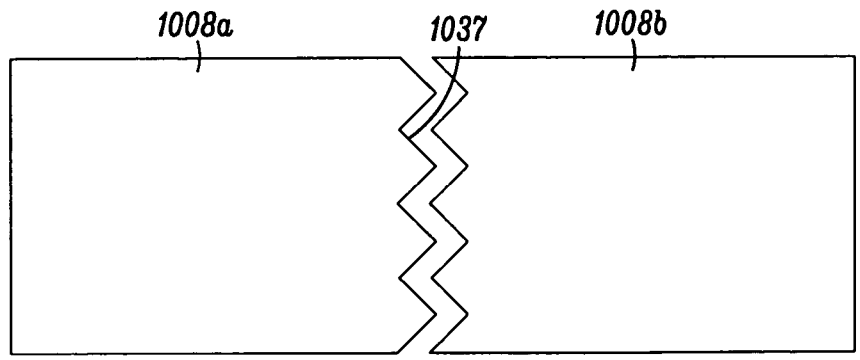
FIGS. 18A and 18B are top views of blades having alternative configurations of teeth according to alternative embodiments of the present invention.
Figure 18B:
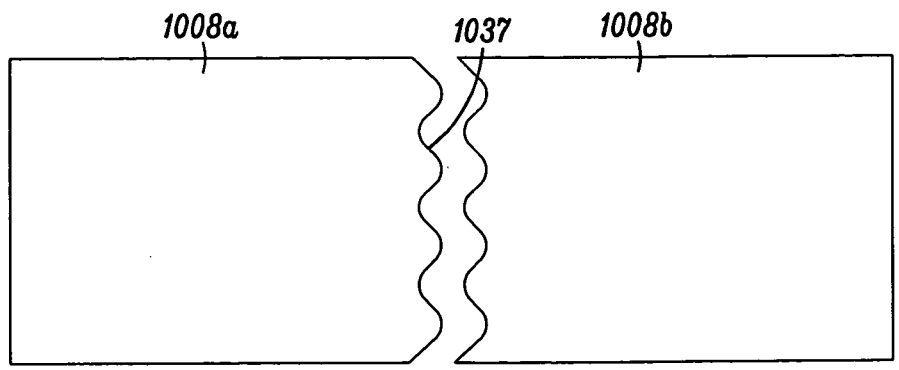

With reference now to FIGS. 18A and 18B, in various embodiments the cutting edges of blades 1008a, 1008b may have teeth 1037 that facilitate engagement with a smooth, curved, and/or hard target tissue, such as bone. One embodiment, as in FIG. 18A, may include pointed teeth 1036, while an alternative embodiment, as in FIG. 18B, may include rounded teeth 1037. Of course, any other suitable configuration may be substituted in various alternative embodiments.

Figure 18C:
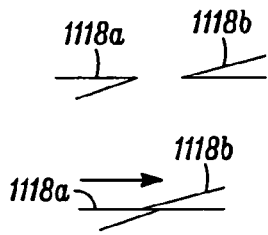
FIGS. 18C-18G are side views of various blade-blade and blade-backstop combinations according to various embodiments of the present invention.
Figure 18D:
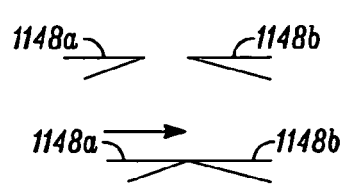
Figure 18E:
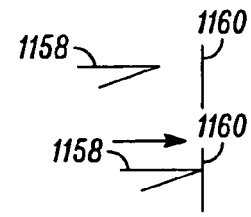
Figure 18F:
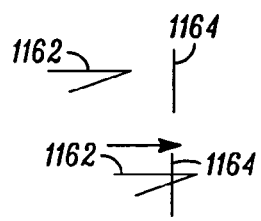
Figure 18G:
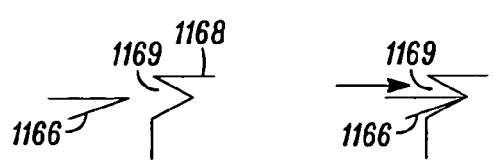

Referring now to FIGS. 18C-18G, in various embodiments, the interaction of cutting edges of two blades or one blade and a backstop may effectively modify tissue with any number of different actions. FIG. 18C depicts the cross section of two opposing blades 1118a, 1118b, which are slightly offset with their respective bevels angled opposite of each other. This may create a shearing action when blades 1118a, 1118b are brought together and pass each other as shown in the lower portion of the FIG. 18C. In FIG. 18D two blades 1148a, 1148b are in plane with similar bevels. The cutting edges of these blades 1148a, 1148b come in contact to bite tissue when blades 1148a, 1148b are brought together. In another embodiment, as in FIG. 18E, one blade 1158 may be brought into contact with a backstop 1160, which in one embodiment comprises a hard flat plane. FIG. 18F depicts a single blade 1162 brought into contact with a compliant flat plane backstop 1164. Contact of blade 1162 with such a backstop 1164 may create both a pinching and a shearing effect on tissue. In yet another embodiment, as in FIG. 18G, a single blade 1166 may be brought against the a backstop 1168 having a concave pocket 1169. This may also create both a shearing and a pinching action on targeted tissue.

Figure 19A:
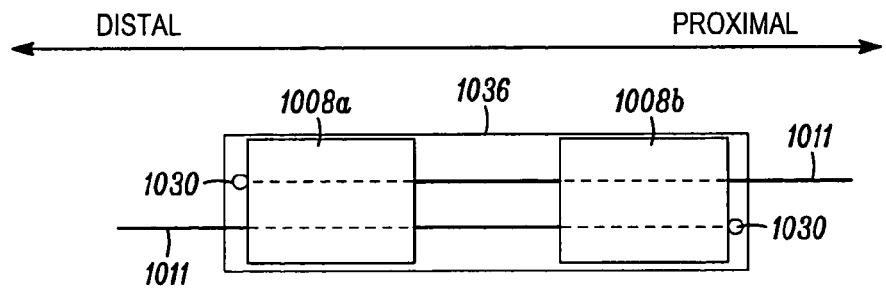
FIGS. 19A and 19B are top views of a blade and pull wire mechanism according to one embodiment of the present invention.
Figure 19B:
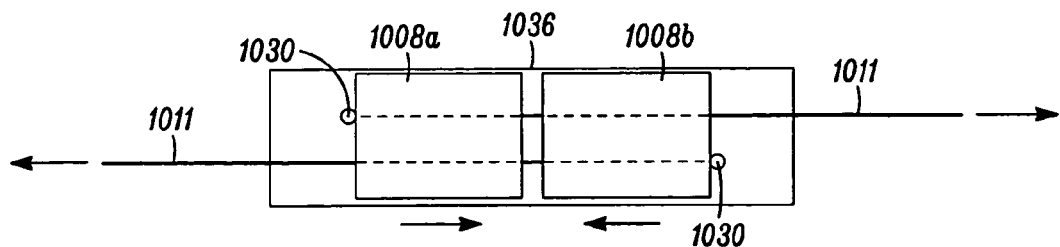

Referring to FIGS. 19A and 19B, in one embodiment, distal cutting blade 1008a and proximal cutting blade 1008b (or external support blocks 1026 that in turn are fitted with blades that pivot about the external pin 1031) may be slidably engaged in a track 1036, two pull wires 1011 may be mounted in opposite directions, and wire-stops 1030 may be located on the outside of opposite blades 1008a, 1008b, as shown in top-view in FIG. 19A. By applying a force to the pull wires 1011, blades 1008a, 1008b are drawn toward the center of track 1036, as depicted in FIG. 19B.

Figure 20A:
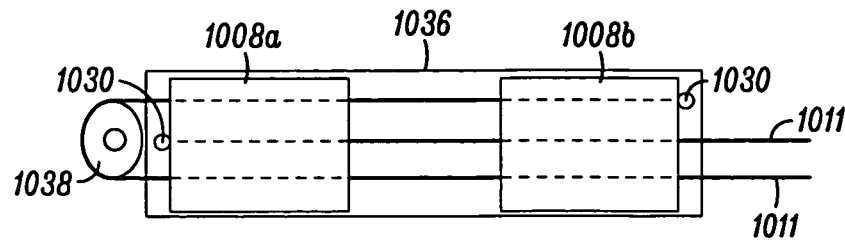
FIGS. 20A and 20B are top views of a blade and pull wire mechanism according to an alternative embodiment of the present invention.
Figure 20B:
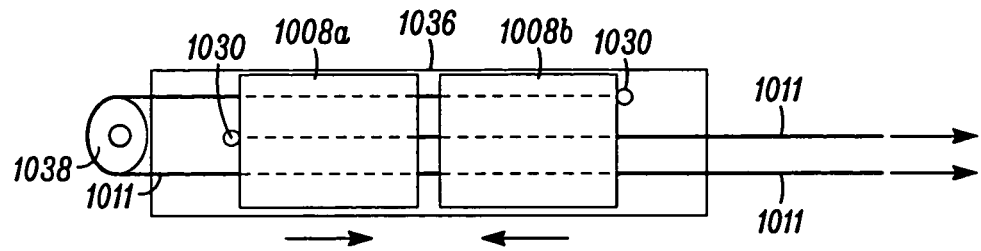

In an alternative embodiment, as in FIGS. 20A and 20B, two pull wires 1011 may be actuated from one end of a tissue modification device. In such an embodiment, a pulley 1038 (or capstan) may be used to redirect one of the wires 1011, as shown in top-view in FIG. 20A, so that the two pull wires 1011 are aligned. As depicted in FIG. 20B, actuating pull wires 1011 from the one end causes blades 1008a, 1008b to move toward the center of track 1036.

In one alternative embodiment (not pictured), similar to that in FIGS. 20A and 20B, a first pull wire may be constrained on one side of a blade by a wire stop to provide a closing motion of the blade toward a stationary blade. A second pull wire may be constrained on an opposite side of the blade by a wire stop and guided around a pulley or capstan to direct the pull wire in the same direction as the first pull wire. This second pull wire may be used to provide an opening motion of the blade away from stationary blade.

Figure 21A:
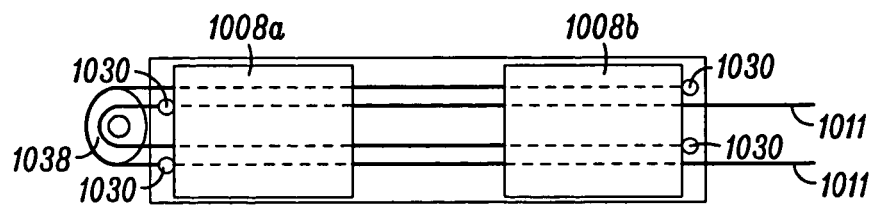
FIGS. 21A and 21B are top views of a blade and pull wire mechanism according to an alternative embodiment of the present invention.
Figure 21B:
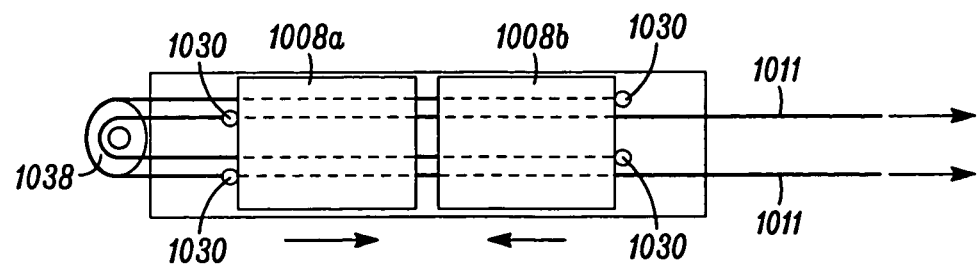

Referring now to FIGS. 21A and 21B, in another alternative embodiment, to balance or distribute the applied load on blades 1008a, 1008b more evenly (to prevent blades 1008a, 1008b from binding while sliding with or without the track) and still have pull wires 1011 actuate from one end of the device, the two pull wires 1011 may both be redirected around a double grooved pulley 1038 (or capstan), as shown in top-view in FIG. 21A. Two additional wire stops 1030 may be added to an edge of each blade 1008a, 1008b. Applying force to the pull wires 1011 causes blades 1008a, 1008b to move toward one another.

As depicted in FIGS. 22A-22C, in another embodiment, distal cutting blades 1008a and proximal cutting blades 1008b may be housed within an enclosure 1039 that has an opening 1041 and a ramp 1042 to facilitate deployment of blades 1008a, 1008b out of window. Blades 1008a, 1008b are shown in their undeployed positions in FIG. 22A. In FIG. 22B, as blades 1008a, 1008b are driven inward by an applied force via one or more wires, flexures, or mechanisms, blades 1008a, 1008b rotate about a base pivot 1040 and are driven through opening 1041 along ramp 1042 and are exposed out of enclosure 1039. FIG. 12C shows blades 1008a, 1008b in contact with one another as enclosures 1039 are driven inward to complete a cutting cycle. In some embodiments, springs (not shown) may be used to drive the mechanism apart, similar to the mechanism described in FIG. 4A, such that blades 1008a, 1008b would lay flush within enclosure 1039 once the applied force is removed.

In some embodiments, as in FIGS. 23A and 23B, blades 1008a, 1008b may also be directed to translate along an axis normal to pull wire 1011 by having pull wire 1011 change its applied direction by 90 degrees by means of a pulley 1038 (or capstan).

Referring to FIGS. 24A and 24B, in one embodiment, a tissue modification device 1001 may include endcaps 1043 on each end of an elongate body 1005, which endcaps 1043 are attached to pull wires 1011 in order to actuate the distal and proximal cutting blades 1008a, 1008b. In addition, as depicted in FIG. 14B, elongate body 1005, in some embodiments, may be partially flexible at various locations along its length or, in some embodiments, along its entire length. The embodiment depicted in FIG. 14B shows two flexion points where elongate body 1005 may be flexed to bend around anatomical structures. In some embodiments, encaps 1043 may be tapered to facilitate passage of device 1001 through a small incision. Encaps 1043 and elongate body 1005 may also optionally be configured to accommodate a guidewire for over-the-wire advancement to target tissue.

In one embodiment, and with reference now to FIGS. 25A and 25B, endcaps 1043 may nest within a simple T-handle mechanism 1044 that is fitted within a handgrip 1045, as demonstrated in FIG. 25A. T-handle mechanism 1044 may be displaced to pull endcap 1043 that is in turn connected to pull wire 1011, as handgrip 1045 provides counter-traction to elongate body 1005. Other quickly attached and separated handle mechanisms that allow tensioning and wire actuation and/or wire constraint may alternately be used.

Referring now to FIGS. 26A and 26B, some embodiments may optionally provide for lateral movement and/or control of lateral movement of one or more cutting blades. As shown in front-view in FIG. 26A, in one embodiment a cam 1046 may be rigidly fixed to a rotatable control rod 1048 that freely rotates within a support block 1049. Support block 1049 has raised features 1047 that constrain cam 1046. Support rods 1050 prevent axial displacement of support block 1049 while allowing it to translate from side to side. A support frame 1051 may contain the mechanism and may be fitted to the body of the tissue modification device. Support block 1049 may translate to the left, for example, as depicted in FIG. 26B, as control rod 1048 is rotated counter-clockwise. According to various embodiments, any of the previously disclosed cutting mechanisms may be fitted to support block 1049 to facilitate controlled lateral displacement of the cutting mechanism as actuated by control rod 1048 for cutting tissue.

FIGS. 27A and 27B show an alternative embodiment including a rotatable control rod 1048 that freely rotates within support frame 1051. Control rod 1048 is rigidly fixed to a fork or yoke 1052 that captures a positioning pin 1053. As yoke 1052 is rotated counterclockwise, for example, support block 1049 may be displaced to the right, as depicted in FIG. 27B.

Referring to top-view FIGS. 28A and 28B, in one alternative embodiment, instead of rotating a rod about the long axis of a tissue modification device, control wires 1011 may be secured to a base pulley 1054 that is rigidly fixed to a control linkage 1055. By pulling on a control wire 1011, support block 1049 may be translated to the left, as in FIG. 28B, or to the right, as in FIG. 28A.

With reference now to FIGS. 29A-29C, in some embodiments it may be advantageous to include one or more guiding or steering features on an elongate body of a tissue modification device, to facilitate guiding or steering of the body and/or one or more tissue modification members. In some embodiments, such guiding or steering features may be located adjacent or near tissue modifying members and may facilitate moving such members laterally back and forth or in any of a number of directions and/or may facilitate urging the tissue modifying members into target tissue. In other embodiments, guiding or steering members may be located along an elongate body at one or more locations distant from the tissue modifying members.

As shown in FIGS. 29A-29C, in one embodiment, a tissue modifying portion 1056, such as a blade mechanism, may be coupled with a deployable wire loop 1058 that may facilitate guiding or directing portion 1056 by bowing outward to press against tissue. A top-view depicted in FIG. 29A shows tissue modifying portion 1056 (possibly polymer or hypotube), which may contain a push wire 1057 constrained at the distal end. When a force is applied to push wire 1057, the portion of the wire contained in tissue modifying portion 1056 bows out to create a side-loop 1058, as depicted in FIG. 29B. A small feature on the end of the wire like a formed ball (or clamp) 1059 can be constrained at distal end of tissue modifying portion 1056. Alternately, as in FIG. 29C, wire 1057 may be pulled to bow out a portion of side loop 1058. In either case, side loop 1058 may push against tissue on one side to force tissue modifying portion 1056 laterally to the other side.

Referring to FIGS. 30A and 30B, in some embodiments, side-loop 1058 may be toggled from side to side by means of a distal tip 1060 to facilitate control and/or steering of tissue modifying portion 1056.

Figure 31A:
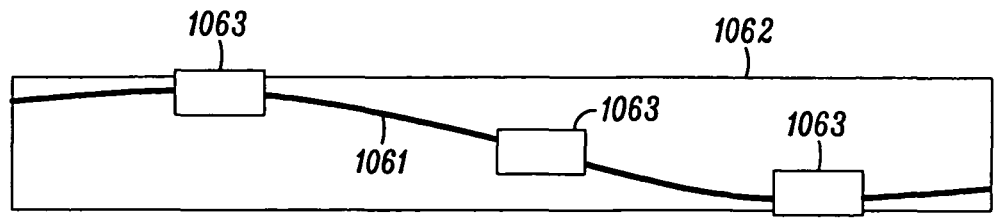
FIGS. 31A and 31B are top and cross-sectional side views, respectively, of a portion of a tissue modification device including a track along which one or more blades slide according to one embodiment of the present invention.
Figure 31B:
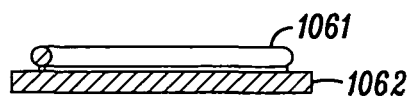

In yet another embodiment, as depicted in FIGS. 31A and 31B, a mechanism to provide lateral position control of a cutting blade mechanism 1063 may include a track (or monorail) 1061 fixed to a backing plate 1062. Cutting blade mechanism 1063 may be advanced and retracted along track 1061 to provide different lateral positions, as depicted in top view in FIG. 31A. FIG. 31B shows a cross-sectional view of track 1061 and backing plate 1062.

Figure 32:
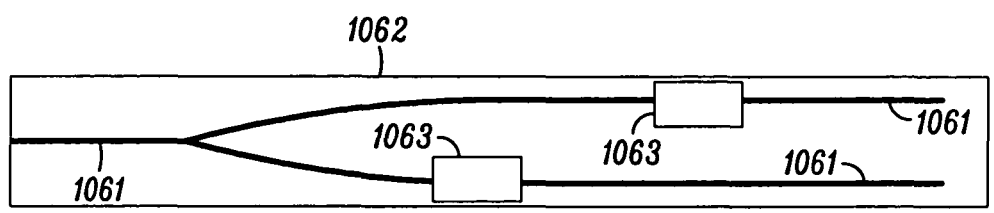
FIG. 32 is a top view of a portion of a tissue modification device including a track along which one or more blades slide according to an alternative embodiment of the present invention.

In an alternative embodiment, as shown in FIG. 32, a track 1061 may include a junction, which may facilitate directing cutting blade mechanism 1063 from one side to another of backing plate 1062.

Figure 33A:
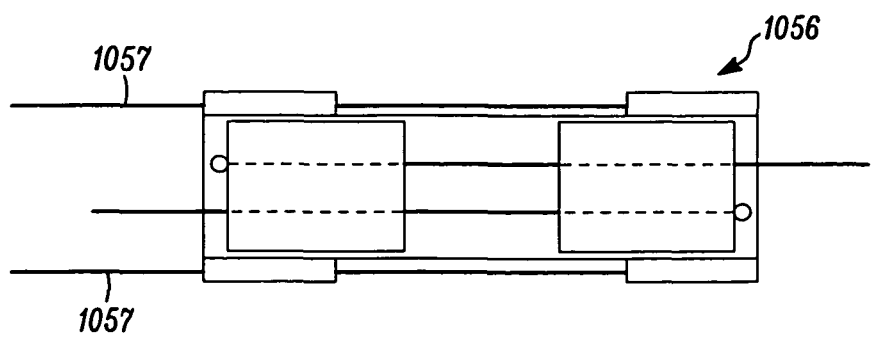
FIGS. 33A-33C are top views of a portion of a tissue modification device including side wires for facilitating guiding of the portion according to an alternative embodiment of the present invention.
Figure 33B:
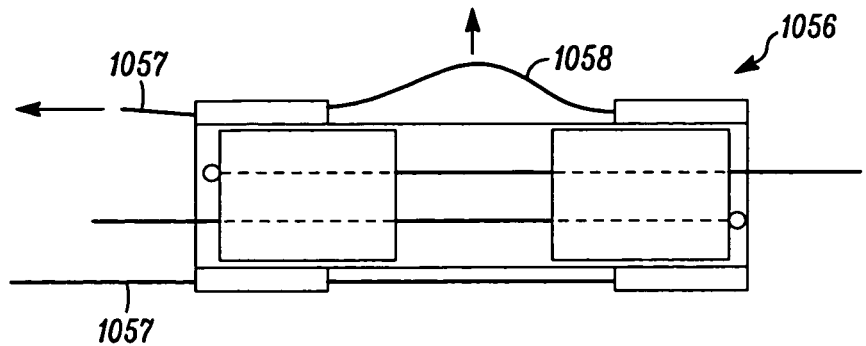
Figure 33C:
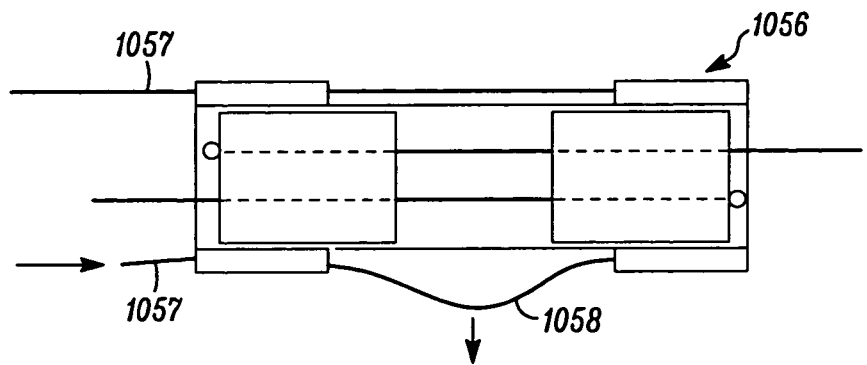

Top-view FIGS. 33A-33C further demonstrate one embodiment of a tissue modifying portion 1056 (here a cutting blade mechanism). These figures show how using push wires 1057 and side-loop wires 1058 on opposite sides of tissue modifying portion 1056, a user may move, guide or steer tissue modifying portion 1056 from side to side (FIGS. 33B and 33C).

Figure 34A:
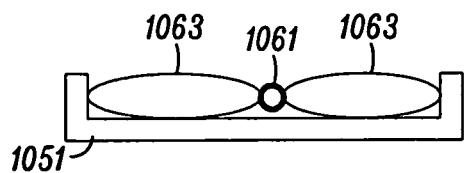

In yet another embodiment, as shown in end-on views in FIGS. 34A-34C, lateral displacement control of a tissue modification device may use one or more fillable bladders 1063, which may be filled or emptied of water, saline, air, or other fluid or gaseous medium to direct one or more components of a tissue modification device to one side or another. In one embodiment, for example, bladders 1063 may be aligned on either side of a track 1061, as depicted in FIG. 34A. As shown in FIGS. 34B and 34C, one bladder 1063 may be deflated or emptied while the other bladder 1063 is filled to move track 1061 to one side, and then the emptied bladder 1063 may be filled and the filled bladder 1063 emptied to move track 1061 to the opposite side.

In yet another embodiment, and with reference now to FIGS. 35A and 35B, a track 1061 is fixed to proximal and distal ends of a backing plate 1062, and the position of track 1061 in between the proximal and distal ends is controlled by a lateral displacer 1064, as shown in top-view in FIG. 35A. When force is applied to move lateral displacer 1064, track 1061 may be shifted relative to backing plate 1062, as shown in FIG. 35B. A cutting blade mechanism advanced or retracted along track 1061 may be controllably displaced from side to side by controlling lateral displacer 1064.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. For example, in many of the embodiments described above, one or more abrasive tissue modifying members may be substituted for one or more bladed tissue modifying members or vice versa. These an many other modifications may be made to many of the described embodiments. Therefore, the foregoing description is provided primarily for exemplary purposes and should not be interpreted to limit the scope of the invention as it is set forth in the claims.

What is claimed is:

1. A method for modifying tissue in a patient, the method comprising:
    advancing a flexible distal portion of an elongate tissue modification device into a patient and along a curved path between a target tissue and a non-target tissue, and advancing a flexible distal portion of a guidewire coupled with the flexible distal portion of the elongate tissue modification device outside the patient through a location that is separate from a location where the device was advanced into the patient;
    positioning a movable blade disposed along one side of the flexible distal portion of the elongate tissue modification device adjacent the target tissue such that the blade faces the target tissue and does not face the non-target tissue;
    urging the movable blade against the target tissue by fixing the distal end of the elongate tissue modification device relative to the patient and pulling a proximal end of the elongate tissue modification device in a proximal direction; and
    moving the movable blade towards a second blade to cut the target tissue without significantly translating the elongate tissue modification device in the proximal direction or a distal direction.

2. A method as in claim 1, wherein the step of advancing comprises advancing the flexible distal portion into an epidural space of the patient's spine.

3. A method as in claim 1, wherein the step of advancing further comprises advancing the flexible distal portion into a spinal channel of the patient.

4. A method as in claim 1, wherein the step of advancing comprises advancing the flexible distal portion into a patient's intervertebral foramen of the patient.

5. A method as in claim 1, wherein the step of moving the movable blade comprises modifying at least one of a ligamentum flavum or a bone of the patient.

6. A method as in claim 1, wherein the step of moving the movable blade further comprises cutting the target tissue to reduce impingement of the target tissue on at least one of a spinal cord, a branching nerve, a dorsal root ganglia, and a vascular tissue in the spine of the patient.

7. A method as in claim 1, wherein the step of urging the movable blade against the target tissue comprises applying a tensioning force or an anchoring force to a first handle and a second handle, the first handle coupled with the elongate tissue modification device at or near the proximal end and the second handle coupled with the elongate tissue modification device at or near the distal end.

8. A method as in claim 1, wherein the step of urging the movable blade against the target tissue comprises:
deploying one or more anchoring members located at or near the distal portion of the elongate tissue modification device within the patient; and
applying a tensioning force to a handle coupled with the proximal end of the elongate tissue modification device.

9. A method as in claim 1, wherein the second blade is an opposing stationary blade.

10. A method as in claim 1, wherein the step of moving the movable blade comprises moving the movable blade laterally, relative to a long axis of the elongate tissue modification device.

11. The method of claim 1, wherein positioning the movable blade comprises positioning a window on the side of the flexible distal portion of the elongate tissue modification device so that the window is adjacent to the target tissue and the movable blade may access the target tissue through the window.

12. A method for modifying spinal tissue to treat spinal stenosis, the method comprising:
advancing a flexible distal portion of an elongate tissue modification device into a patient's intervertebral foramen of the patient's spine, wherein the elongate tissue modification device comprises a movable blade disposed along one side of the flexible distal portion of the elongate tissue modification device, further wherein the movable blade is movable relative to a second blade on the elongate tissue modification device;
positioning the movable blade adjacent a target tissue;
urging the movable blade against the target tissue by fixing the distal portion of the elongate tissue modification device relative to the patient and pulling a proximal end region of the elongate tissue modification device in a proximal direction; and
actuating the movable blade of the elongate tissue modification device to cut the target tissue, so that the movable blade moves towards the second blade without significantly translating the elongate tissue modification device in the proximal direction or in a distal direction; and
advancing a guidewire into the patient at a first location, through the intervertebral foramen of the spine, and back out of the patient at a second location so that opposite ends of the guidewire extend out of the patient.

13. A method as in claim 12, wherein the step of advancing the flexible distal portion of the elongate tissue modification device comprises coupling the elongate tissue modification device and the guidewire, and advancing the elongate tissue modification device using the guidewire.

14. A method as in claim 12, wherein the second blade is stationary.

15. A method as in claim 12, wherein the step of actuating the movable blade comprises triggering a handle portion at the proximal end of the elongate tissue modification device.

16. A method as in claim 12, further comprising:
moving the flexible distal portion of the elongate tissue modification device in the intervertebral foramen of the patient; and actuating the movable blade again to cut tissue.

17. The method of claim 12, wherein positioning the movable blade comprises positioning a window on the side of the flexible distal portion of the elongate tissue modification device so that the window is adjacent to the target tissue and the movable blade may access the tissue through the window.

18. A method for modifying tissue in a patient, the method comprising:
advancing a flexible distal portion of an elongate tissue modification device into the patient and along a curved path between a target tissue and a non-target tissue, and advancing the flexible distal portion of the elongate tissue modification device outside the patient through a location that is separate from a location where the device was advanced into the patient;
positioning a movable blade disposed along one side of the elongate tissue modification device adjacent the target tissue such that the movable blade faces the target tissue and does not face the non-target tissue;
urging the movable blade against the target tissue by fixing the distal portion of the elongate tissue modification device relative to the patient and pulling a proximal end of the elongate tissue modification device in a proximal direction; and
moving the movable blade towards a second blade to cut the target tissue without significantly translating the elongate tissue modification device in the proximal direction or in a distal direction.

19. A method for modifying tissue in a patient, the method comprising:
advancing a flexible distal portion of an elongate tissue modification device into the patient and along a curved path between a target tissue and a non-target tissue;
positioning a movable blade disposed along one side of the flexible distal portion of the elongate tissue modification device adjacent the target tissue such that the movable blade faces the target tissue and does not face the non-target tissue;
urging the movable blade against the target tissue by fixing the distal portion of the elongate tissue modification device relative to the patient and pulling a proximal end of the elongate tissue modification device in a proximal direction and applying a tensioning force or an anchoring force to a first handle and a second handle, the first handle coupled with the elongate tissue modification device at or near the proximal end and the second handle coupled with the elongate tissue modification device at or near the distal portion; and
moving the movable blade towards a second blade to cut the target tissue without significantly translating the elongate tissue modification device in the proximal direction or in to distal direction.

20. A method for modifying tissue in a patient, the method comprising:
advancing a curved, rigid distal portion of an elongate tissue modification device into the patient and along a curved path between a target tissue and a non-target tissue;
positioning a movable blade disposed along one side of the distal portion of the elongate tissue modification device adjacent the target tissue such that the movable blade faces the target tissue and does not face the non-target tissue;

urging the movable blade against the target tissue by fixing the distal portion of the elongate tissue modification device relative to the patient and pulling a proximal end of the elongate tissue modification device in a proximal direction; and moving the movable blade towards a second blade to cut the target tissue without significantly translating the elongate tissue modification device in the proximal direction or in a distal direction.

21. A method as in claim 20, wherein the step of advancing comprises advancing the curved distal portion into an epidural space of the patient's spine.

22. A method as in claim 20, wherein the step of advancing further comprises advancing the curved distal portion into a spinal channel of the patient.

23. A method as in claim 20, wherein the step of advancing comprises advancing the curved distal portion toward a patient's intervertebral foramen.

24. A method as in claim 20, wherein the step of moving the movable blade comprises modifying at least one of a ligamentum flavum of the patient and a bone of the patient.

25. A method as in claim 20, wherein the step of moving the movable blade further comprises cutting the target tissue to reduce impingement of the target tissue on at least one of a spinal cord, a branching nerve, a dorsal root ganglia, and a vascular tissue in the patient's spine.

26. A method for modifying spinal tissue to treat spinal stenosis, the method comprising:

advancing a curved, rigid distal portion of an elongate tissue modification device toward a patient's intervertebral foramen of the spine, wherein the elongate tissue modification device comprises a movable blade disposed along one side of the distal portion of the elongate tissue modification device, further wherein the movable blade is movable relative to a second blade on the elongate tissue modification device;

positioning the movable blade adjacent a target tissue;

urging the movable blade against the target tissue by fixing the distal portion of the elongate tissue modification device relative to the patient and pulling a proximal end region of the elongate tissue modification device in a proximal direction; and actuating the movable blade of the elongate tissue modification device to cut the target tissue, so that the movable blade moves towards a second blade without significantly translating the elongate tissue modification device in the proximal direction or in a distal direction.

27. A method as in claim 26, wherein the step of moving the movable blade comprises modifying at least one of a ligamentum flavum of the patient and a bone of the patient.

28. A method as in claim 26, wherein the step of moving the movable blade further comprises cutting the target tissue to reduce impingement of the target tissue on at least one of a spinal cord, a branching nerve, a dorsal root ganglia, and a vascular tissue in the spine of the patient.

* * * * *